(12) United States Patent
Bonde

(10) Patent No.: US 12,364,855 B2
(45) Date of Patent: Jul. 22, 2025

(54) INTRACARDIAC DEVICE

(71) Applicant: YALE UNIVERSITY, New Haven, CT (US)

(72) Inventor: Pramod Bonde, Woodbridge, CT (US)

(73) Assignee: YALE UNIVERSITY

( * ) Notice: Subject to any disclaimer, the term of this patent is extended or adjusted under 35 U.S.C. 154(b) by 1151 days.

(21) Appl. No.: 17/252,065

(22) PCT Filed: Jun. 13, 2019

(86) PCT No.: PCT/US2019/037047
§ 371 (c)(1),
(2) Date: Dec. 14, 2020

(87) PCT Pub. No.: WO2019/241556
PCT Pub. Date: Dec. 19, 2019

(65) Prior Publication Data
US 2021/0260359 A1    Aug. 26, 2021

Related U.S. Application Data

(60) Provisional application No. 62/684,381, filed on Jun. 13, 2018.

(51) Int. Cl.
*A61M 60/165* (2021.01)
*A61M 60/135* (2021.01)
(Continued)

(52) U.S. Cl.
CPC ........ *A61M 60/422* (2021.01); *A61M 60/135* (2021.01); *A61M 60/232* (2021.01);
(Continued)

(58) Field of Classification Search
CPC ................................................. A61M 2205/04
See application file for complete search history.

(56) References Cited

U.S. PATENT DOCUMENTS 2,500,400 A * 3/1950 Cogswell .............. F04D 13/043
310/67 R
3,719,436 A    3/1973 McFarlin
(Continued)

FOREIGN PATENT DOCUMENTS

WO    WO-2016100600 A2 *    6/2016 .......... A61M 1/1029

OTHER PUBLICATIONS

International Search Report and Written Opinion for App. No. PCT/US2019/037047, dated Sep. 4, 2019, 8 pages.
(Continued)

*Primary Examiner* — Catherine M Voorhees
*Assistant Examiner* — James Moss
(74) *Attorney, Agent, or Firm* — Riverside Law LLP

(57) ABSTRACT

The present invention provides intracardiac devices and methods of implanting the same. The intracardiac devices have a collapsible stent design and include an axial pump to support cardiac function. The axial pump can feature a shaftless fluid actuator for enhanced efficiency in fluid transfer while reducing blood cell trauma. The intracardiac devices include valves that are closeable to seal implanted devices from a subject's anatomy. The intracardiac devices include a cleaning system configured to introduce and circulate cleaning solutions and therapeutics to implanted devices. The intracardiac devices are wirelessly powered and controlled. The intracardiac devices can be implanted using minimally invasive procedures without the need for open heart surgery.

22 Claims, 66 Drawing Sheets

(51) Int. Cl.
*A61M 60/232* (2021.01)
*A61M 60/237* (2021.01)
*A61M 60/419* (2021.01)
*A61M 60/422* (2021.01)
*A61M 60/515* (2021.01)
*A61M 60/523* (2021.01)
*A61M 60/81* (2021.01)
*A61M 60/865* (2021.01)
*A61M 60/873* (2021.01)
*A61M 60/892* (2021.01)

(52) U.S. Cl.
CPC ........ *A61M 60/237* (2021.01); *A61M 60/419* (2021.01); *A61M 60/515* (2021.01); *A61M 60/523* (2021.01); *A61M 60/81* (2021.01); *A61M 60/865* (2021.01); *A61M 60/873* (2021.01); *A61M 60/892* (2021.01); *A61M 2205/04* (2013.01); *A61M 2205/3324* (2013.01); *A61M 2205/3334* (2013.01); *A61M 2205/3368* (2013.01); *A61M 2230/06* (2013.01); *A61M 2230/205* (2013.01)

(56) References Cited

U.S. PATENT DOCUMENTS

| | | | | |
|---|---|---|---|---|
| 5,290,227 A | * | 3/1994 | Pasque | A61M 60/422 623/3.13 |
| 2001/0009645 A1 | | 7/2001 | Noda | |
| 2001/0041934 A1 | * | 11/2001 | Yamazaki | A61M 60/196 623/3.13 |
| 2007/0250146 A1 | * | 10/2007 | Cully | A61F 2/915 623/1.2 |
| 2008/0114339 A1 | * | 5/2008 | McBride | A61M 60/148 416/142 |
| 2008/0292478 A1 | * | 11/2008 | Baykut | F04D 29/181 417/423.12 |
| 2012/0059459 A1 | * | 3/2012 | Asirvatham | A61M 60/20 623/3.26 |
| 2013/0042892 A1 | * | 2/2013 | Lynch | A61M 60/148 134/166 R |
| 2013/0310630 A1 | * | 11/2013 | Smith | A61M 60/538 600/16 |
| 2014/0275727 A1 | * | 9/2014 | Bonde | A61M 60/178 600/16 |
| 2015/0306291 A1 | * | 10/2015 | Bonde | A61M 60/865 600/16 |
| 2016/0045654 A1 | * | 2/2016 | Connor | A61M 60/894 600/16 |
| 2016/0129169 A1 | * | 5/2016 | Forsell | A61M 60/226 600/16 |
| 2016/0375187 A1 | * | 12/2016 | Lee | A61M 60/804 600/16 |
| 2020/0023158 A1 | * | 1/2020 | Epple | F04B 43/1223 |
| 2020/0215245 A1 | * | 7/2020 | Haddadi | A61M 60/422 |

OTHER PUBLICATIONS

Chinese Office Action issued in App. No. CN201980054225, dated Dec. 22, 2023, 10 pages.

* cited by examiner

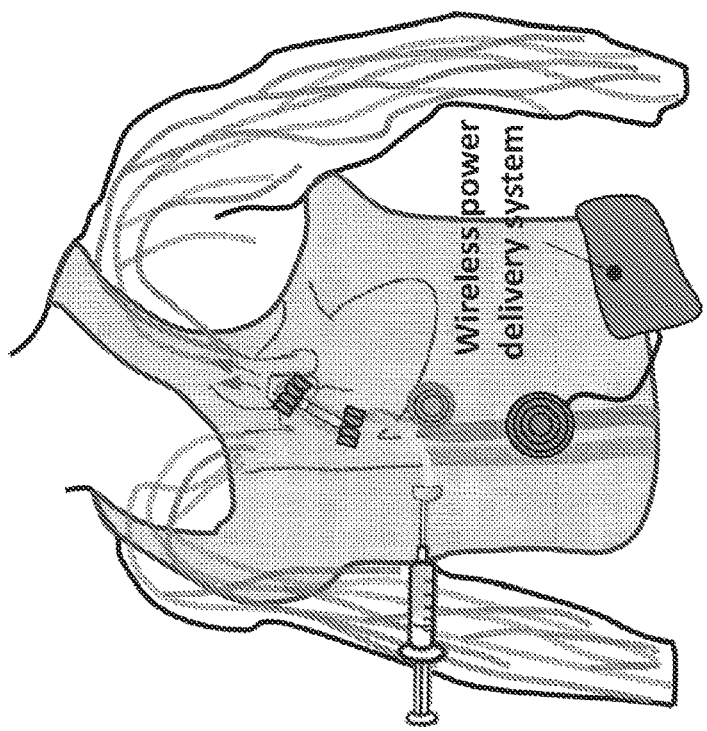
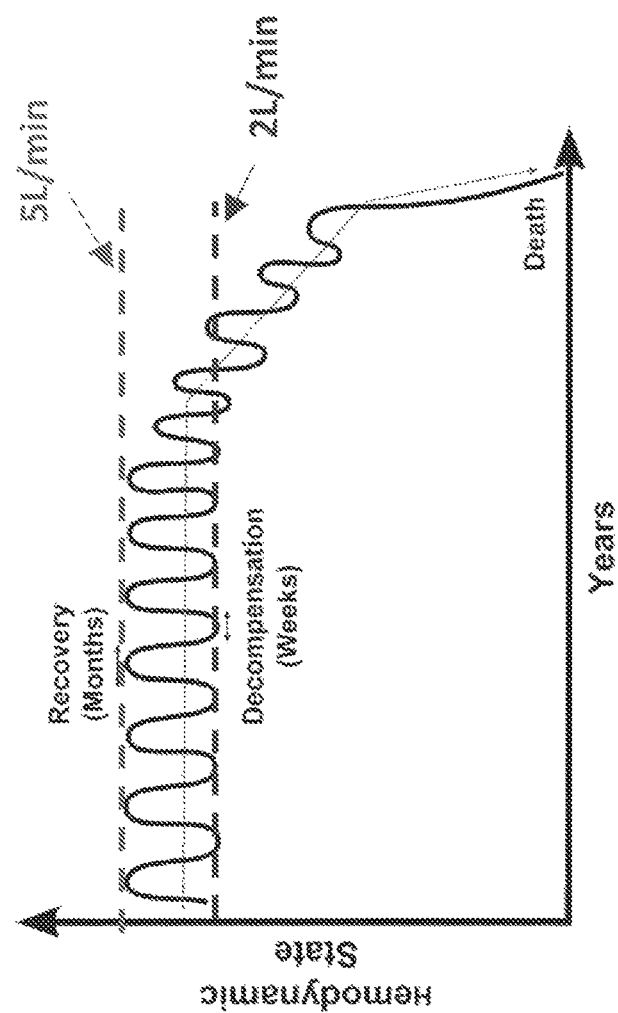
FIG. 10

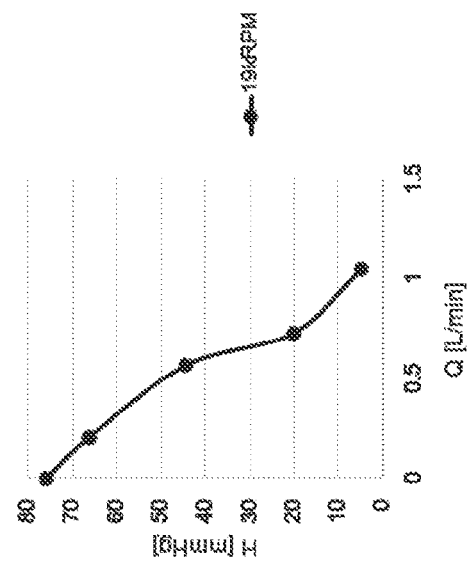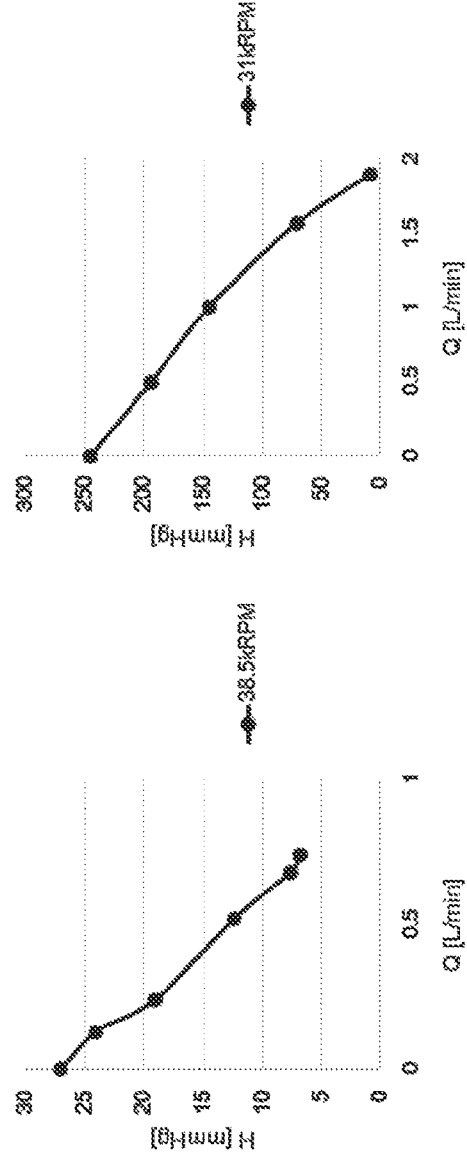
FIG. 21

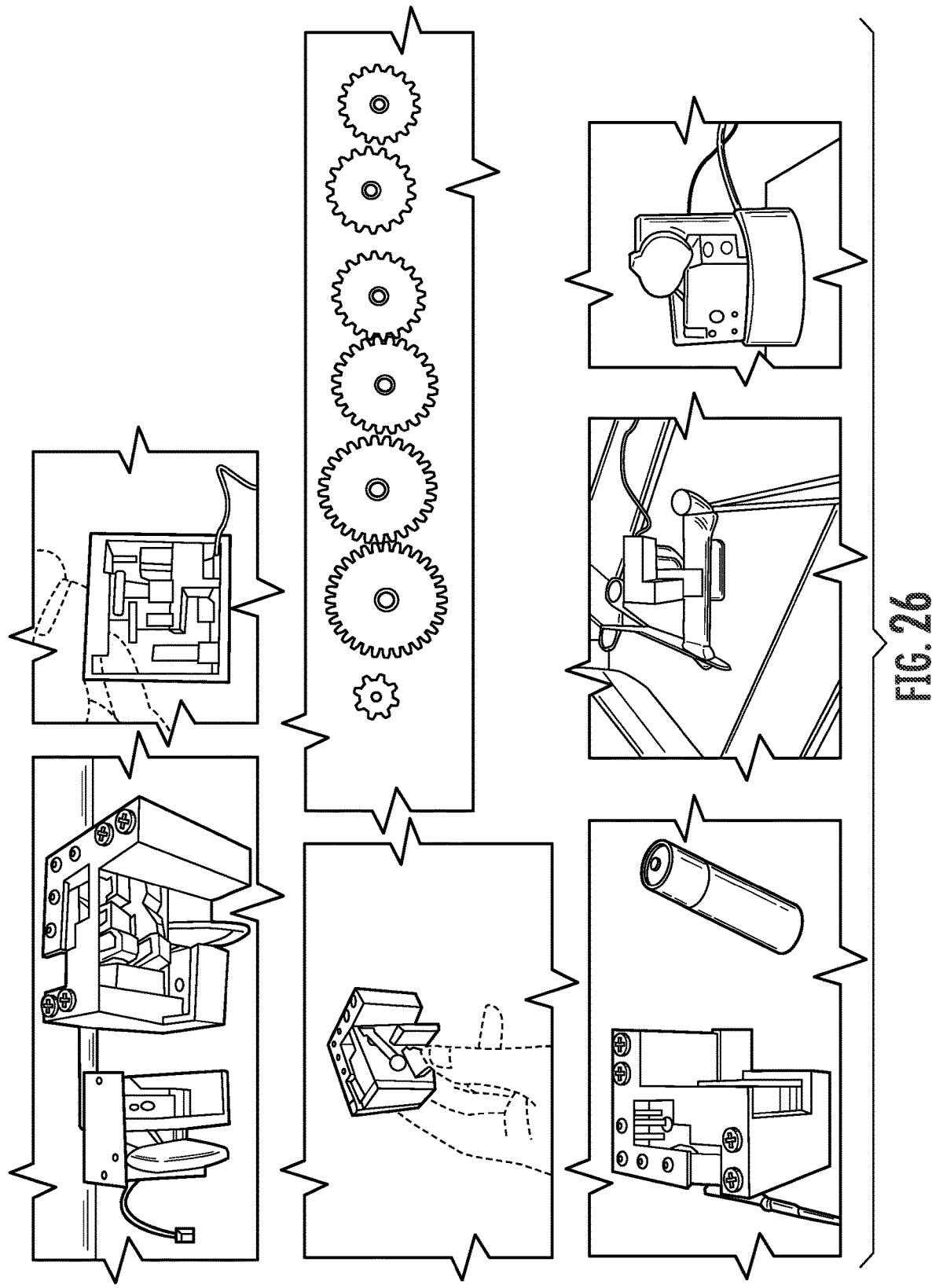

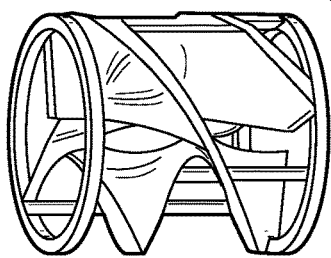
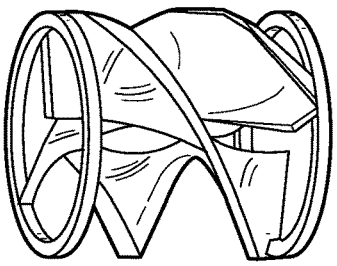
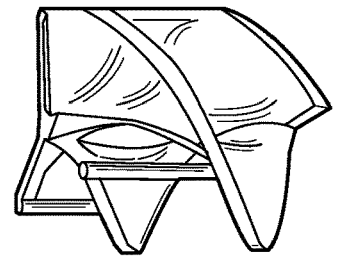
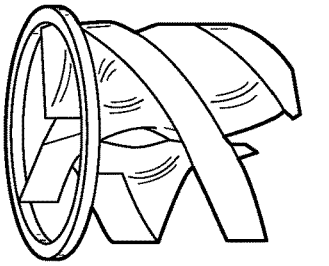
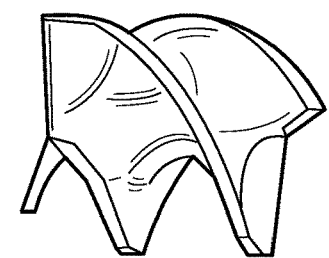
FIG. 44A
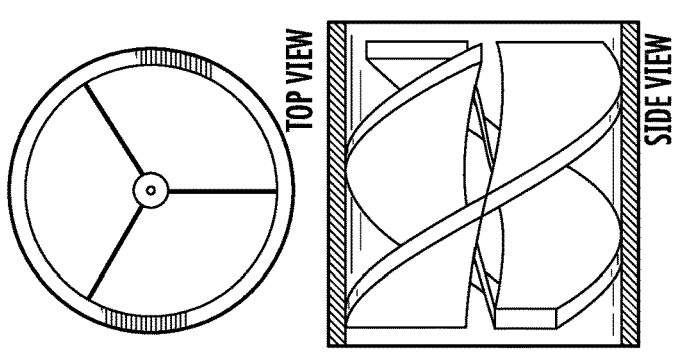
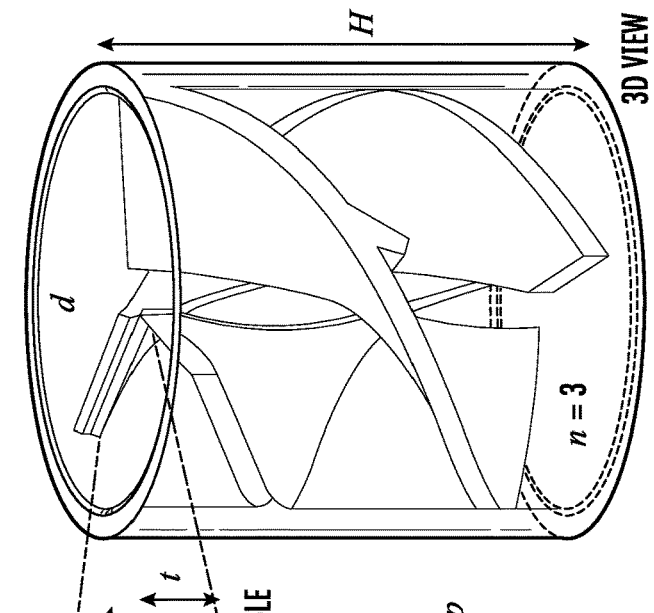
- INNER DIAMETER ($d$)
- HELIX HEIGHT ($H$)
- HELIX PITCH ($p$)
- BLADE LENGTH ($l$)
- BLADE THICKNESS ($t$)
- INTRODUCTORY BLADE ANGLE ($\alpha$)
- NUMBER OF BLADES ($n$)
- BLADE SHAPE
FIG. 44B

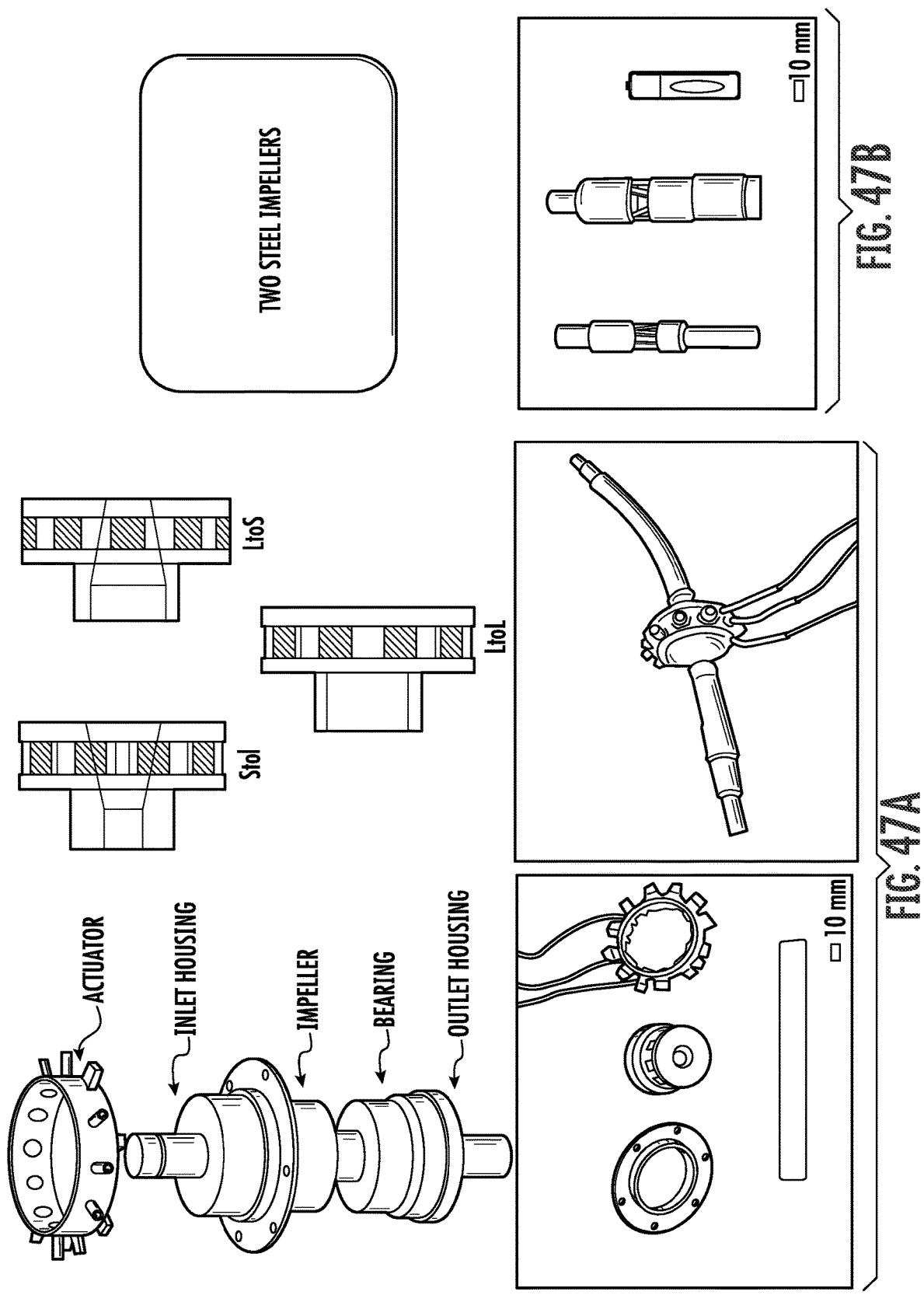

FIG. 52A  Large inlet to Large outlet (LtoL)

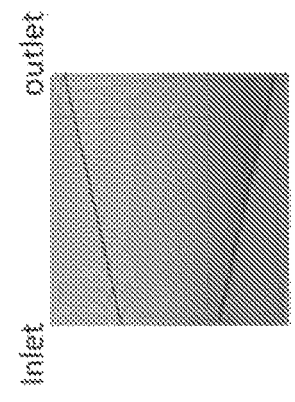

| | Throttle | Flow direction | Max flow |
|---|---|---|---|
| CCW | 1600 | ← | 2 L/min |
| CW | 1600 | → | 1.42 L/min |

*throttle is linearly related to RPM

FIG. 52B  Small inlet to Large outlet (StoL)

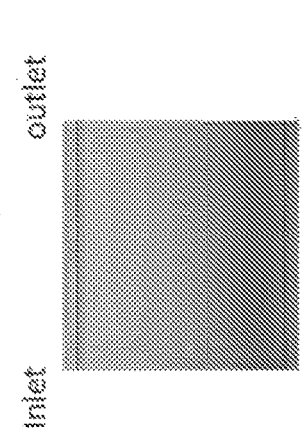

| | Throttle | Flow direction | Max flow |
|---|---|---|---|
| CCW | 1600 | No flow | 0 L/min |
| CW | 1600 | → | 1.23 L/min |

*throttle is linearly related to RPM

FIG. 52C  Large inlet to Small outlet (LtoS)

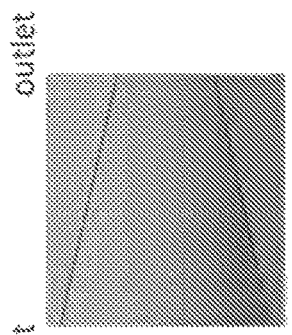

| | Throttle | Flow direction | Max flow |
|---|---|---|---|
| CCW | 1600 | ← | 1.23 L/min |
| CW | 1600 | No flow | 0 L/min |

*throttle is linearly related to RPM

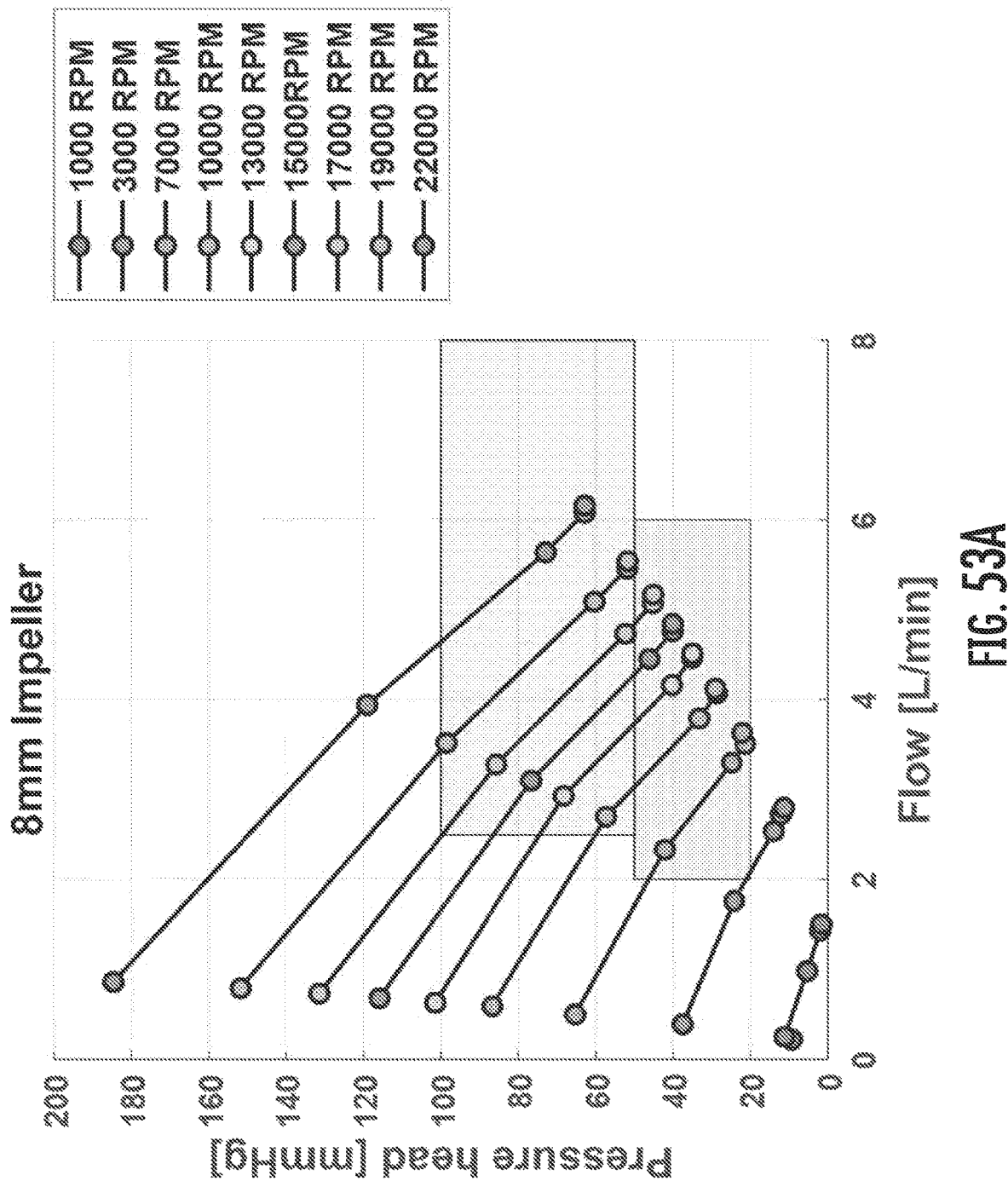

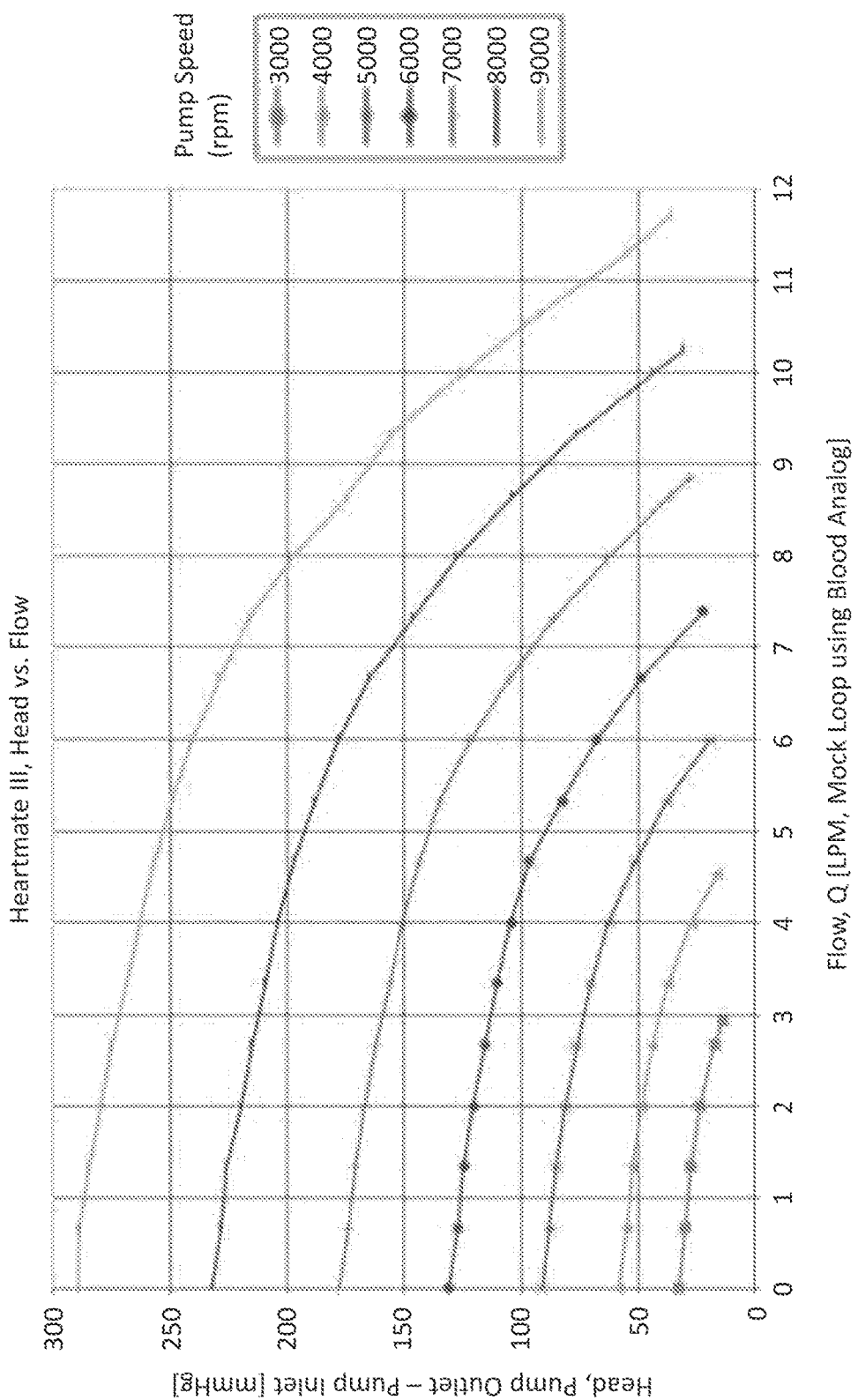

INTRACARDIAC DEVICE

CROSS-REFERENCE TO RELATED APPLICATIONS

This application is a national stage filing of International Patent Application No. PCT/US19/37047, filed Jun. 13, 2019, which claims priority to U.S. Provisional Patent Application No. 62/684,381, filed Jun. 13, 2018, the contents of which are incorporated by reference herein in their entireties.

BACKGROUND OF THE INVENTION

Early class III heart failure patients can benefit greatly from an increase in their cardiac output, provided they do not suffer from the adverse events related to current left ventricular assist devices (LVADs), such as stroke, drive line infections, and pump thrombosis. Furthermore, the fundamental footprint of impeller design in artificial heart pumps has remained unchanged since the first rotary ventricular assist device (VAD), the Jarvik 2000 FlowMaker, came out in 1982. Different numbers of blades attached to a central hub within different angles, lengths, thicknesses, gap sizes, etc. have been extensively explored to optimize hemodynamic performance while minimizing hemolysis and thrombosis for different applications. Tremendous efforts have been made to reduce mechanical components contacting blood while retaining the framework of impeller design. Despite the improvements of survival and quality of life achieved with advances in VAD technology, adverse prothrombotic events remain a problem. For example, current impeller designs force blood cells to pass over limited space available within the rapidly alternating blades attached along a central hub and creates a fundamentally non-physiological flow.

There is a need in the art for improved ventricular assist devices with less traumatic impellers. The present invention addresses this need.

SUMMARY OF THE INVENTION

In one aspect, the present invention provides an intracardiac device comprising: an elongate tubular body having a lumen running between two open ends; an axial pump positioned within the lumen; at least one valve positioned at each open end; and a centrifugal pump having an inlet and an outlet fluidly connected to the lumen of the body by a first and a second tube and a side port fluidly connected to at least one cleaning port by a third tube.

In one embodiment, the device further comprises a wireless power system having a transmitting coil electrically connected to a battery and an implantable receiving coil electrically connected to the axial pump, each of the valves, and the centrifugal pump.

In one embodiment, wherein the body has a collapsible stent construction having a membrane covering. In one embodiment, wherein the membrane covering is pericardium, a polymer, or combinations thereof.

In one embodiment, the axial pump comprises: an elongate housing having a motor at a first end and an open second end; a rotor positioned within the housing between the first end and the second end, the rotor being engaged to the motor; at least one side inlet on the housing positioned near the rotor; and a diffusor positioned near the open end.

In one embodiment, the rotor has a shaftless design comprising: a hollow, substantially cylindrical housing having a height, an inner diameter, an outer surface, an inner surface, and a long axis running from two open ends; and at least one blade attached to the inner surface of the housing in a helical pattern, each blade having a pitch, a length extending from the inner surface of the housing, a thickness, and an angle relative to the inner surface of the housing; wherein each blade has a length less than half the diameter of the housing.

In one embodiment, the rotor has a height between about 15 and 25 mm and an inner diameter between about 10 and 30 mm. In one embodiment, the pitch of each blade is individually adjustable. In one embodiment, the housing is driven by a motor engaged to its outer surface, its inner surface, or to an open end. In one embodiment, the housing further comprises embedded magnets. In one embodiment, the housing is driven by an electromagnet or a rotating magnet.

In one embodiment, the at least one valve is selected from the group consisting of: a stepper valve, a clamp, an iris valve, a solenoid valve, a memory alloy valve, a diaphragm valve, a balloon occlude, a single-leaflet valve, and a multi-leaflet valve.

In one embodiment, the device further comprises at least one oxygen sensor, pH sensor, flow sensor, temperature sensor, and heart rate monitor. In one embodiment, the device further comprises an implantable wireless receiver and an external controller, the controller configured to activate and modulate the axial pump, each of the valves, and the centrifugal pump.

In another aspect, the present invention provides a method of minimally invasive implantation, comprising the steps of: providing the intracardiac device of the present invention; forming a first aperture in a subject's fossa ovalis, bridging the right atrium with the left atrium, and forming a second aperture in a subject's sinotubular junction, bridging the right atrium with the aorta; and inserting the intracardiac device into the subject's heart such that a first end is secured to the first aperture, a second end is secured to the second aperture, and the intracardiac device rests in the right atrial appendage, forming a fluid pathway between the left atrium and the aorta.

In one embodiment, the first aperture is formed by inserting a guidewire through the femoral vein or the internal jugular into the right atrium and guiding a puncture needle and dilator to the fossa ovalis. In one embodiment, the second aperture is formed by inserting a guidewire through the carotid artery or the femoral artery into the aorta and guiding a puncture needle and dilator to the sinotubular junction.

In another aspect, the present invention provides a method of sealing the device of the present invention, comprising the steps of closing each of the valves at both ends of the device.

In another aspect, the present invention provides a method of cleaning the device of the present invention, comprising the steps of: closing each of the valves at both ends of the device; activating the centrifugal pump; injecting a cleaning solution into a first cleaning port; and extracting spent cleaning solution from a second cleaning port.

In another aspect, the present invention provides a method of administering a therapeutic to a subject through the device of the present invention, comprising the steps of: activating the centrifugal pump; and injecting a therapeutic into a first cleaning port.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 10 depicts the effects of decompensation and recovery in class III heart failure and the treatment provided by an exemplary intracardiac device.

FIG. 21 depicts the experimental results of testing the performance of differently dimensioned prototype axial pumps under varied operational conditions.

FIG. 26 depicts various prototype gearbox driven valves.

FIG. 27A depicts a transmitting coil (left) and a receiving coil (right). FIG. 27B depicts a controller and transmitter. FIG. 27C depicts a receiver printed circuit board and the receiver coil encased in polydimethylsiloxane.

FIG. 44A and FIG. 44B depict the conceptual phases of impeller design.

FIG. 44A depicts the initial design process inspired by the avian heart valve. FIG. 44B depicts the design parameters used to modulate pump performance. All corresponding parameters are annotated in the three-dimensional view of the impeller design.

(FIG. 46A) Mod 1: Final model reached through initial design process on each parameter specified in FIG. 44B. (FIG. 46B) Mod 2: The second model with design modifications from Mod 1 based on findings in Mod 1 analysis. Tapered ends for a smooth blood transition into the gap were implemented. The cut off at the leading edge in Mod 1 was replaced with a rounded edge to decrease hydraulic losses. The trailing edge was transformed to a vertical cut-off. Among all, the key features added to Mod 2 were the troughs on the outside with the same wrap angle as that of impeller blades, which is expected to prevent the backflow through the outer gaps and increase overall pump efficiency. (FIG. 46C) Geometrical setup for the pump assessment in Ansys software.

FIG. 47A and FIG. 47B depict the prototype impeller and pump designs.

FIG. 49B and FIG. 49D show hydraulic power on single blade of each model, evaluated at pump flows below ($V<V_{bep}$), at ($V=V_{bep}$), and above ($V>V_{bep}$) the best hydraulic efficiency points (BEP) for 15,000 RPM. Since the impeller geometry is symmetric, the distribution of hydraulic power can be assumed to be similar for the other two blades.

(FIG. 51A) Flow field within Mod 1 when the pump flow (V) is below ($V<V_{bep}$), at ($V=V_{bep}$), and above ($V>V_{bep}$) the best efficiency point for 12,500 RPM. (FIG. 51B) Quantified back flow within Mod 1 and 2. The implementation of the troughs on the impeller bushing in Mod 2 significantly decreased the secondary gap backflow compared to Mod 1.

FIG. 52A through FIG. 52C depict the results of experiments investigating the effect of inlet and outlet dimensions on flow rates. FIG. 52A has a large inlet and a large outlet, FIG. 52B has a small inlet and a large outlet, and FIG. 52C has a large inlet and a small outlet.

FIG. 53A and FIG. 53B depict pump performance curves for a small (FIG. 53A) and a large (FIG. 53B) impeller, respectively.

FIG. 54A through FIG. 54C depict pressure to flow rate performance at various RPM for three commonly used assist devices: HeartMate II (FIG. 54A); HeartWare HVAD (FIG. 54B); and HeartMate III (FIG. 54C).

FIG. 55A depicts a wide and a narrow impeller prototype next to a AAA battery for size comparison. FIG. 55B depicts machined and 3D printed impeller prototypes. FIG. 55C depicts views of the opposing ends of an impeller prototype, wherein the unobstructed bore design is visible.

DETAILED DESCRIPTION

Figure 1:
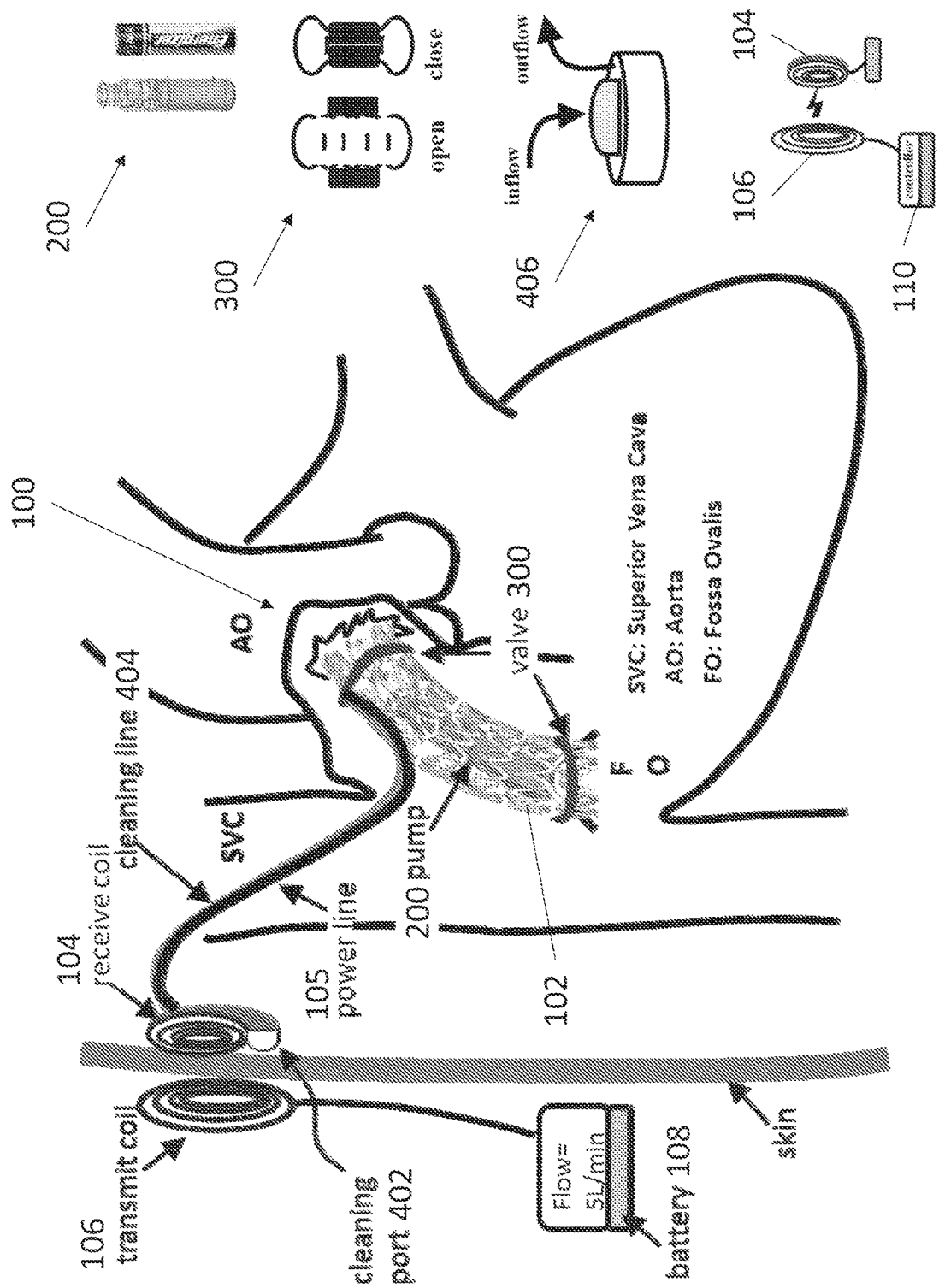
FIG. 1 is a schematic depicting an exemplary intracardiac device.

The present invention provides intracardiac devices and methods of implanting the same. The intracardiac devices have a collapsible stent design and include an axial pump to support cardiac function. The axial pump can feature a shaftless fluid actuator for enhanced efficiency in fluid transfer while reducing blood cell trauma. The intracardiac devices include valves that are closeable to seal implanted devices from a subject's anatomy. The intracardiac devices include a cleaning system configured to introduce and circulate cleaning solutions and therapeutics to implanted devices. The intracardiac devices are wirelessly powered and controlled. The intracardiac devices can be implanted using minimally invasive procedures without the need for open heart surgery.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Intracardiac Device

The present invention provides improved intracardiac devices. The intracardiac devices can be implanted for cardiac support, such as in the case of ventricular failure. The intracardiac devices have a collapsible construction for use in minimally invasive implantation. In one aspect, the intracardiac devices have inflow and outflow valves. Closing the inflow and outflow valves modulate flow and are capable of sealing the intracardiac devices, prolonging the life of the devices when not in use. In one aspect, the intracardiac devices include a cleaning system. The cleaning system includes an access port and a centrifugal pump that enables the introduction and rapid circulation of a cleaning solution into the intracardiac devices. Coupling the cleaning system the inflow and outflow valves allows for maintenance of the devices while implanted without biological or chemical fouling (such as stenosis, intimal hyperplasia, encrustation, and the like). In one aspect, the intracardiac devices include a novel fluid actuator. The fluid actuator provides a shaftless design to drive a greater amount of fluid using less power, and is less traumatic to cells and other structures that may be present in a fluid.

Referring now to FIG. 1, an exemplary intracardiac device 100 is depicted. Intracardiac device 100 comprises a substantially cylindrical stent body 102 having a lumen running between two open ends, a valve 300 positioned at each open end, axial pump 200 positioned between each valve 300, and cleaning system 400 fluidly connected to the lumen. Stent body 102 can have a mesh or wire construction, such that stent body 102 can be collapsible into a narrow configuration to facilitate insertion and expandable at a site of implantation. In certain embodiments, stent body 102 comprises a covering, which can have a biological (such as pericardium or engineered tissue scaffold), artificial (such as a polymer), or a biological and artificial hybrid construction.

The various components of device 100, including each valve 300, axial pump 200, and cleaning system 400, can be powered by receiving coil 104 and power line 105 wirelessly receiving electromagnetic energy from transmitting coil 106 and battery 108. In certain embodiments, device 100 further comprises a wireless receiver and a controller 110 configured to communicate with the wireless receiver to activate and modulate each of the components of device 100. For example, controller 110 can be configured to wirelessly open and close each valve 300, to activate and modulate the speed of axial pump 200, and to activate cleaning system 400. Prototype receiving coils 104 and transmitting coils 106 and experimental results are depicted in FIG. 27A through FIG. 29B.

Figure 2:
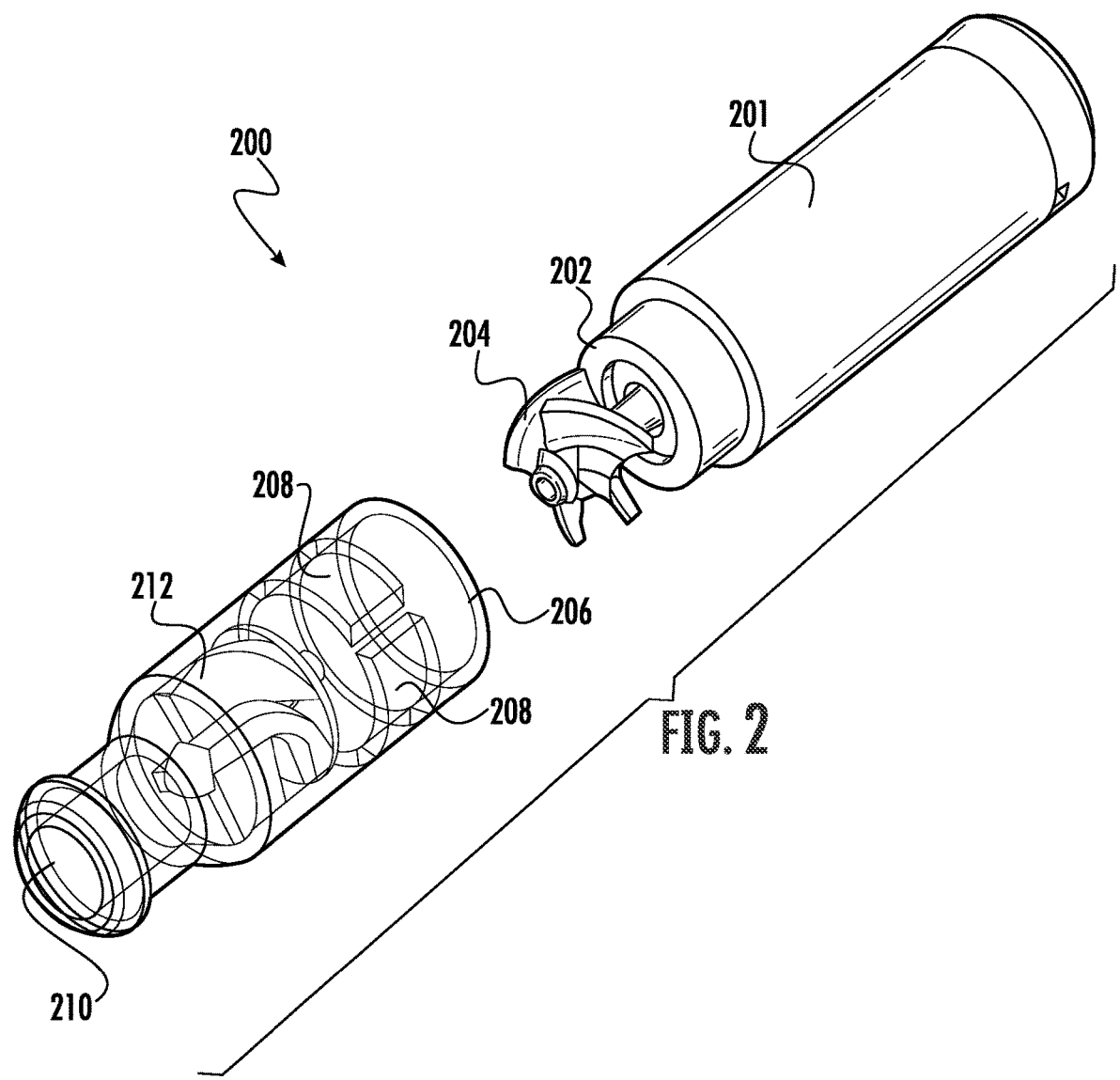
FIG. 2 depicts the axial pump component of an exemplary intracardiac device.

Referring now to FIG. 2, axial pump 200 is depicted in greater detail. Axial pump 200 comprises housing 201 attachable to sheath 206. Motor 202 fits within housing 201 and is attached to rotor 204. Sheath 206 comprises at least one inlet 208 and an outlet 210 and contains diffusor 212 positioned near outlet 210. The at least one inlet 208 is configured to be positionable adjacent to rotor 204 when sheath 206 is attached to housing 201. Rotor 204 is configured to be actuated by motor 202 and to draw in a fluid through the at least one inlet 208, whereupon the fluid is advanced towards outlet 210. Diffusor 212 guides the fluid towards outlet 210 in a manner that reduces turbulent flow. Prototype axial pumps 200 and experimental results are depicted in FIG. 17 through FIG. 21.

Figure 3:
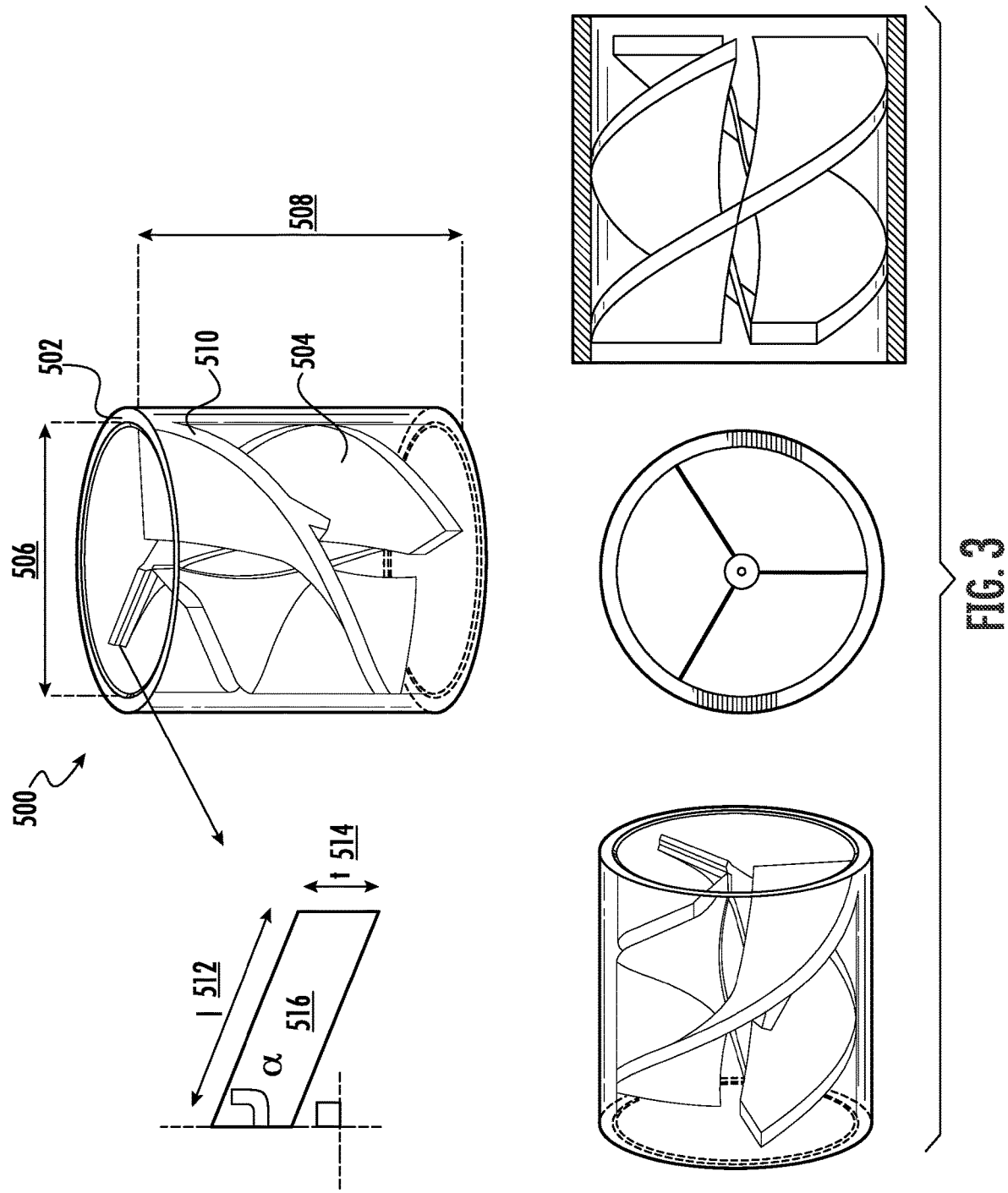
FIG. 3 depicts an exemplary fluid actuator compatible with the axial pump component of an exemplary intracardiac device.

In some embodiments, axial pump 200 can alternatively employ fluid actuator 500, shown in FIG. 3. Fluid actuator 500 provides a shaftless design for the actuation of fluids and comprises housing 502 having a plurality of blades 504. Housing 502 has a hollow, substantially cylindrical shape having a long axis with open ends and an outer and an inner surface. Each of the blades 504 is attached to the inner surface of housing 502 and extends from opposite ends of housing 502 in a helical pattern. Blades 504 are thereby configured to actuate a fluid by the rotation of housing 502 along its long axis. The rotation can be achieved by mechanical linkage with a motor, such as by a rim-driven connection (FIG. 47A) or an end-driven connection (FIG. 47B). The rotation can also be achieved by magnetic coupling with external electromagnets or a rotating magnet. While blades 504 are depicted as having a substantially parallelogram-like cross-sectional shape, it should be understood that blades 504 can have any suitable cross-sectional shape, including rectangular, with rounded edges, with sharp edges, and the like.

The dimensions of actuator 500 can be tuned to suit a particular application, and include inner diameter 506 and height 508 of housing 502 as well as pitch 510, length 512, thickness 514, and angulation 516 of blades 504. In certain embodiments, height 508 can be between about 15 and 25 mm, wherein larger heights increase volume flow rate and head pressure. In certain embodiments, inner diameter 506 can be between about 10 and 30 mm, wherein larger diameters increase volume flow rate and head pressure. Pitch 510 can be described as a number of revolutions per unit of height 508, and in certain embodiments can vary between about 0.2 and 1 revolution per 10 mm, 15 mm, and 25 mm. An optimal pitch 510 thereby depends on the specific height 508, and generally a greater pitch decreases torque. In some embodiments, one or more blades 504 can have a variable pitch 510, wherein pitch 510 can be individually controlled while actuator 500 is in motion to modulate torque and flow. In certain embodiments, length 512 can be between about 3 mm and 8 mm, wherein larger lengths increase volume flow rate and head pressure. In certain embodiments, thickness 514 can be between about 0.1 mm and 2 mm. It should be understood that the dimensional ranges provided herein are exemplary in nature and in the context of an axial pump suitable for use in an intracardiac device. Actuator 500 can have any suitable dimensions to drive any desired fluid, including gases, air, viscous fluids, solids, semisolids, particulates, and the like. Actuator 500 can have applications beyond fluid transport, including propulsion in aeronautics, above water and below water vessels, land transportation, drone mobility, and the like. Prototype actuators 500 and experimental results are depicted in FIG. 30 through FIG. 43.

Figure 4:
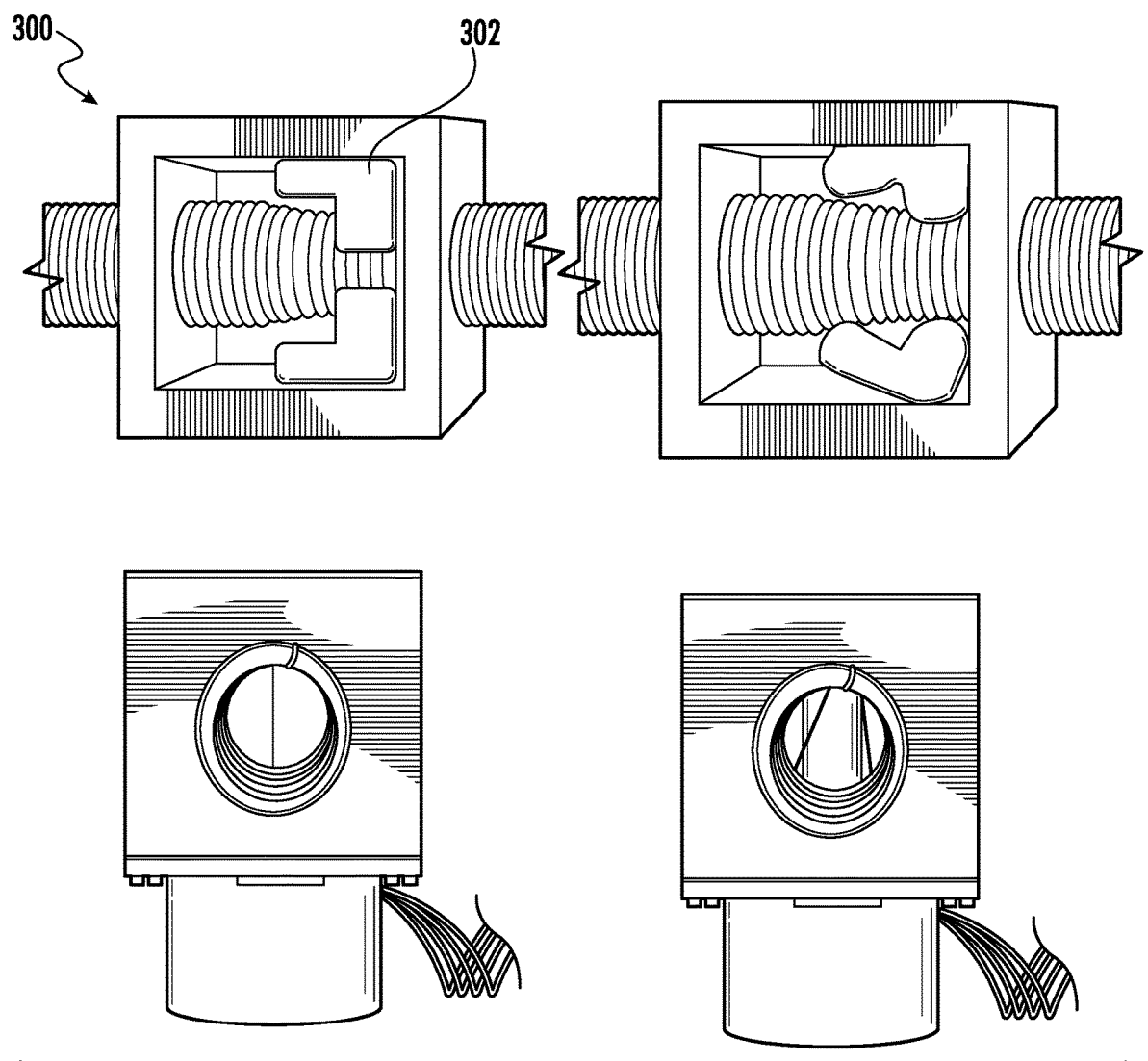
FIG. 4 depicts an opened and closed valve component of an exemplary intracardiac device.
Figure 5:
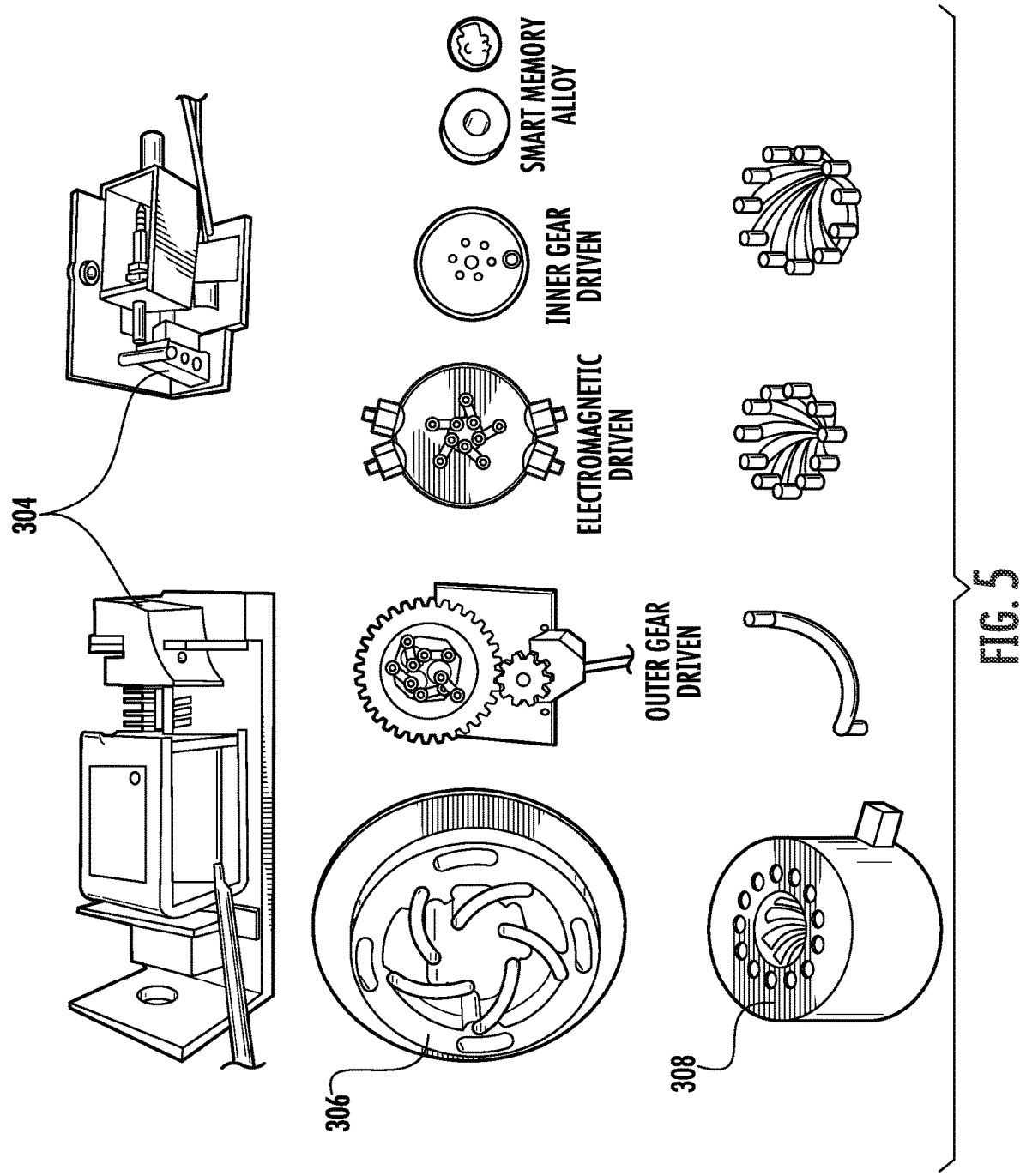
FIG. 5 depicts several alternative valve components of an exemplary intracardiac device.

Valve 300 can be any suitable valve configured to reversibly arrest fluid flow within a conduit. In one embodiment shown in FIG. 4, valve 300 can include a stepper valve 302. Stepper valve 302 can be actuated by gearing and is moveable between an open position, a partially closed position, and a fully closed position. In some embodiments, stepper valve 302 reversibly arrests fluid flow within a conduit by pinching the exterior of the conduit. In other embodiments, stepper valve 302 can be at least partially incorporated into the wall of the conduit such that opening and closing of stepper valve 302 pinches the conduit from within. Alternative embodiments of valve 300 are shown in FIG. 5, including solenoid valve 304, iris valve 306, and memory alloy valve 308. Solenoid valve 304 comprises a clamp actuated by a solenoid and can reversibly arrest fluid flow within a conduit by pinching or clamping the exterior of the conduit. Iris valve 306 comprises a plurality of interlocking wedges that can be actuated inwards to occlude a conduit lumen and can be actuated outwards to open a conduit lumen. Iris valve 306 can be actuated using any suitable mechanism, such as an outer or inner gear or an electromagnet. Memory alloy valve 308 comprises a plurality of curved rods constructed from a memory alloy set in a housing, wherein overlapping each of the curved rods occludes a central opening in the housing and spreading each of the curved rods apart from each other opens the central opening. Memory alloy valve 308 can be actuated mechanically, such that it retains an open or closed configuration at rest and can be closed or opened, respectively, upon application of a force. Memory alloy valve 308 can also be actuated thermally, such that it is switchable between an open or closed configuration by temperature. In various embodiments, valve 300 can include any suitable means of reversibly arresting fluid flow in a conduit, including diaphragm valves, balloon occluders, single or multi-leaflet valves, and the like. Additional prototype valves 300 are depicted in FIG. 22 through FIG. 26.

Figure 6:
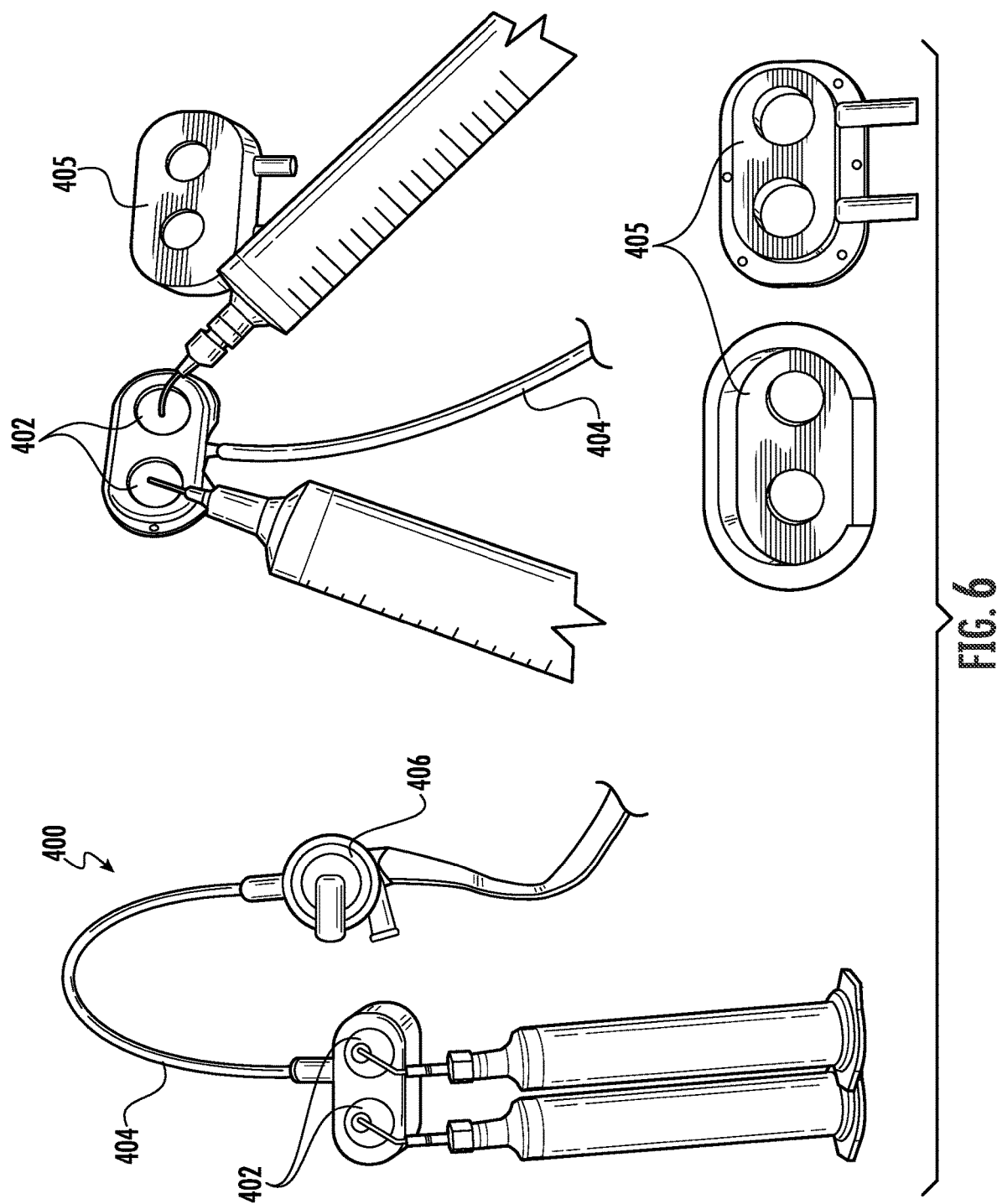
FIG. 6 depicts the cleaning port component of an exemplary intracardiac device.
Figure 7:
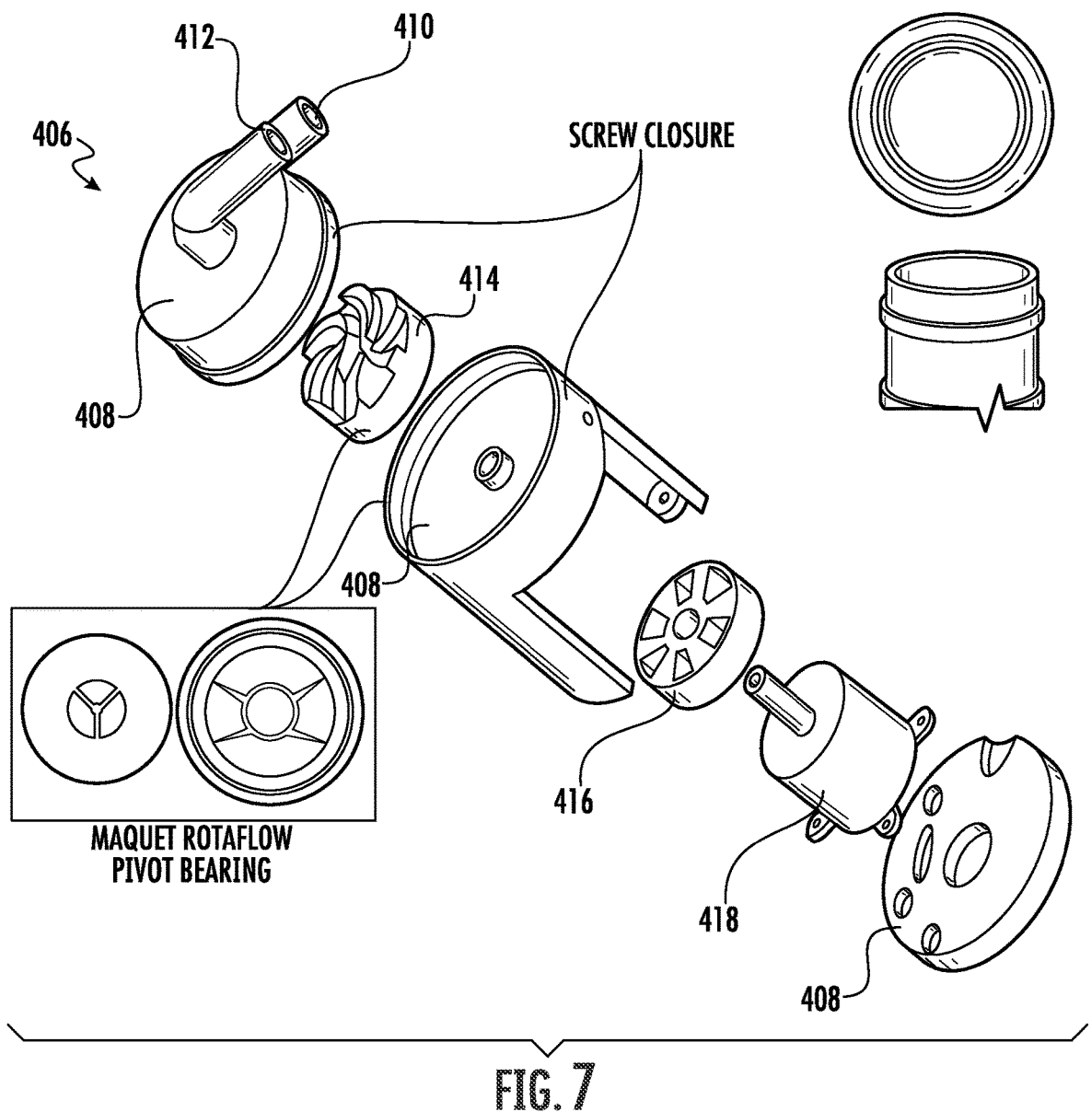
FIG. 7 depicts the centrifugal pump component compatible with the cleaning port component of an exemplary intracardiac device.
Figure 11:
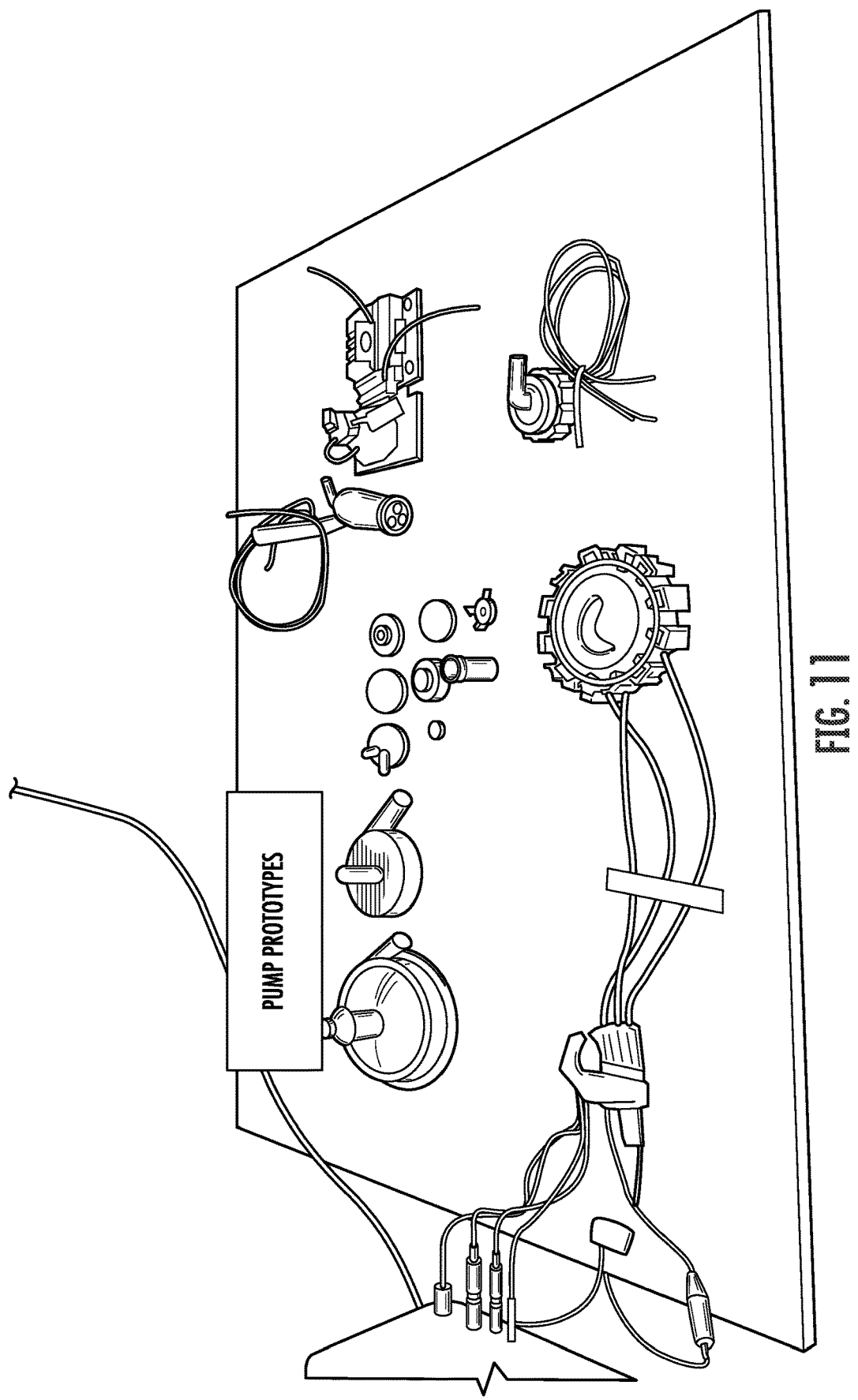
FIG. 11 depicts a collection of prototype centrifugal pumps compatible with the cleaning port component.
Figure 12:
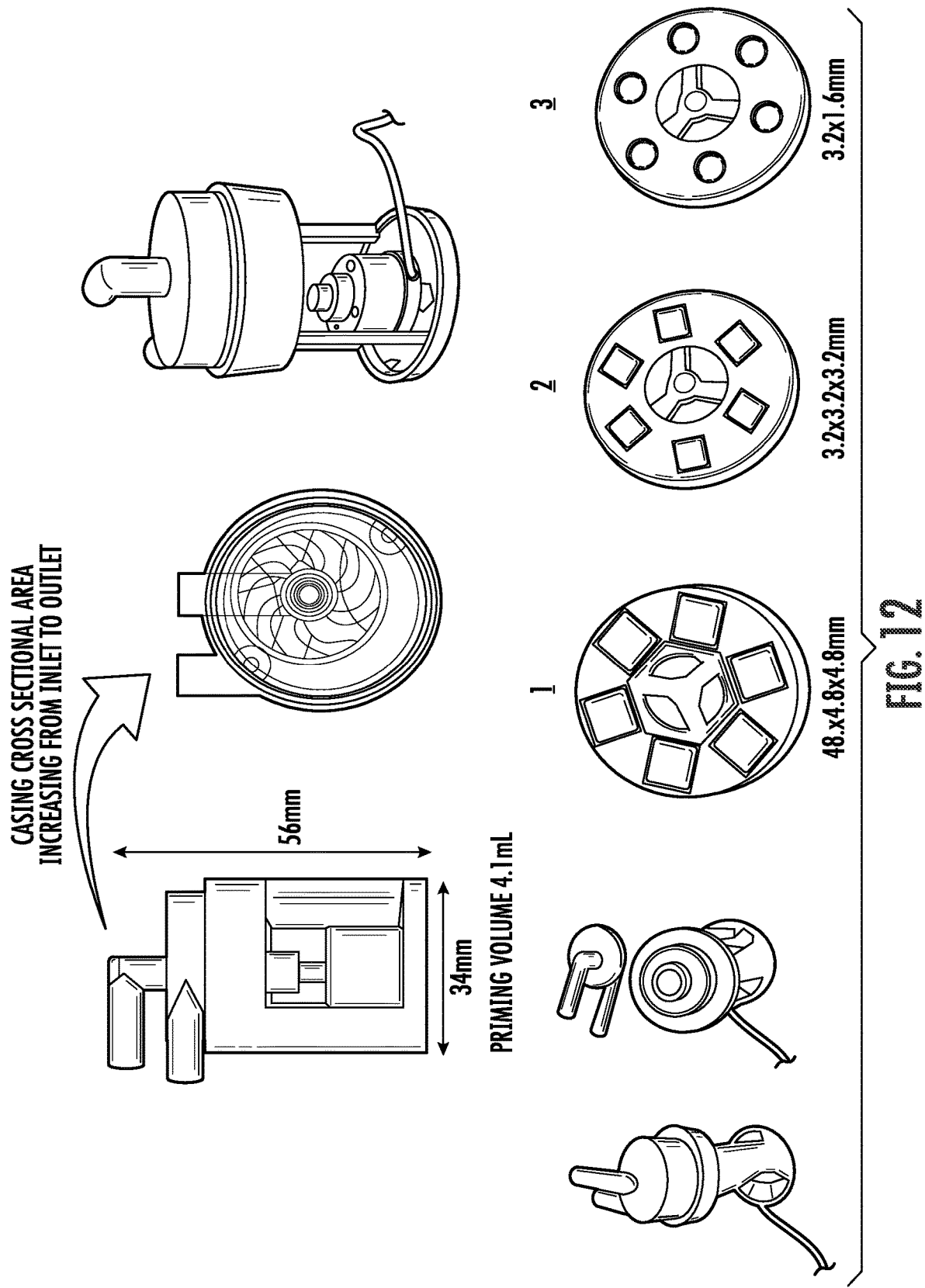
FIG. 12 depicts a prototype centrifugal pump with prototype magnetic couplings.
Figure 13:
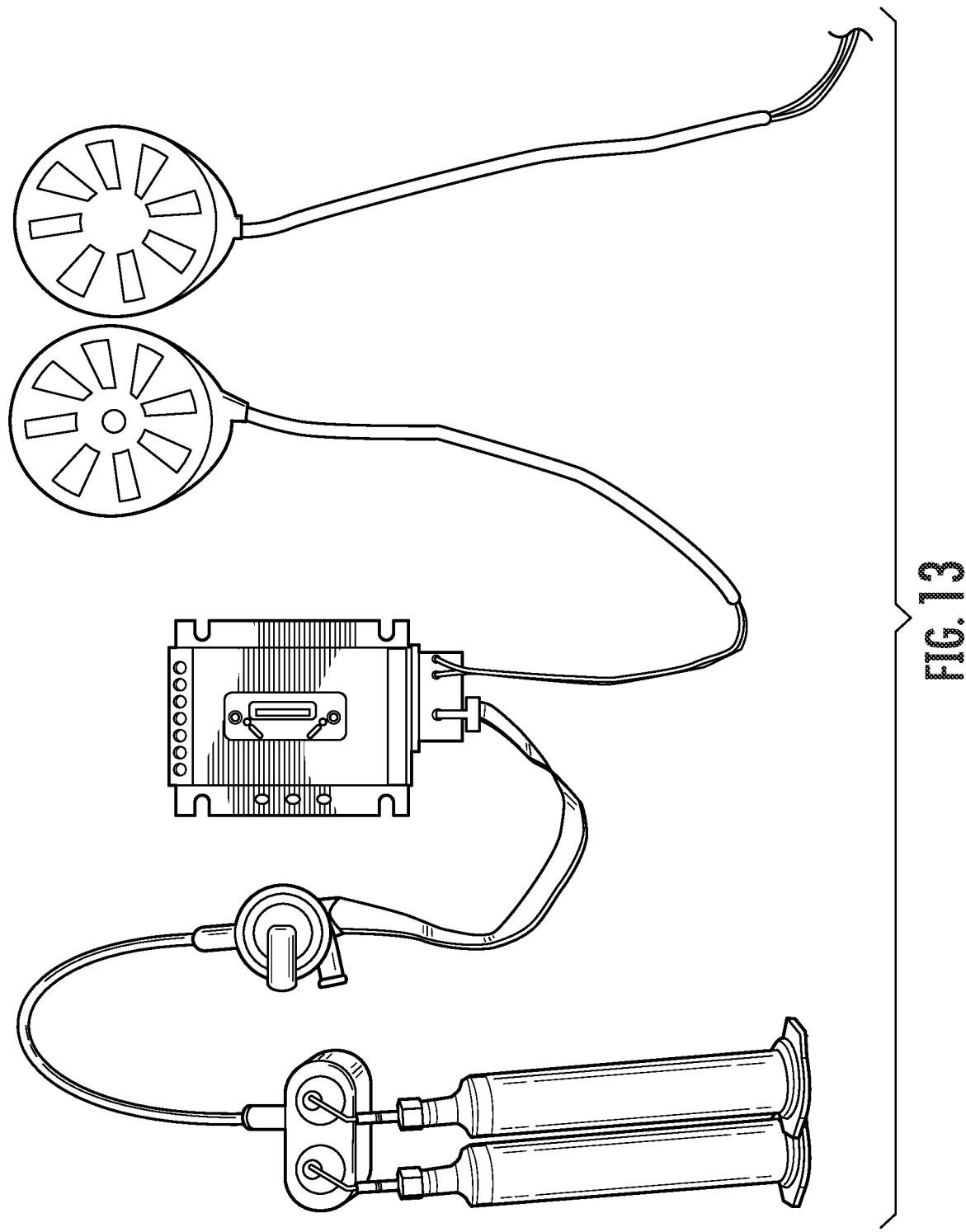
FIG. 13 depicts a prototype cleaning port and centrifugal pump connected to a controller and a wireless power system.

Referring now to FIG. 6, an exemplary cleaning system 400 is depicted. Cleaning system 400 comprises cleaning port 402, cleaning line 404, and centrifugal pump 406. Cleaning port 402 comprises at least one inlet and outlet fluidly connected to cleaning line 404 configured for the injection of a cleaning fluid and the extraction of spent cleaning fluid and debris. In certain embodiments, cleaning port 402 and cleaning line 404 can be used to inject a drug or therapeutic into an implanted device 100. Cleaning line 404 is fluidly connected to centrifugal pump 406, which is configured to rapidly circulate a cleaning fluid through an enclosed space, such as the interior of a sealed intracardiac device 100. Referring now to FIG. 7, an exemplary centrifugal pump 406 is depicted. Centrifugal pump 406 comprises housing 408 having an inflow port 410 and an outflow port 412 fluidly connectable to the interior of an enclosed space, such as the interior of a sealed intracardiac device 100. Centrifugal pump 406 circulates fluid between inflow port 410 and outflow port 412 using impeller 414. In some embodiments, impeller 414 is indirectly actuated by magnetic coupling 416 attached to motor 418, whereupon magnetic attraction of a rotating magnetic coupling 416 drives the rotation of impeller 414. Prototype cleaning systems 400 with centrifugal pump 406 designs are shown in FIG. 11 through FIG. 13.

In various embodiments, intracardiac device 100 can further comprise one or more modifications to enhance its performance. For example, in some embodiments device 100 can further include one or more instruments to monitor its function, such as an oxygen sensor, a pH sensor, a flow sensor, a temperature sensor, a heart rate monitor, and the like.

The several components of the present invention described above can be constructed using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

Method of Implantation

Figure 8:
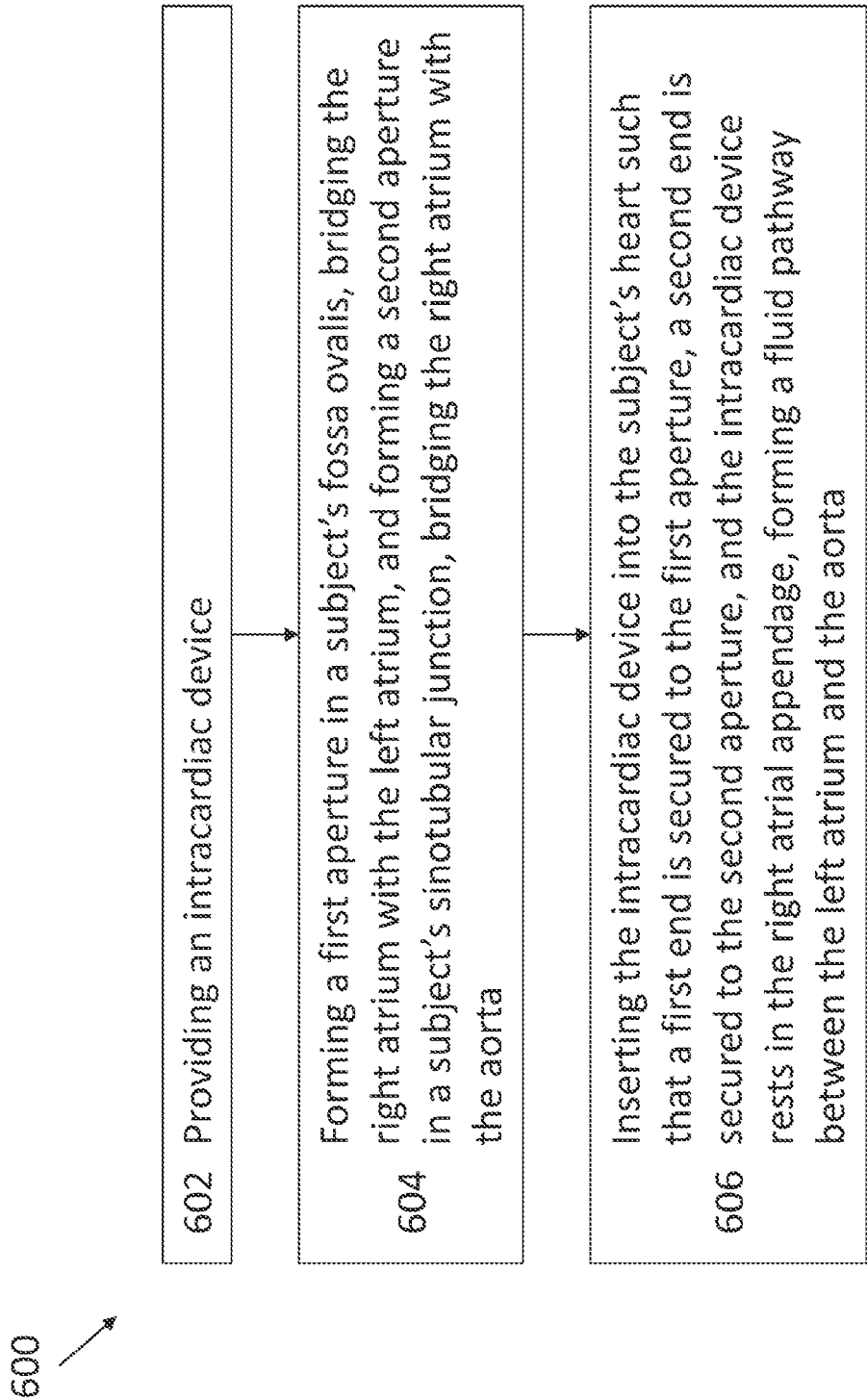
FIG. 8 depicts a flowchart of a method of inserting an exemplary intracardiac device.
Figures 9A, 9B, 9C:
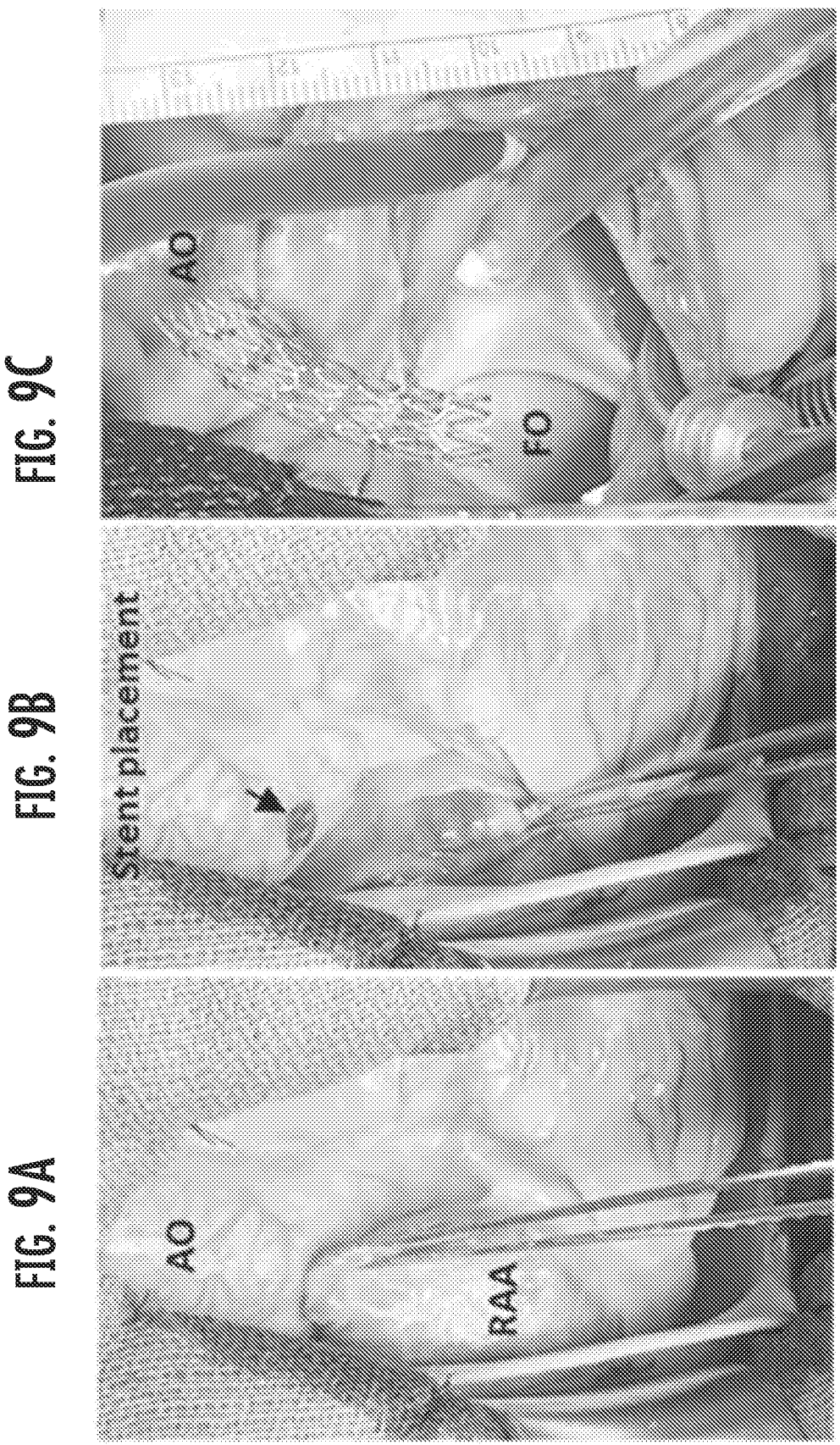
FIGS. 9A-9C illustrate the insertion and positioning of an exemplary intracardiac device.

The present invention further includes methods of inserting the intracardiac devices of the present invention. The method can be performed without open heart surgery, as the intracardiac devices are compatible with minimally invasive procedures. Referring now to FIG. 8, an exemplary method 600 is depicted. Method 600 begins with step 602, wherein an intracardiac device is provided. In step 604, a first aperture is formed in a subject's fossa ovalis to bridge the right atrium with the left atrium and a second aperture is formed in the subject's sinotubular junction to bridge the right atrium with the aorta. In step 606, the intracardiac device is inserted into the subject's heart such that a first end is secured to the first aperture, a second end is secured to the second aperture, and the intracardiac device rests in the right atrial appendage, forming a fluid pathway between the left atrium and the aorta. An exemplary placement is depicted in FIG. 9A through FIG. 9C, wherein a stent is shown approximating the intracardiac device within the right atrium (RAA) connecting the left atrium to the aorta (AO) by way of the fossa ovalis (FO).

The anatomical locations of the heart can be accessed using any suitable method. For example, the first aperture can be formed by the insertion of a guidewire in the femoral vein according to typical procedures, and guiding a puncture needle and dilator to the fossa ovalis. The second aperture can be formed by the insertion of a guidewire in the carotid artery according to typical procedures, and guiding a puncture needle and dilator to the sinotubular junction. It should be understood that any suitable approach commonly used in the art may be used, including but not limited to the internal jugular for the first aperture and transapical, transaortic, transfemoral, and trans-subclavian approaches for the second aperture. In some embodiments, the first aperture and the second aperture can both be formed by the same approach.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: Catheter Deliverable Intracardiac Co-Rhythmic, Isolable, Self-Maintenance Assist Device A trans-venous, trans-septal insertion with inflow from left atrium to ascending aorta & powered wirelessly while residing within the right atrial appendage was designed and tested.

A compact integrated maintenance system has two electronically controllable, external valves located at the inflow and outflow in a pericardium covered stent graft containing an axial pump. An integrated maintenance system to clean the intra-pump volume (~5 cc) was designed which can be transcutaneously accessed. Three different prototypes with different driving mechanism were considered: a solenoid linear actuator valve, an electromagnet-driven iris valve, and a gear-driven valve. Rapid prototyping technique using 3D printer was utilized to create both pump and valve prototypes. Performance of each prototype was evaluated using mock circulation loop equipped with flowmeter and pressure transducers.

A 31 Fr introducer sheath allowed the pericardium covered stent (with the pump) to be appropriately delivered via human sized internal jugular vein/femoral vein mannequin. The pump was designed with two different low-cost DC motors to make proper motor selection based on relations between power consumption and resulting performance. Pump performance was optimized for 2 Lt/min-4 Lt/min. For valve prototypes, solenoid valve and iris valve (which were both driven by electromagnetic forces) demonstrated that gear-driven valve showed better performance by properly closing the graft and making the flow near zero, showing promising potentials to minimize the size with compactly arranged gear design. A 0.1 mg/ml tPA solution with total volume of 15 cc was adequate to clean all the debris within the pump interior microscopically. An integrated maintenance system with controller, backup battery (two hours) and receiving coil for TETS transmission worked without issues in-vitro.

Example 2: An Endovascular, Totally Implantable Cardiac Support Device for Early Class III Heart Failure The following study presents an endovascular, totally implantable, on demand cardiac support device with technological sophistication to eliminate common adverse events associated with traditional LVADs.

Figure 14:
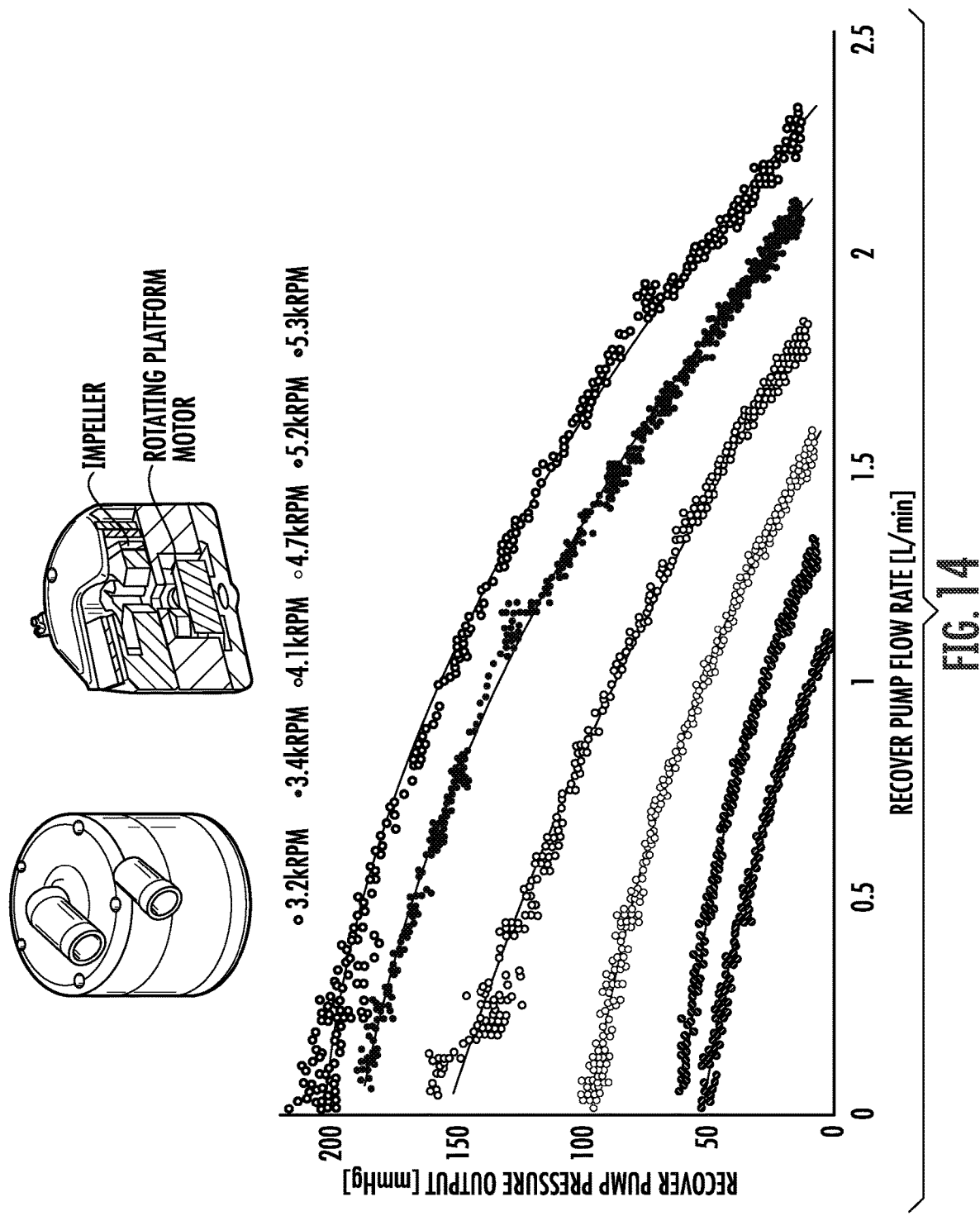
FIG. 14 depicts the experimental results of testing the performance of a prototype centrifugal pump.
Figure 15:
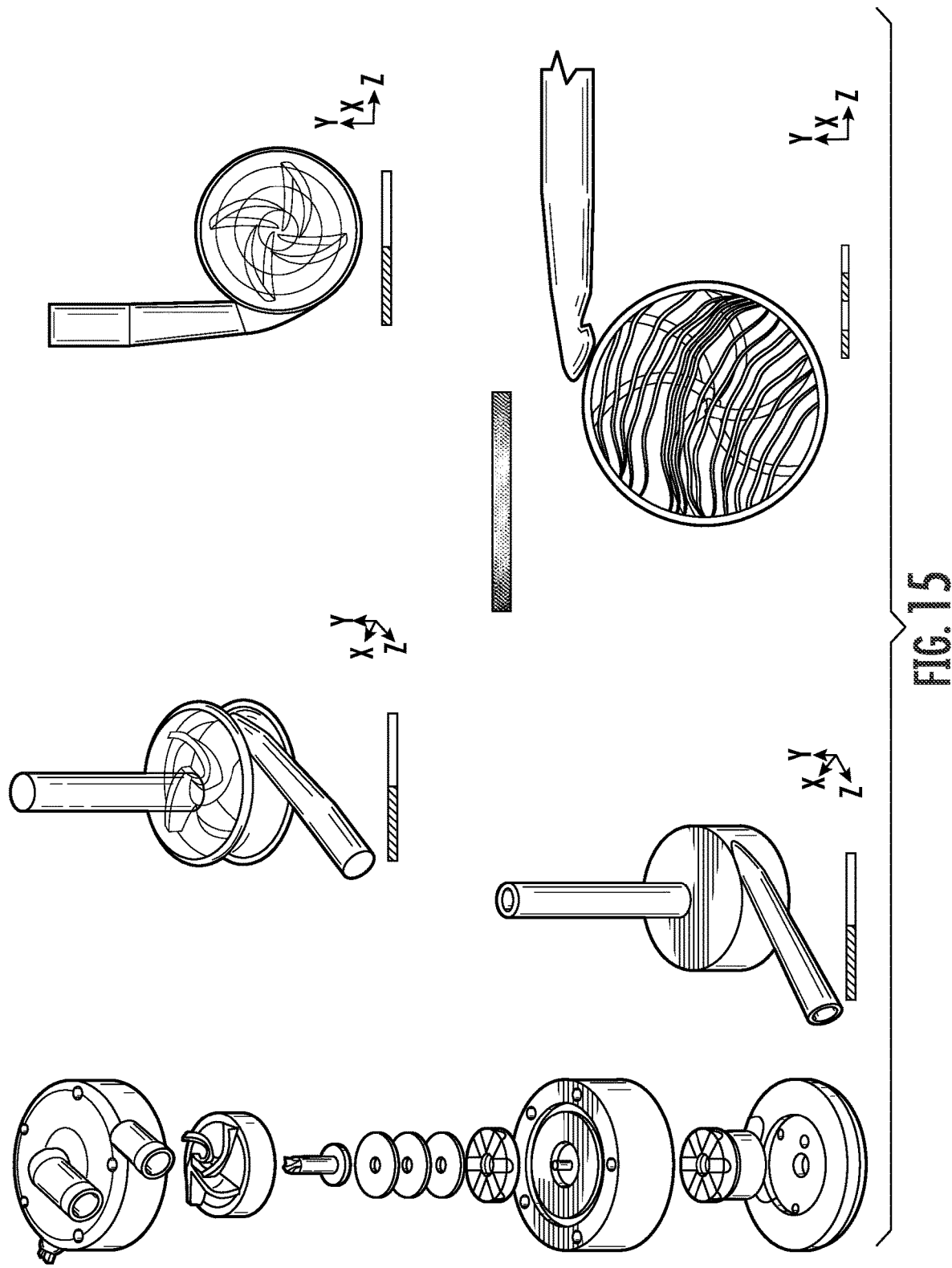
FIG. 15 depicts the experimental results of modeling fluid flow in a prototype centrifugal pump.
Figure 16:
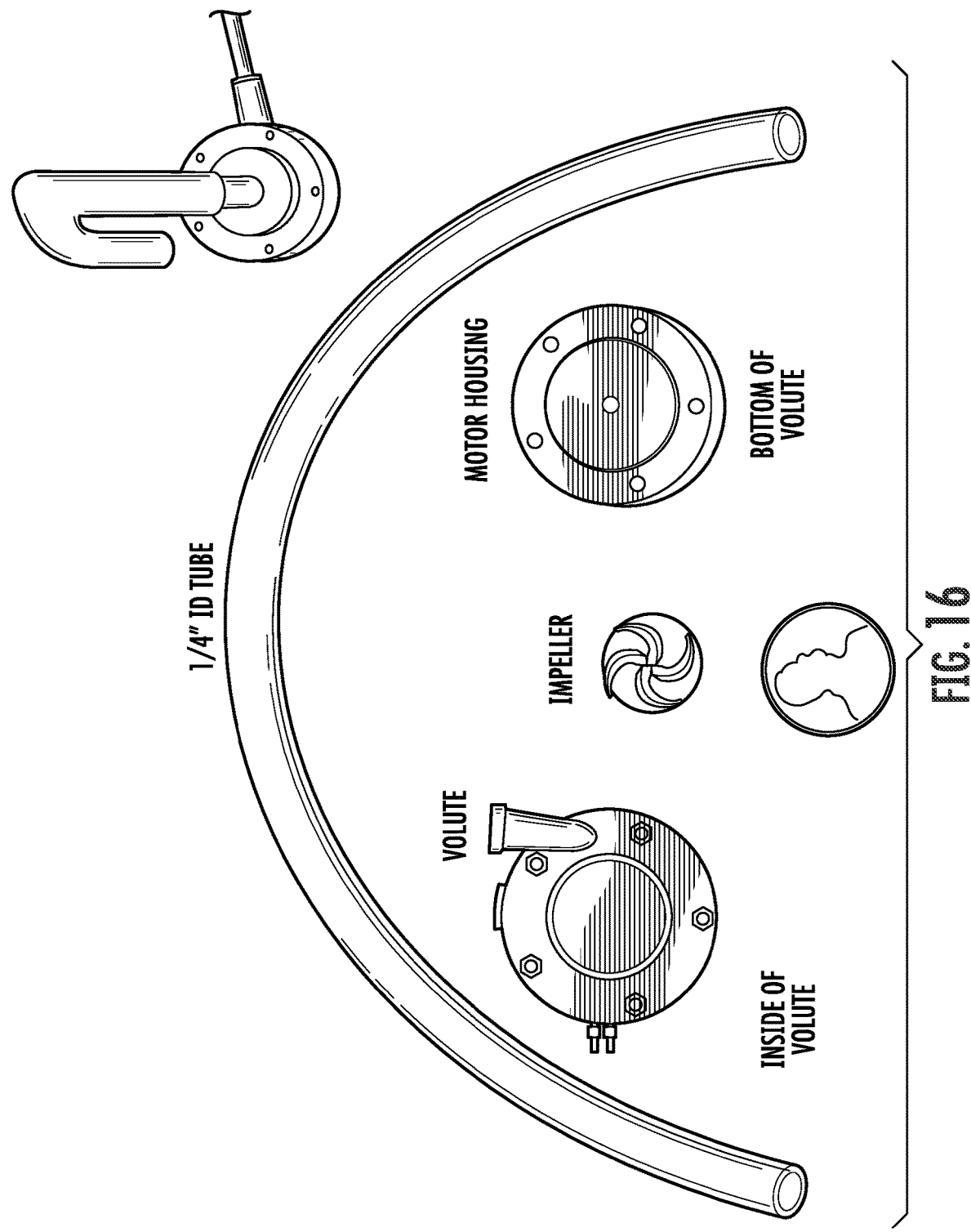
FIG. 16 depicts the construction of a prototype centrifugal pump.
Figure 17:
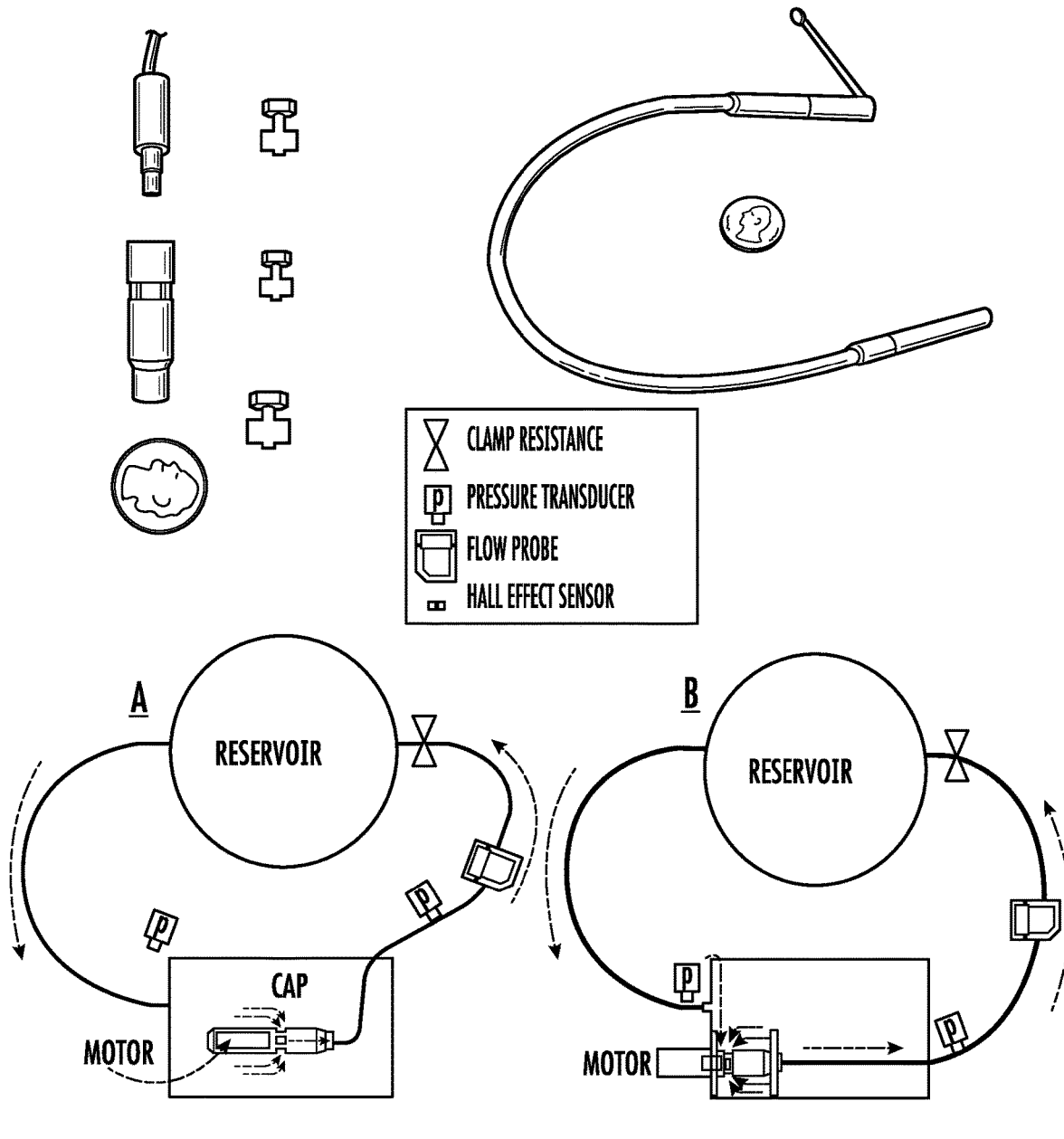
FIG. 17 depicts the construction and setup of a prototype axial pump compatible with the intracardiac device.
Figure 18:
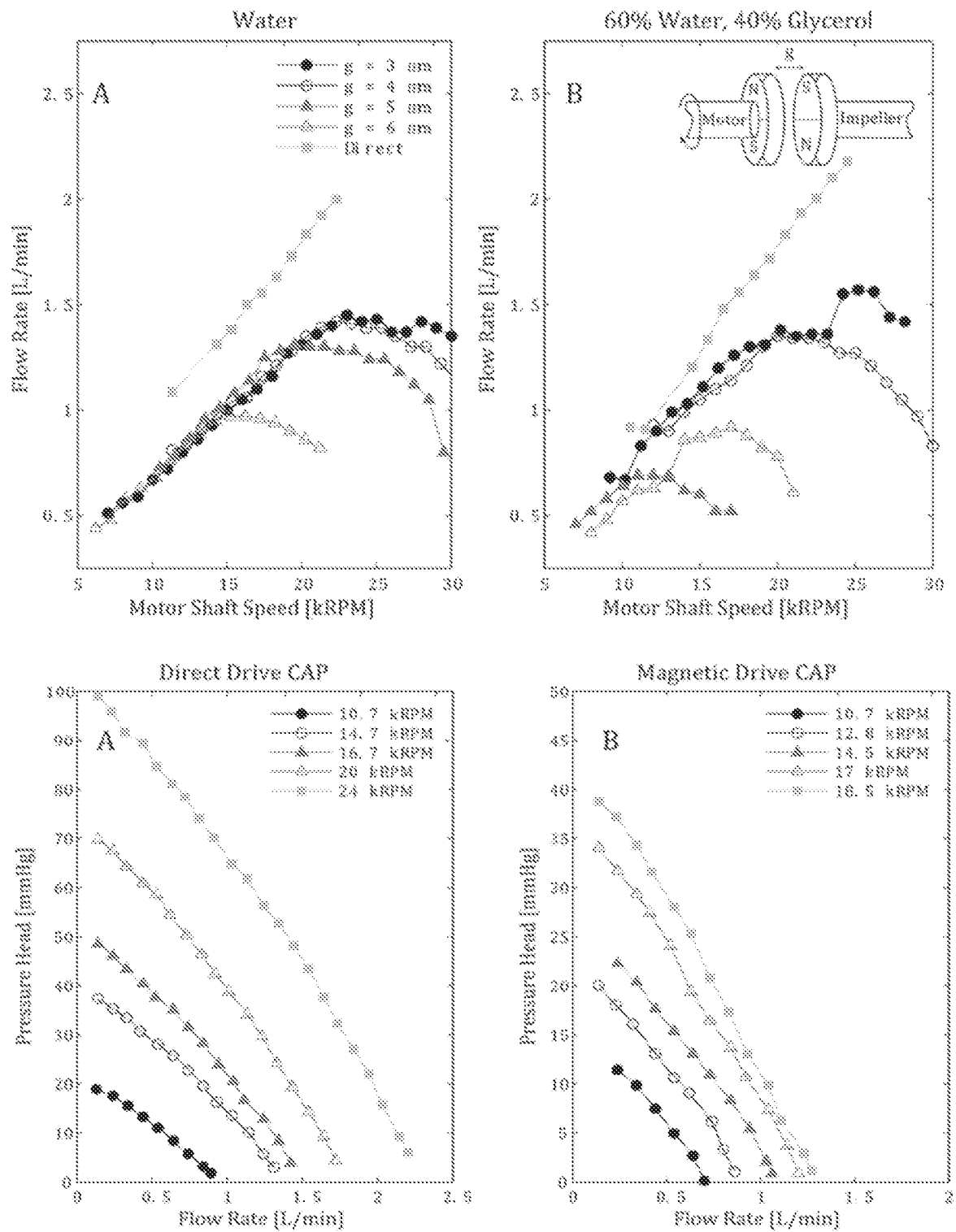
FIG. 18 depicts the experimental results of testing the performance of prototype axial pumps under varied operational conditions.
Figure 19:
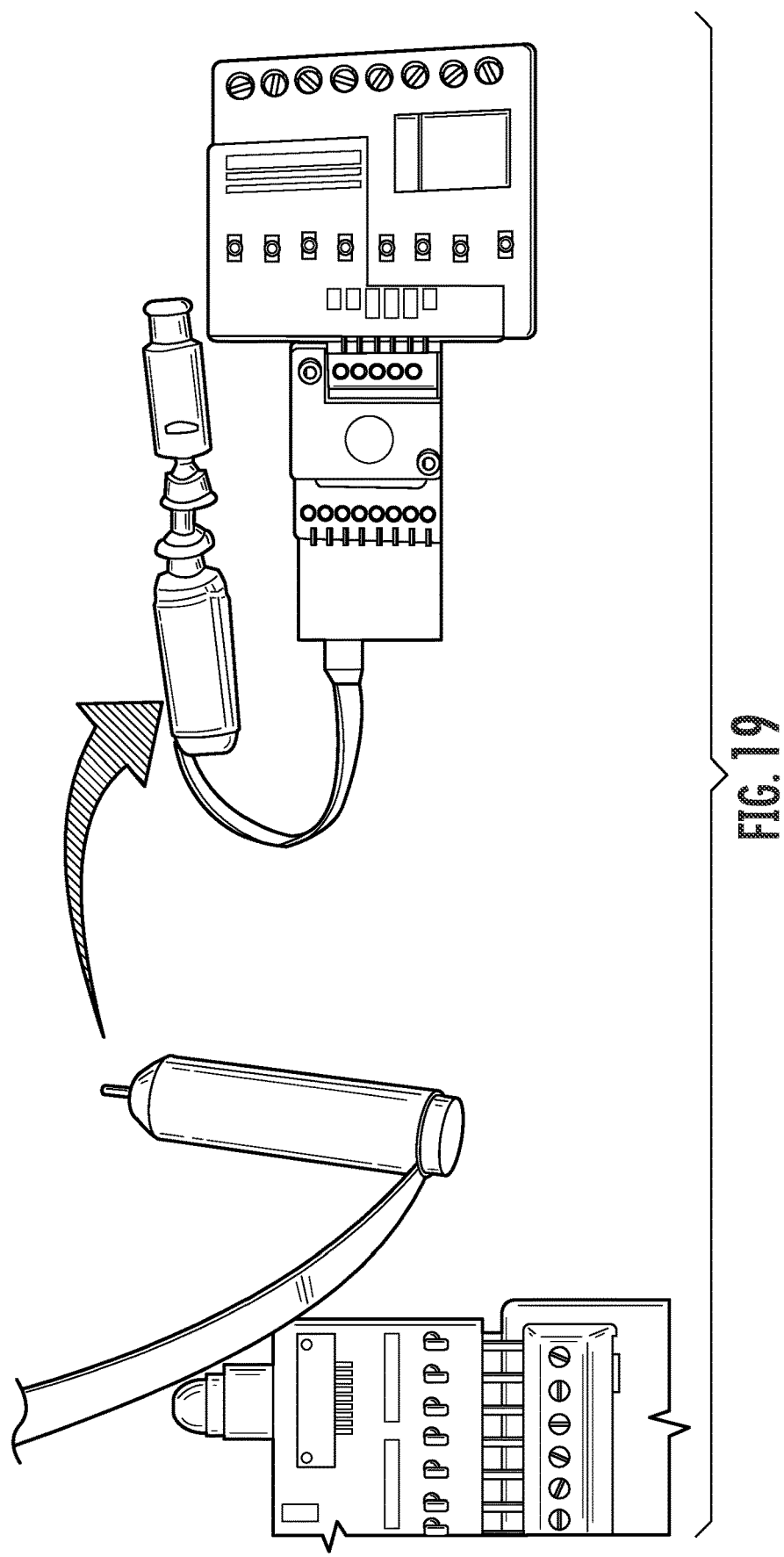
FIG. 19 depicts a prototype axial pump connected to a controller.
Figure 20:
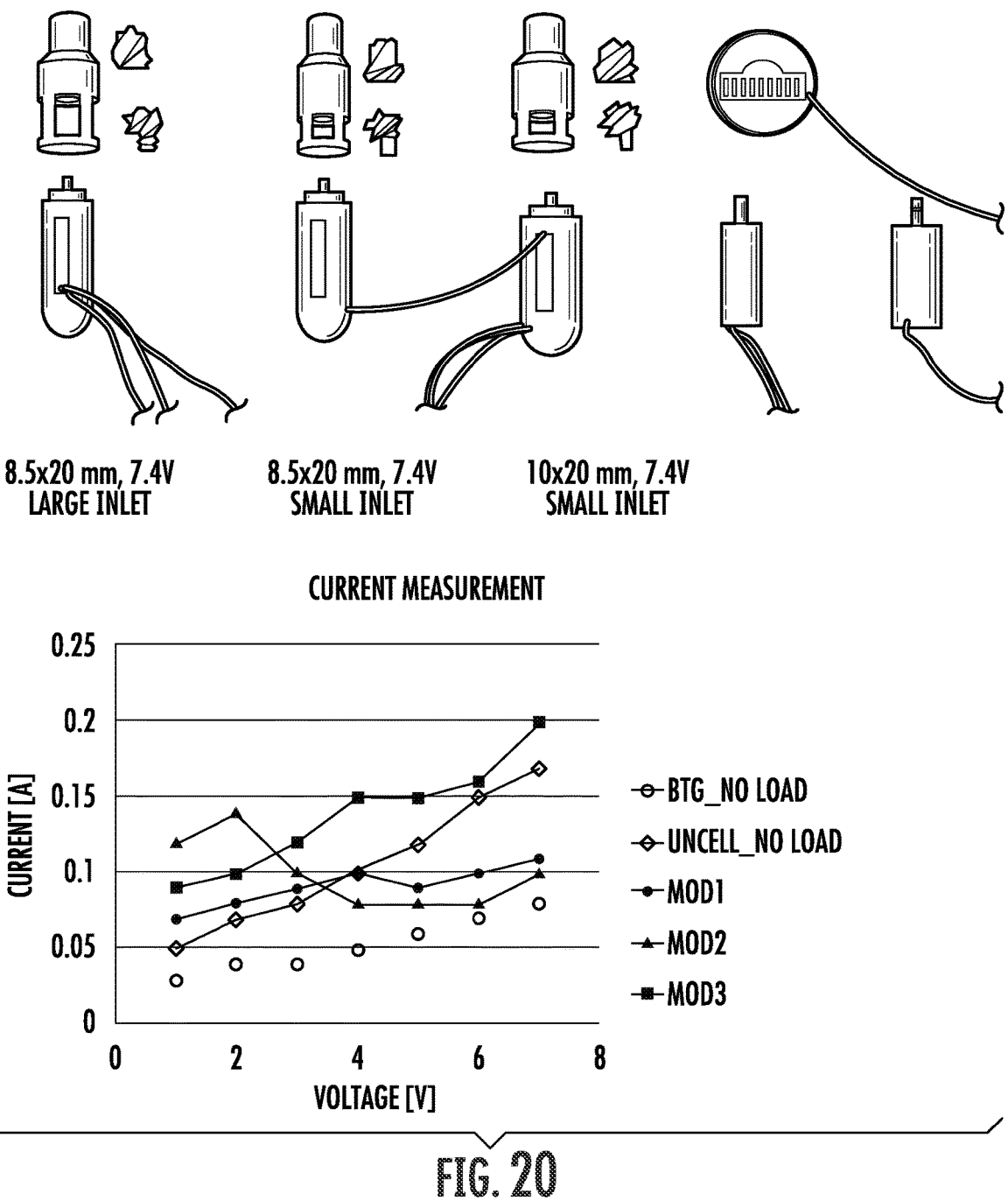
FIG. 20 depicts the experimental results of testing the power requirements of differently dimensioned prototype axial pumps.
Figure 22:
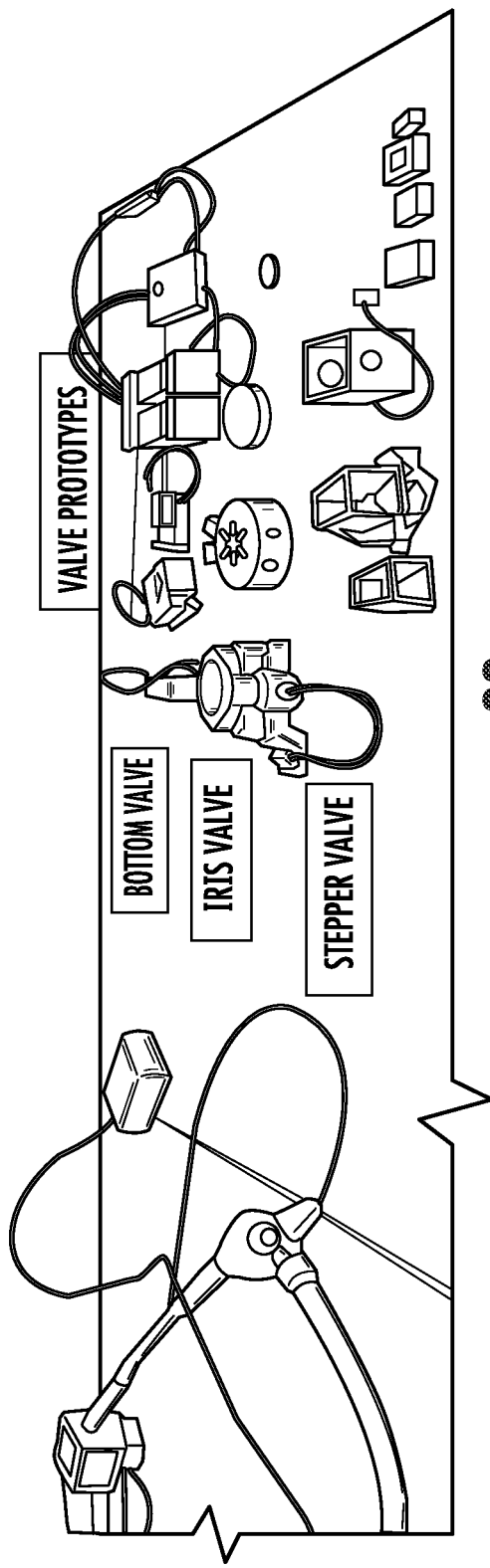
FIG. 22 depicts a collection of prototype valves compatible with the intracardiac device.
Figure 23:
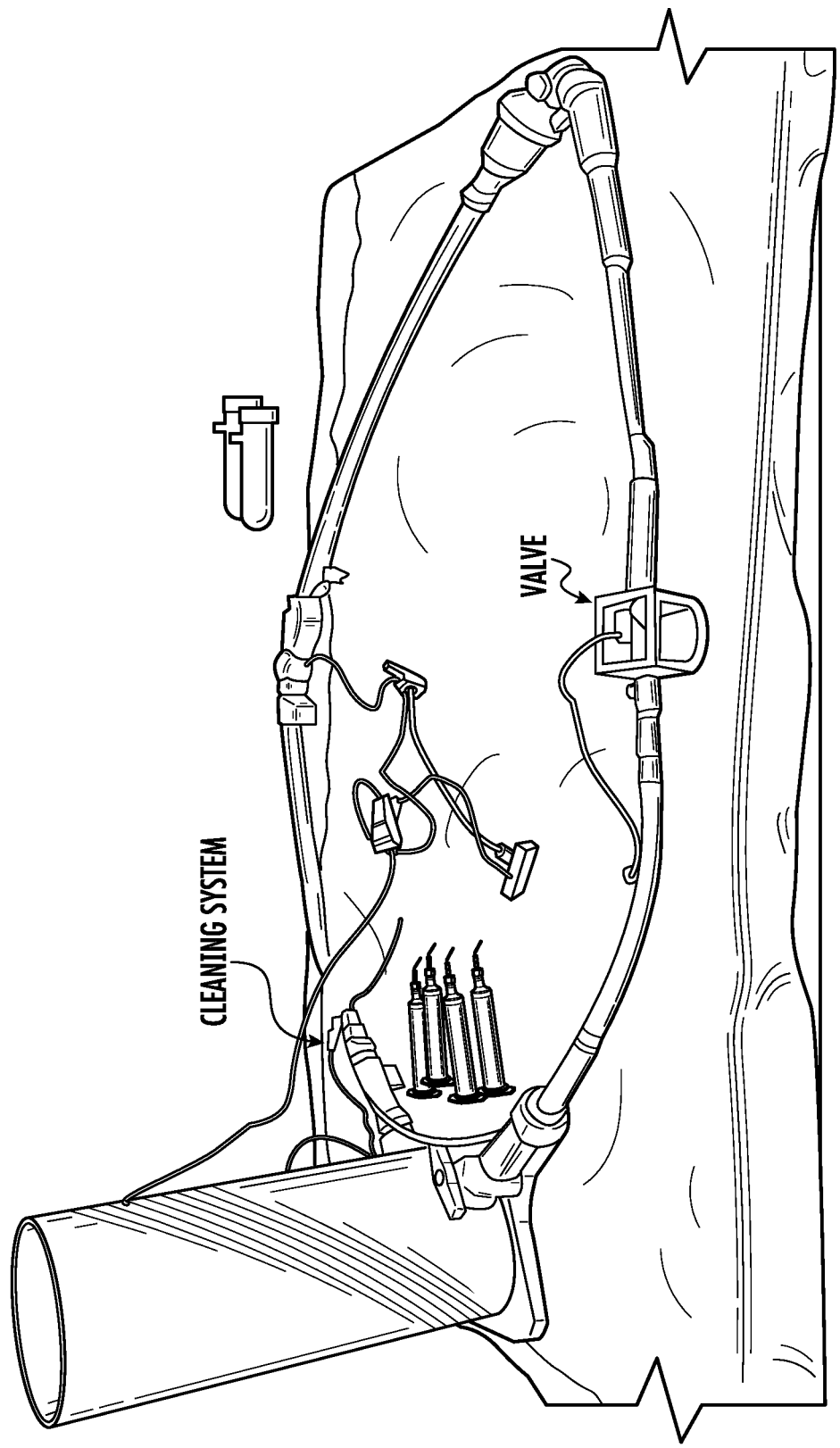
FIG. 23 depicts an experimental setup combining a prototype cleaning port component with a valve component.
Figure 24:
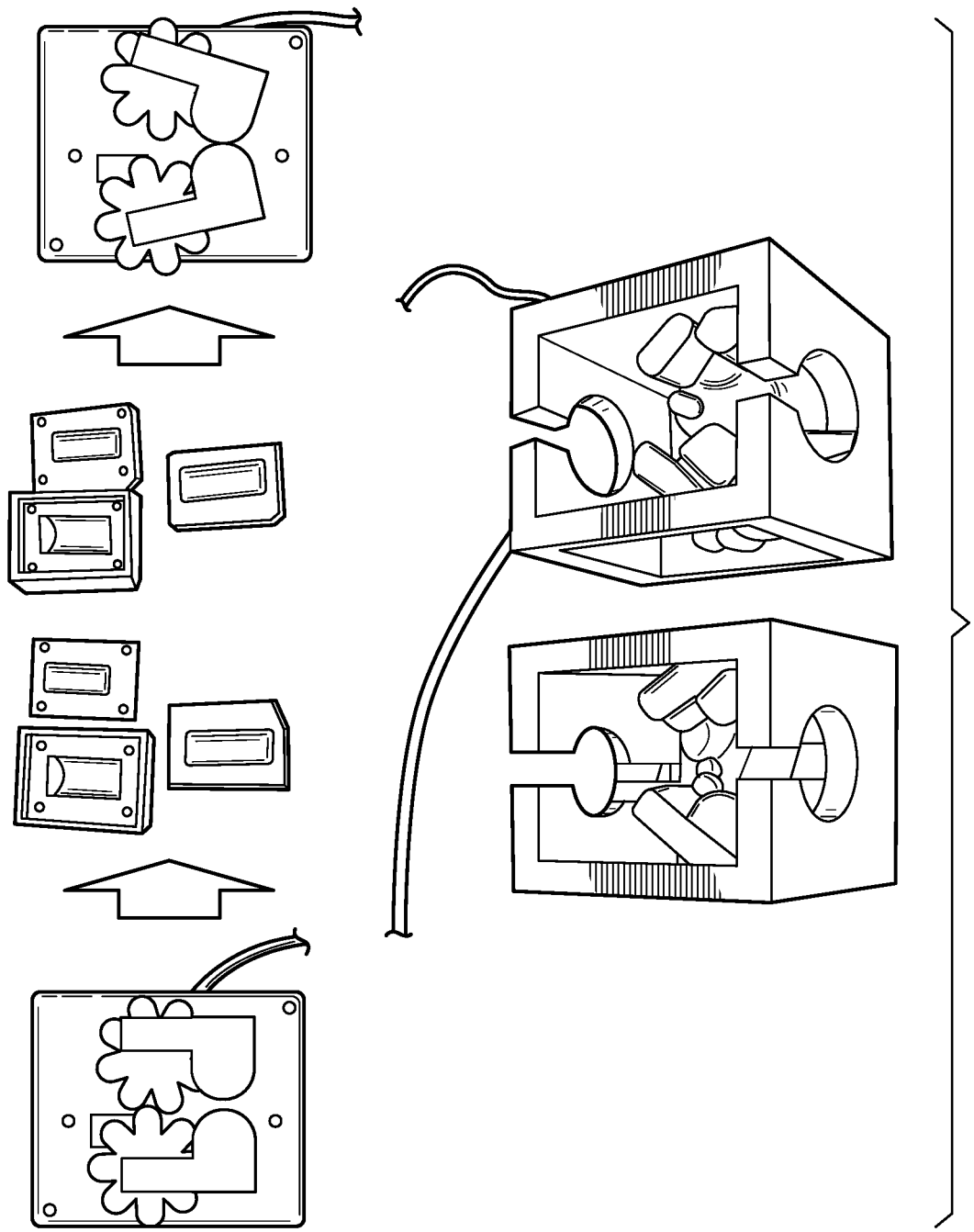
FIG. 24 depicts a prototype stepper valve having silicone coverings.
Figure 25:
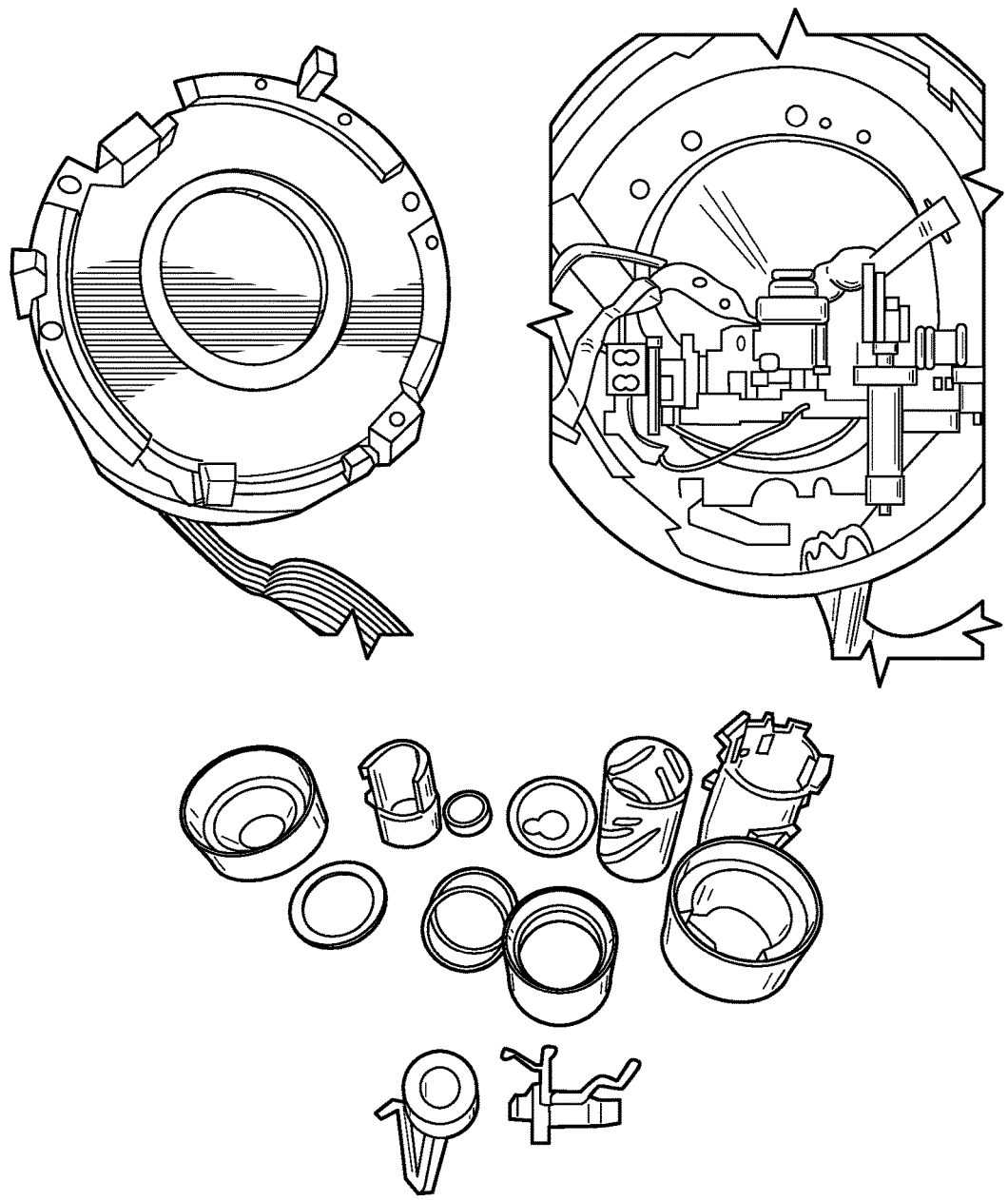
FIG. 25 depicts a prototype gear driven iris valve.
Figure 27A:
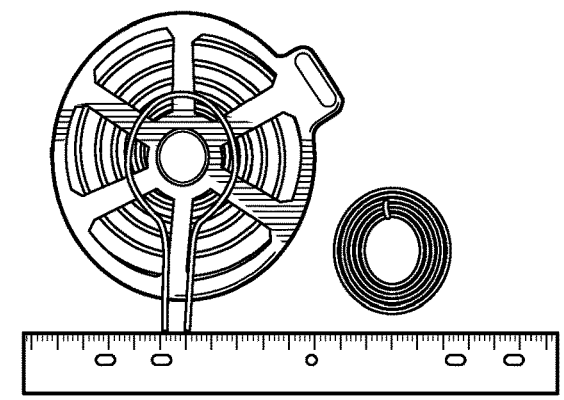
FIG. 27A through FIG. 27C depicts a prototype free range electrical energy delivery system.
Figure 27B:
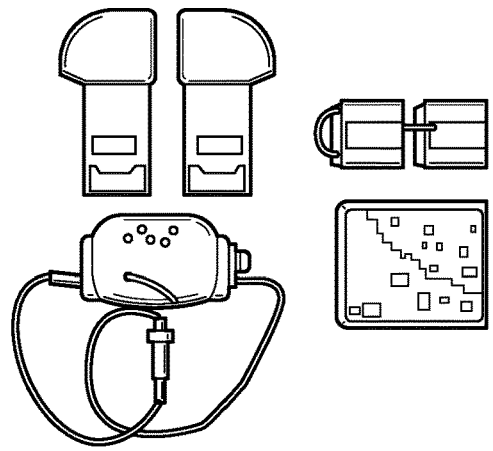
Figure 27C:
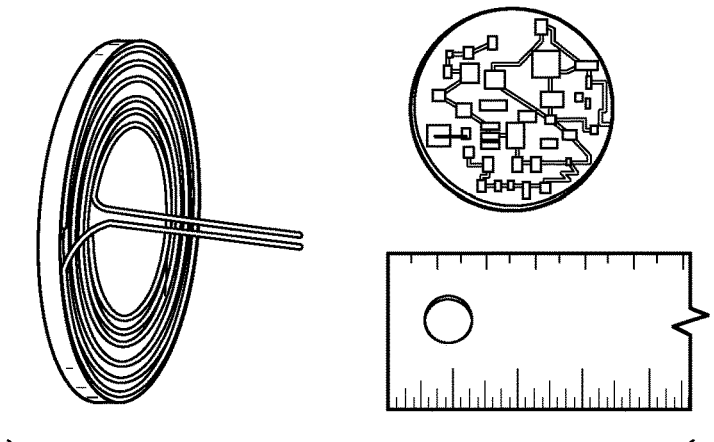
Figure 28:
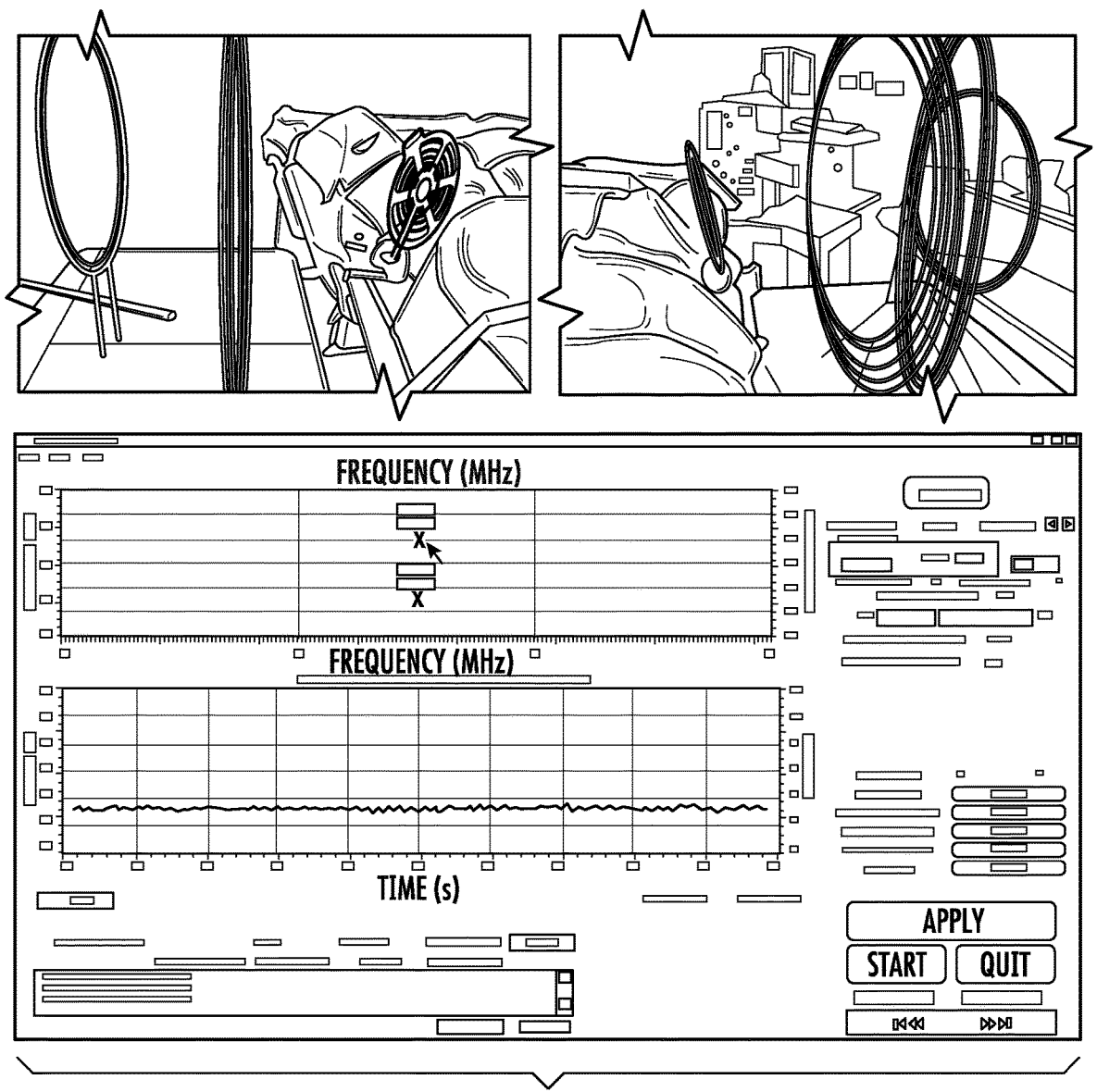
FIG. 28 depicts the experimental setup of a prototype wireless power system in an animal model.
Figure 29A:
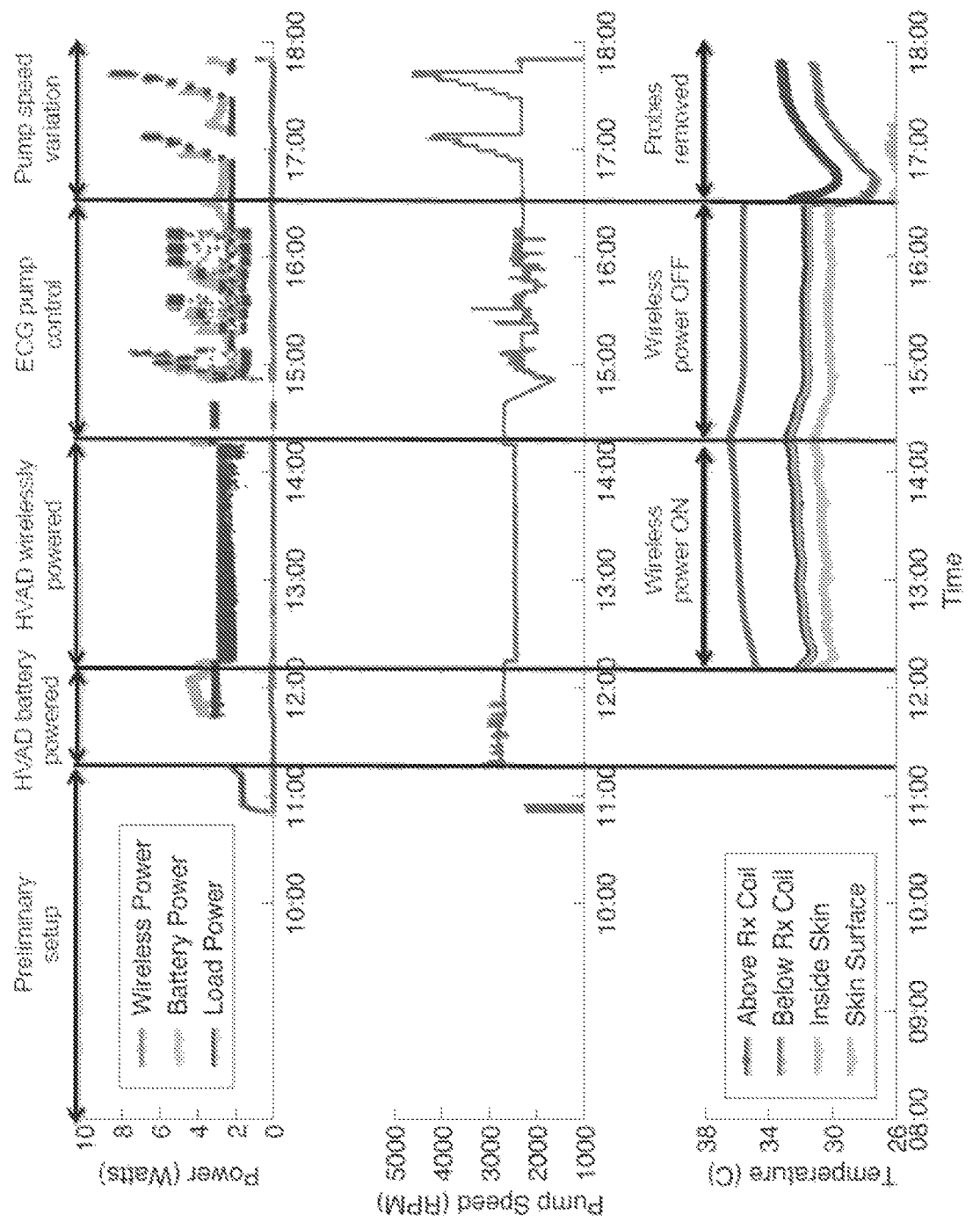
FIG. 29A and FIG. 29B depict the experimental results of a prototype wireless power system in an animal model.
Figure 29B:
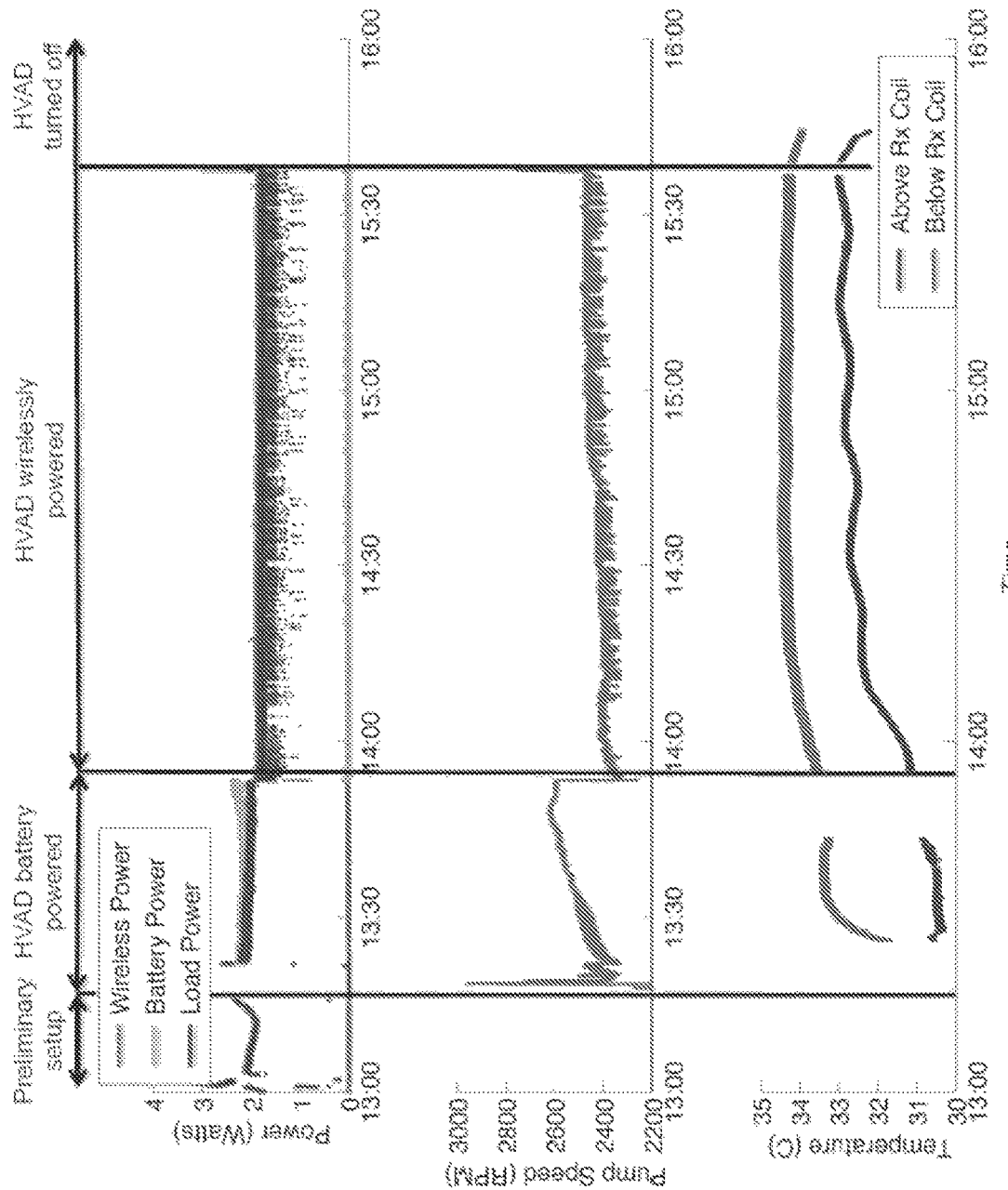
Figure 30:
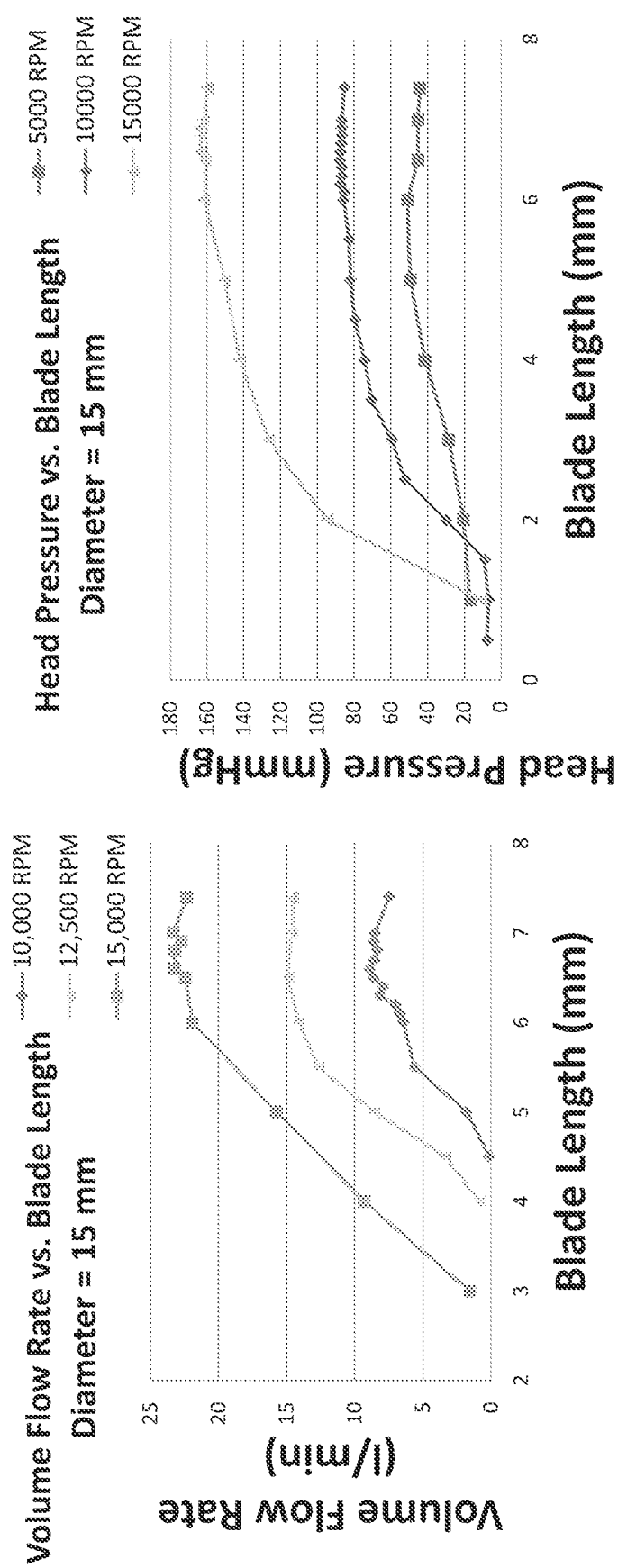
FIG. 30 depicts the experimental results of different blade lengths on the flow rate and head pressure of a fluid actuator.
Figure 31:
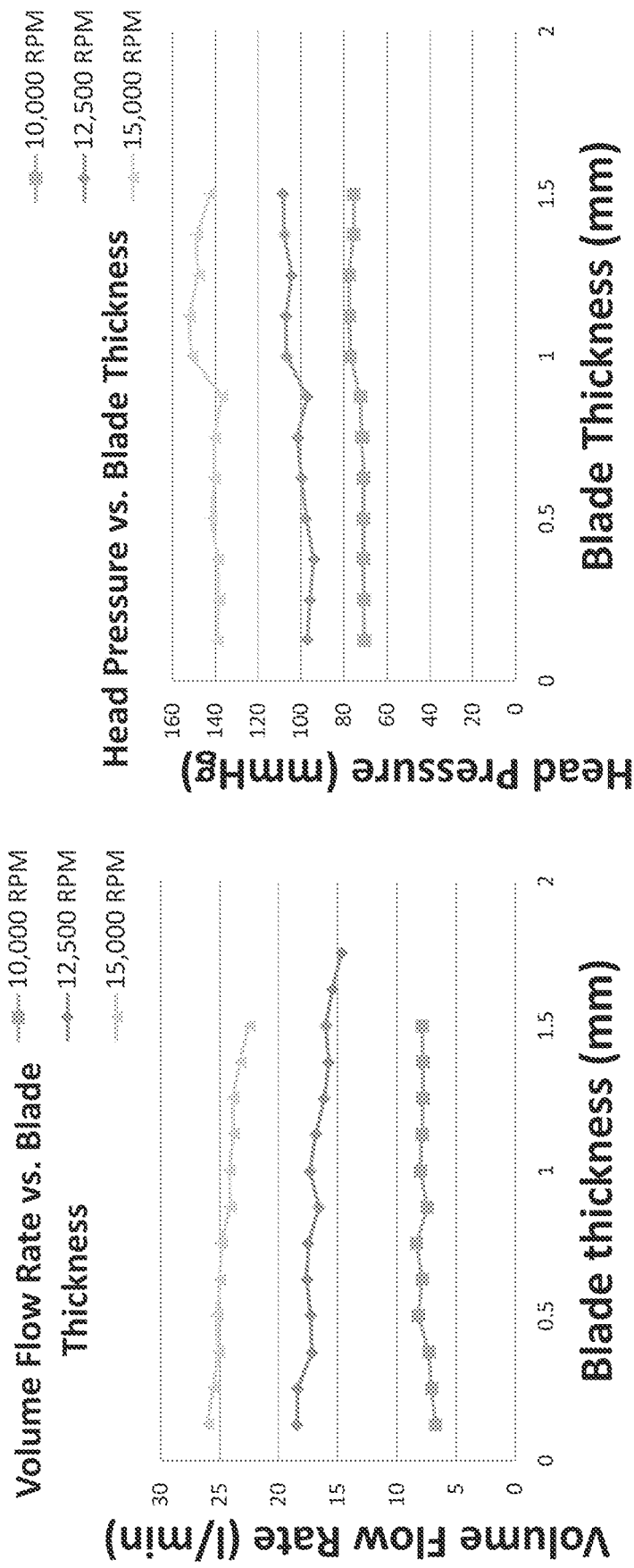
FIG. 31 depicts the experimental results of different blade thicknesses on the flow rate and head pressure of a fluid actuator.
Figure 32:
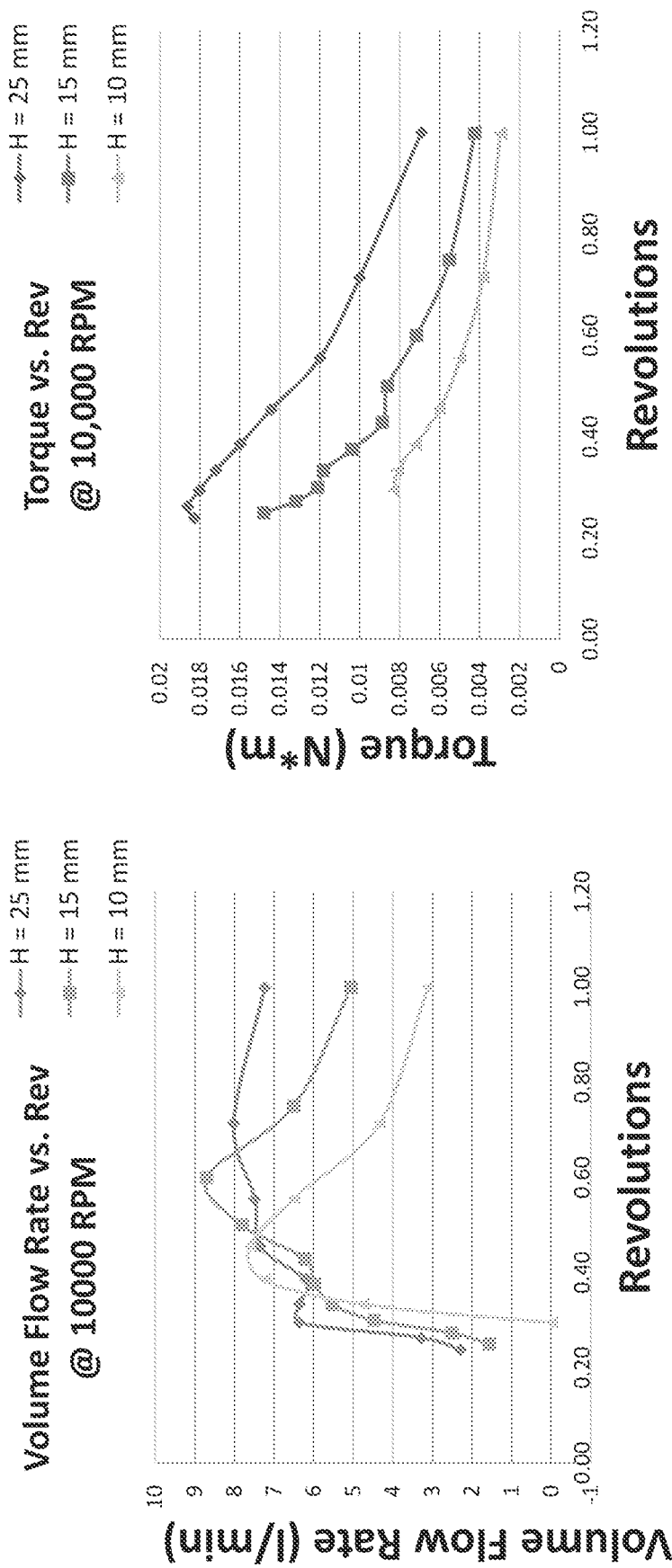
FIG. 32 depicts the experimental results of different blade pitch on the flow rate and torque of a fluid actuator.
Figure 33:
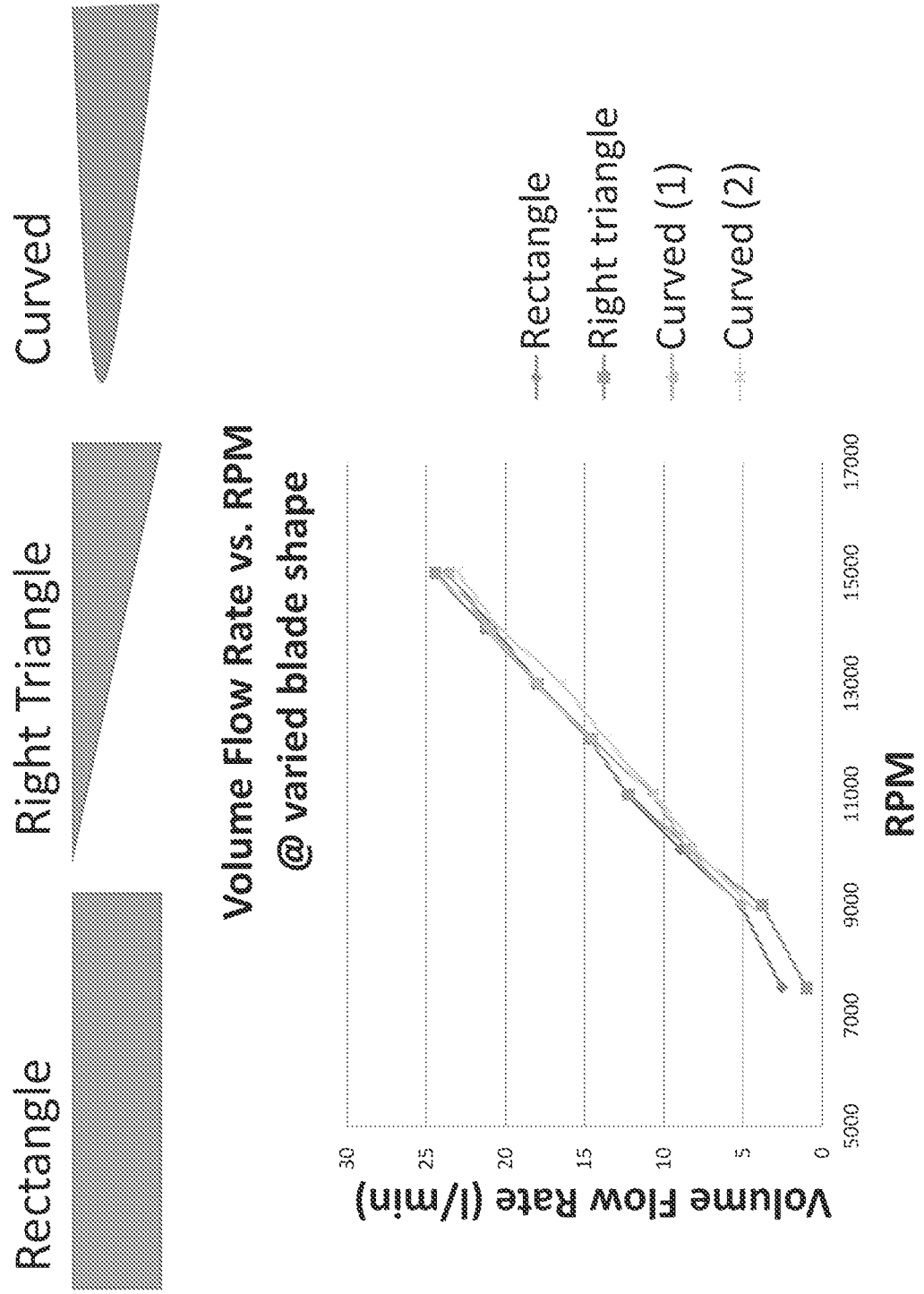
FIG. 33 depicts the experimental results of different blade shapes on the flow rate of a fluid actuator.
Figure 34:
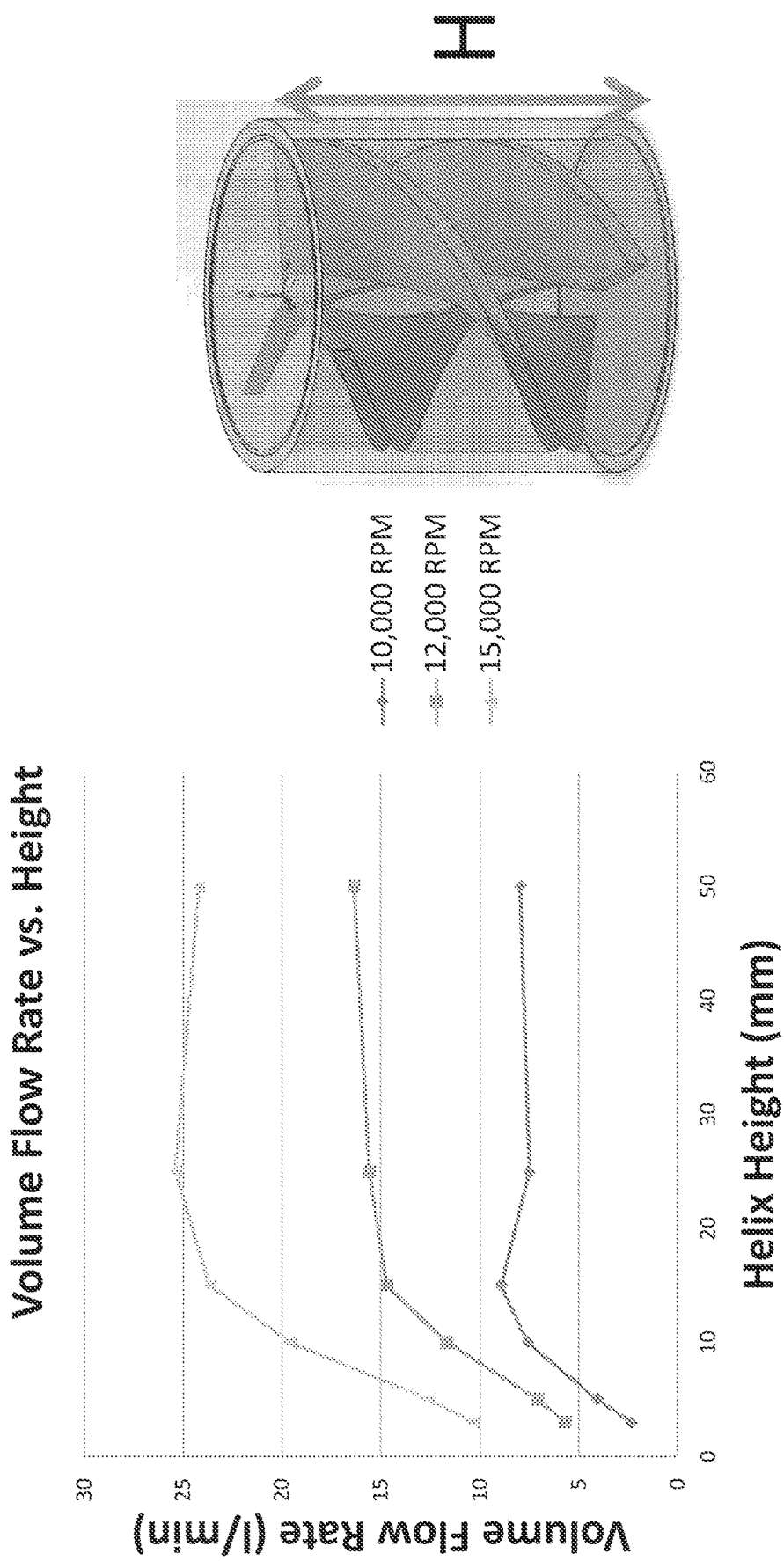
FIG. 34 depicts the experimental results of different fluid actuator heights on flow rate.
Figure 35:
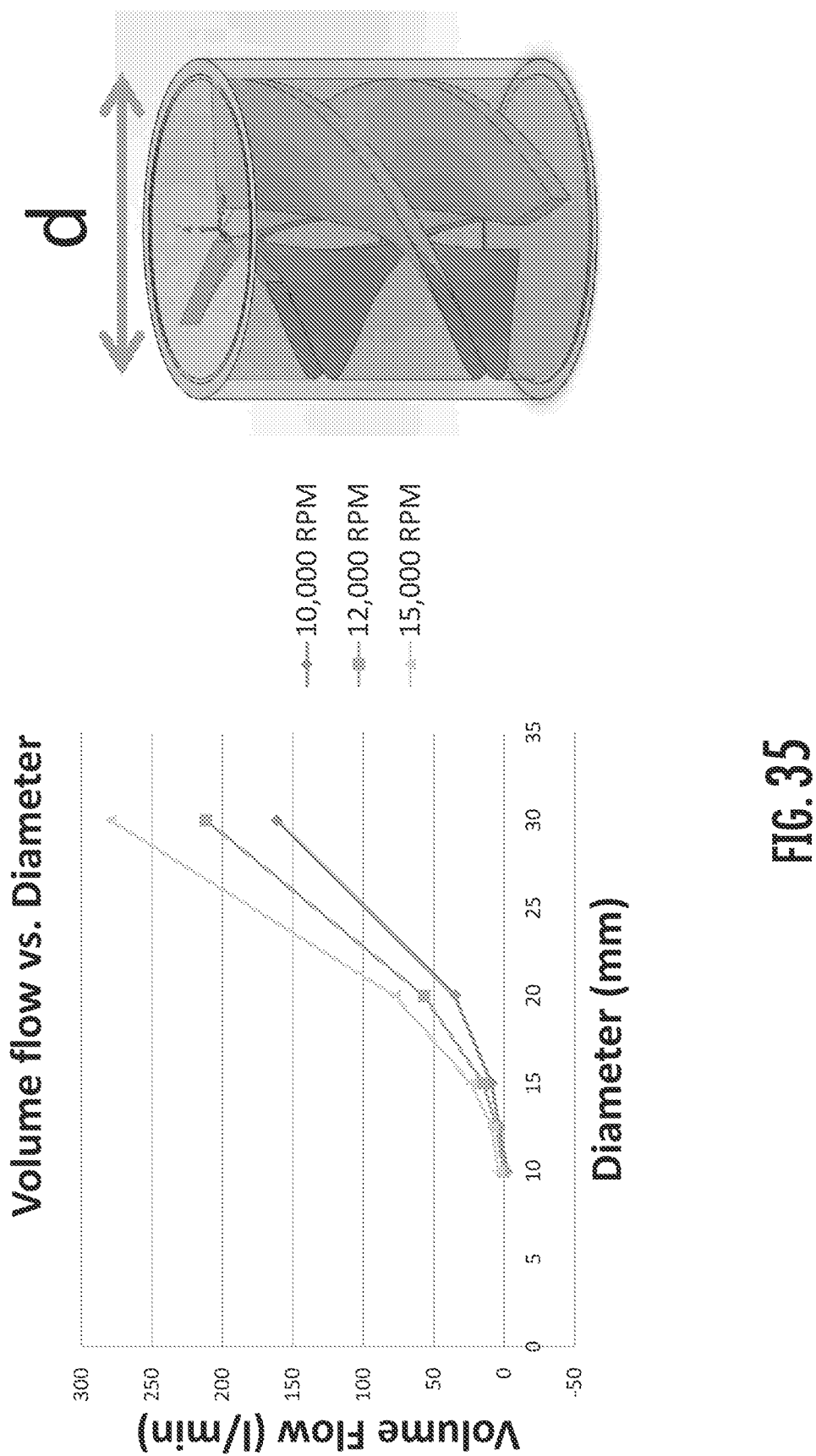
FIG. 35 depicts the experimental results of different fluid actuator diameters on flow rate.
Figure 36:
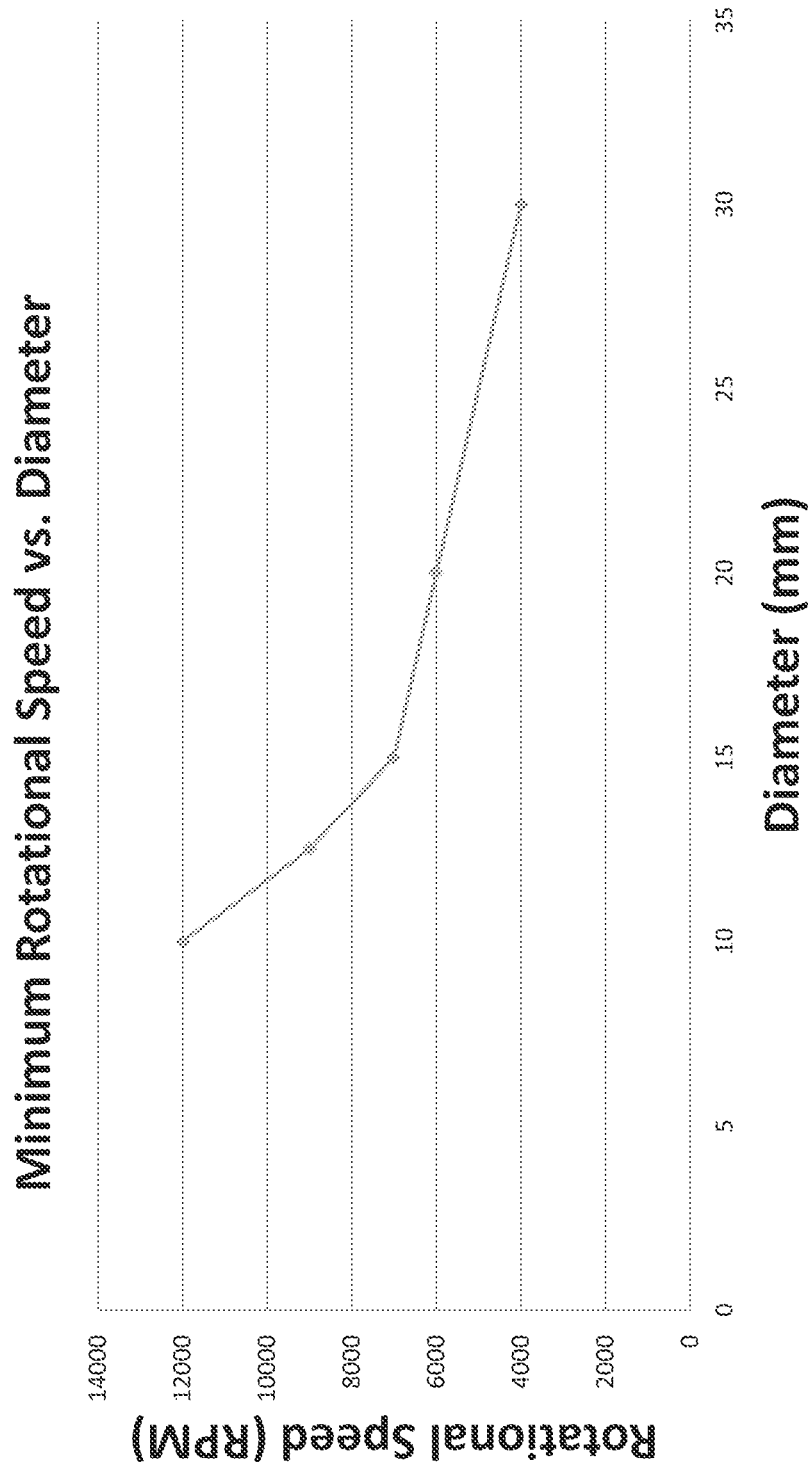
FIG. 36 depicts the experimental results of fluid actuator diameter and the minimum rotational speeds required to prevent back flow.
Figure 37:
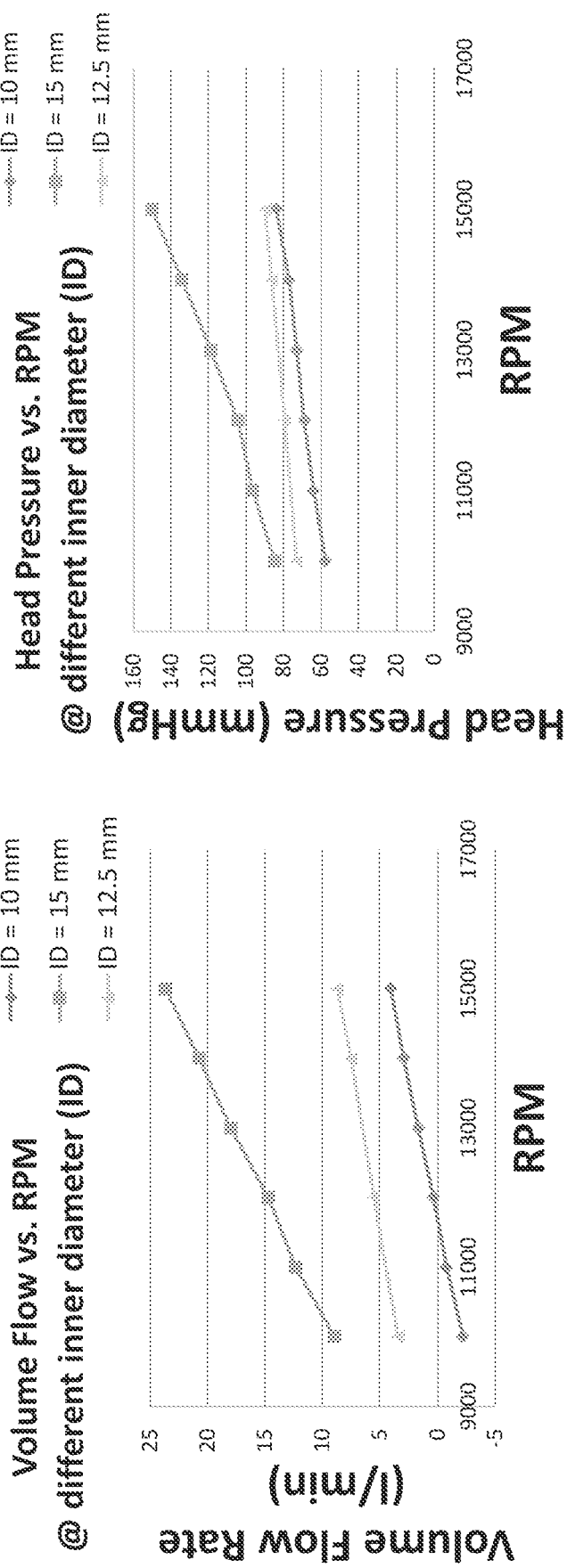
FIG. 37 depicts the experimental results of different fluid actuator diameters on flow rate and head pressure.
Figure 38:
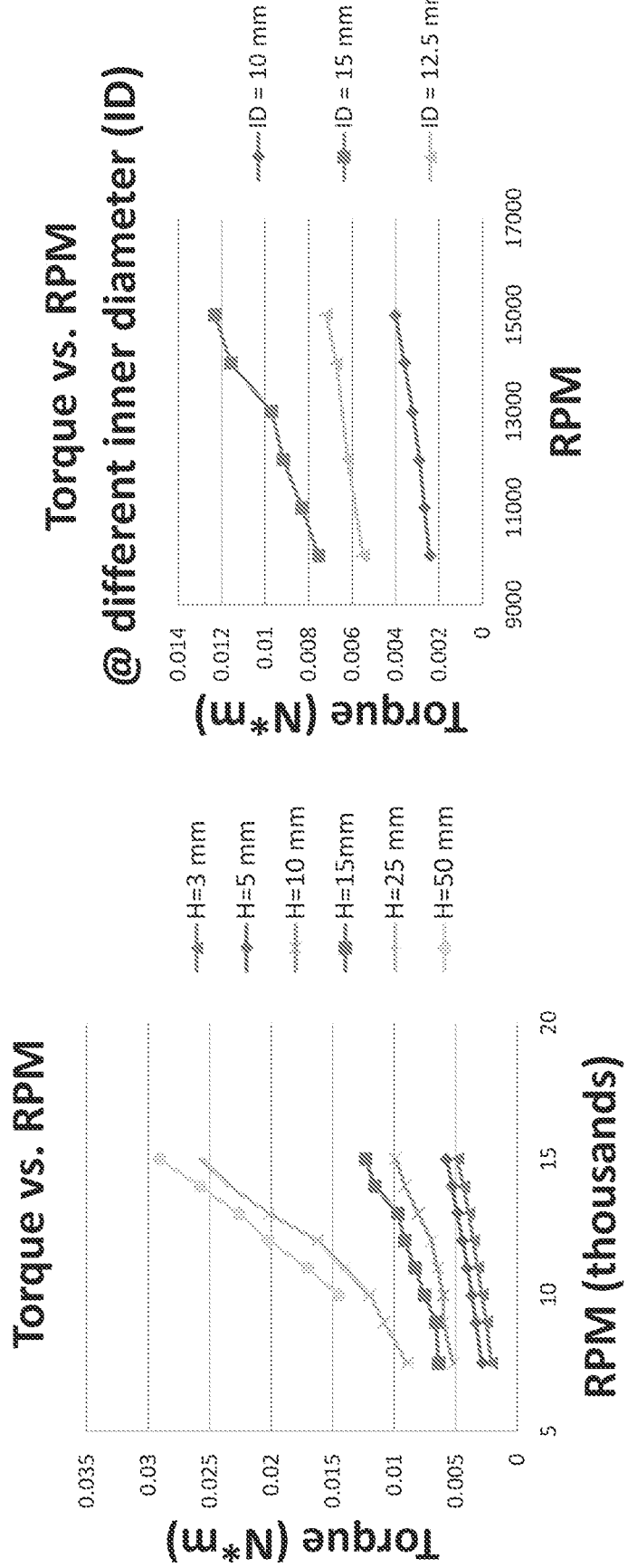
FIG. 38 depicts the experimental results of different fluid actuator heights and diameters on torque.
Figure 39:
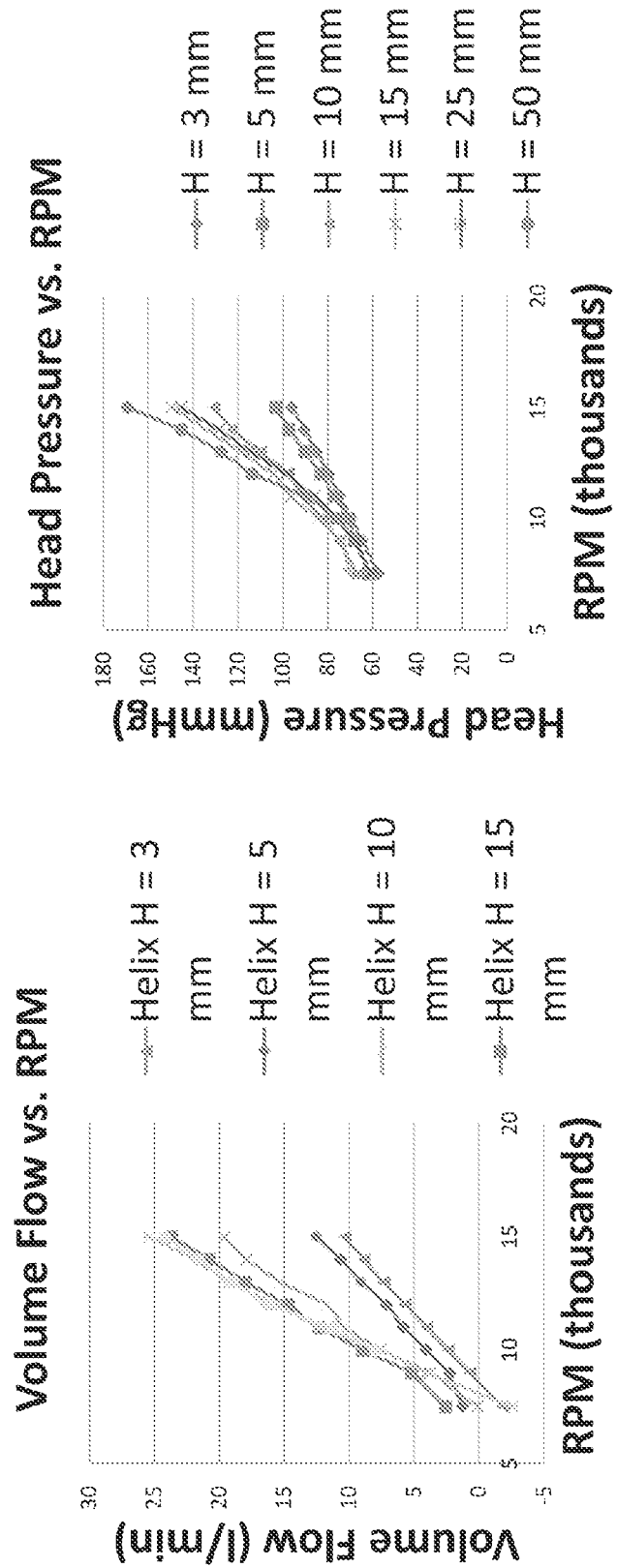
FIG. 39 depicts the experimental results of different fluid actuator heights on flow rate and head pressure.
Figure 40:
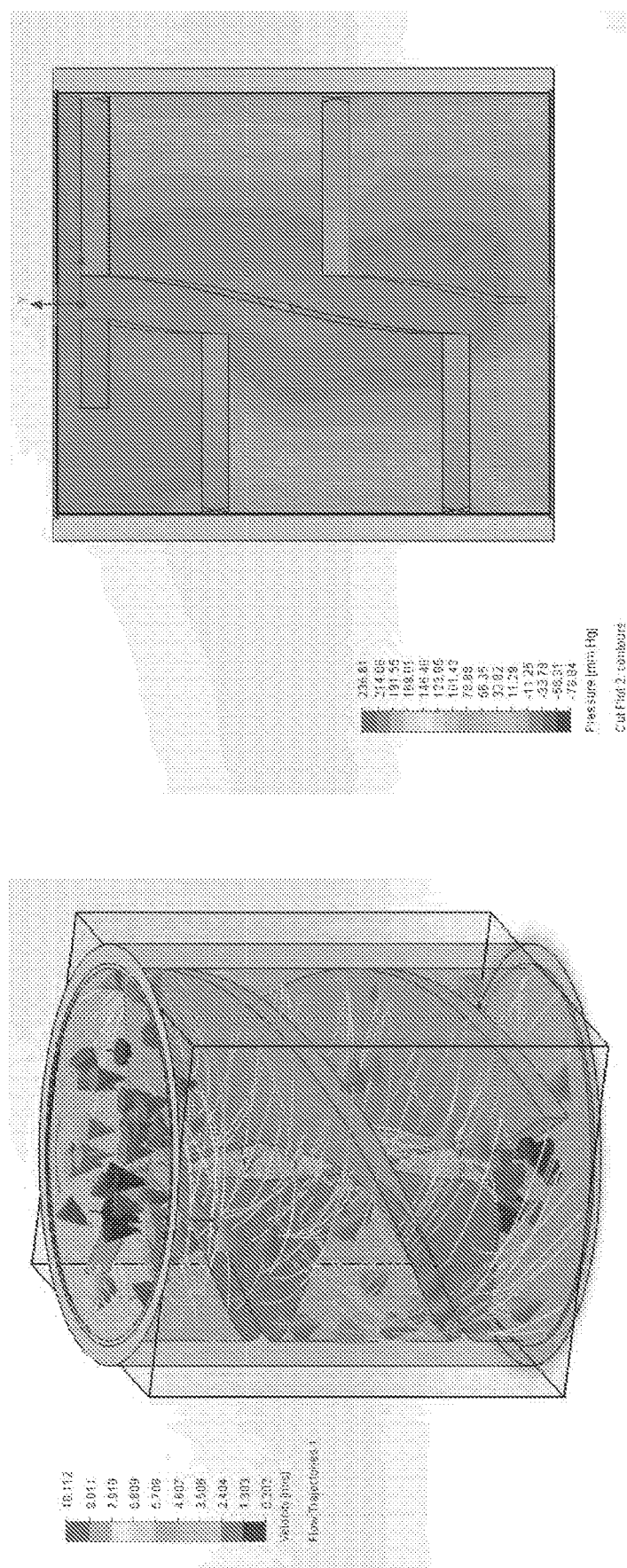
FIG. 40 depicts the simulated flow profile of a fluid actuator having a 15 mm height and a 15 mm diameter actuated at 10,000 RPM.
Figure 41:
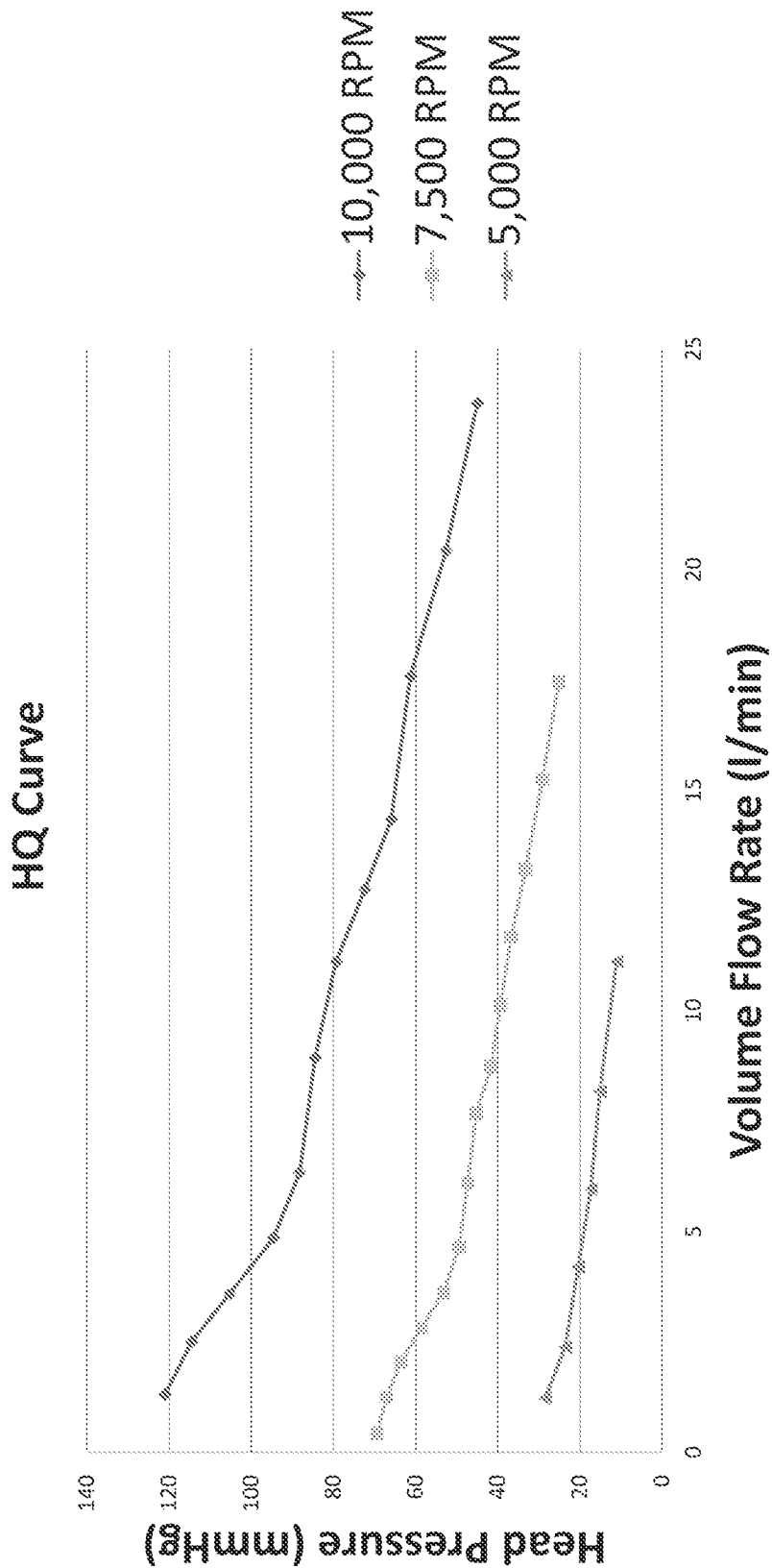
FIG. 41 depicts the relationship between flow rate and head pressure in a fluid actuator having a height of 15 mm and a diameter of 15 mm.
Figure 42:
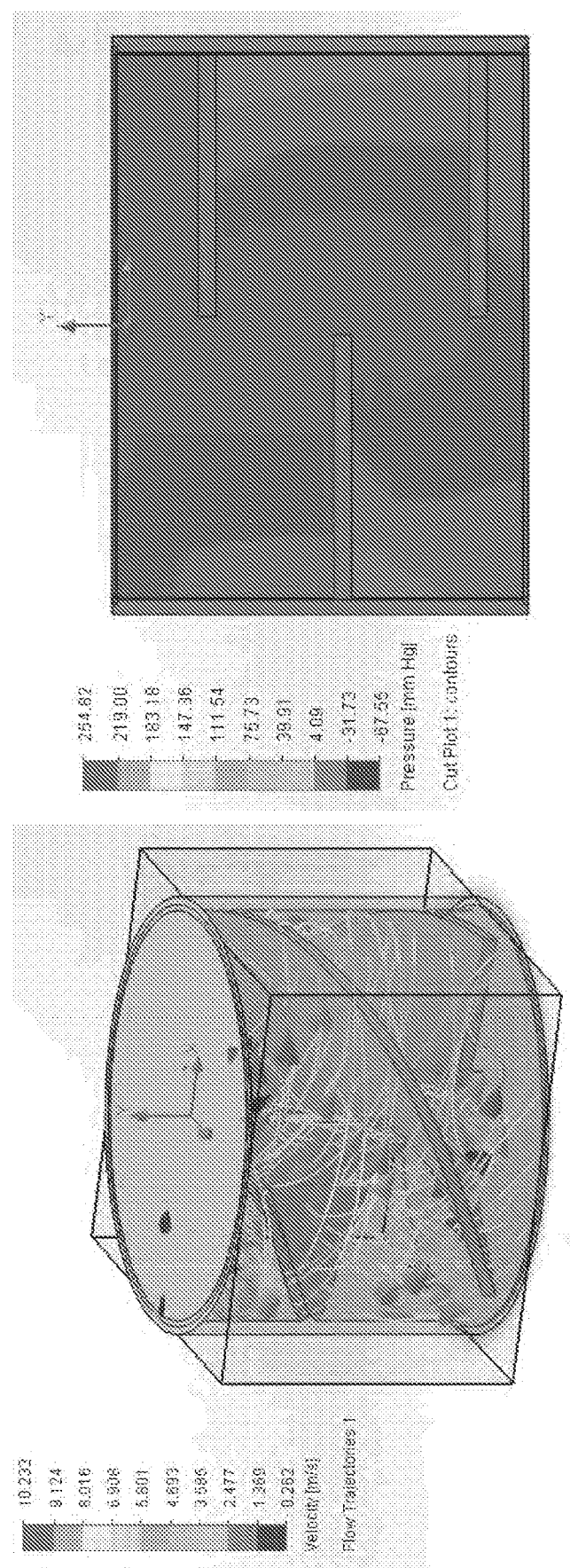
FIG. 42 depicts the simulated flow profile of a fluid actuator having a 20 mm height and a 30 mm diameter actuated at 5,000 RPM.
Figure 43:
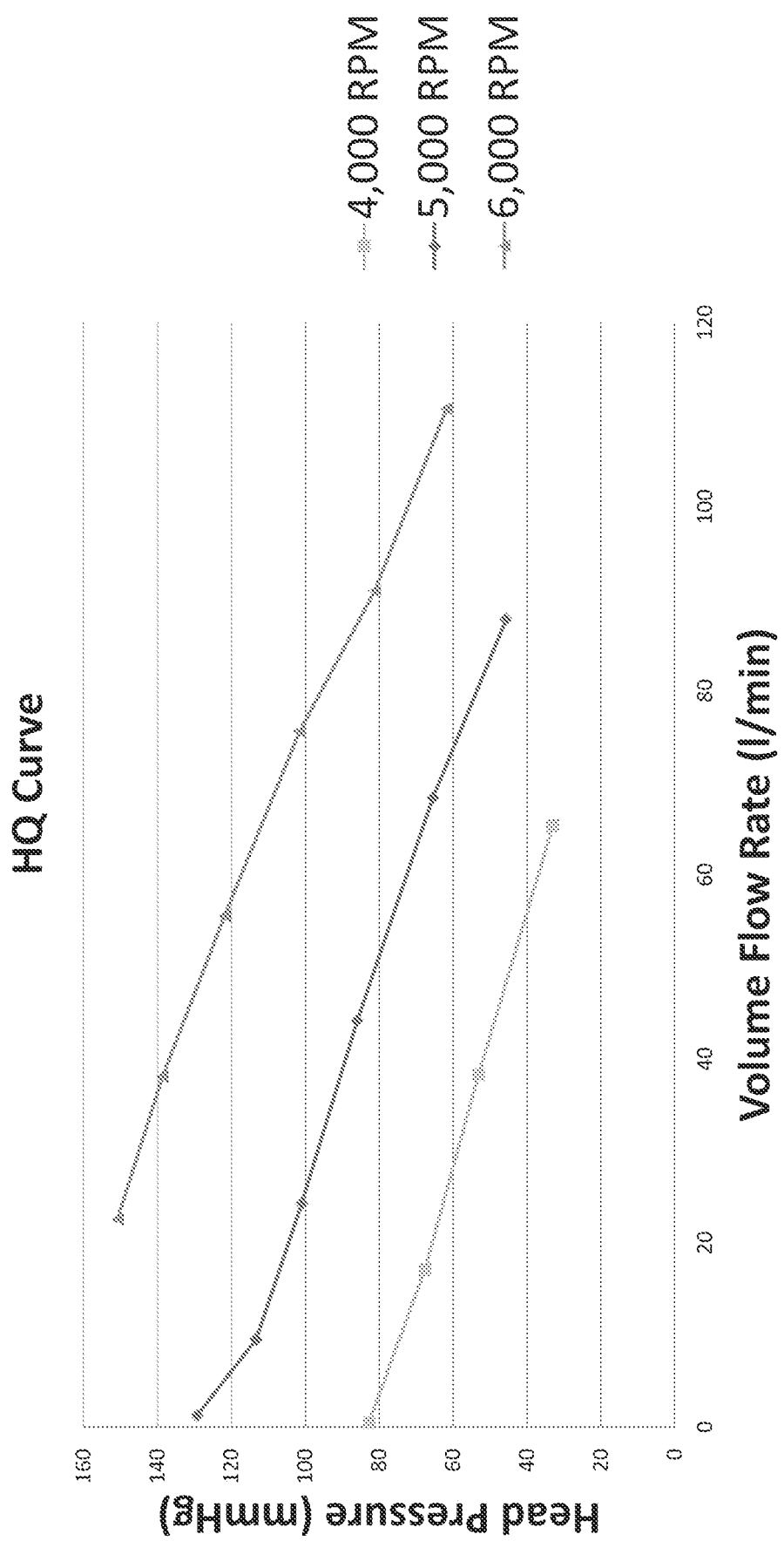
FIG. 43 depicts the relationship between flow rate and head pressure in a fluid actuator having a height of 20 mm and a diameter of 30 mm.

A wirelessly controllable on-demand recovery device was provided being composed of four elements: an axial pump, two valves, a cleaning port, and a transcutaneous energy transfer system (TETS) (FIG. 13). A brushed DC motor (8.5 mm in diameter and 20 mm in length) capable of operating under the maximum unload speed of 52 kRPM at 7.4 V was used for manufacturing an axial pump, in which impeller and diffuser designs were qualified by computational fluid dynamics (CFD) (FIG. 14, FIG. 15). A gear-driven valve was designed to generate open and closed maneuvers with proper amounts of force applied. An Objet30 3D printer with resin material was used to produce watertight prototypes. Performance tests were carried out using a mock circulation loop equipped with flowmeter and pressure transducers. Color dyes were used to quantitatively evaluate valve sealing capability and cleaning efficiency. Pump performance and wireless power transfer efficiency were also evaluated by creating a pump performance curve that shows flow and pressure relationships and by measuring the power successfully delivered to the system respectively.

The pump performance curve was created by controlling flow with manufactured valves. With two valves closed at the end of the graft where the pump is located inside, colored dyes were introduced into the graft and leaking dye concentration was measured, which resulted in negligible value (<0.1 ppm). Dyes inside the graft were then cleared out through cleaning ports. Concentration of the dye inside the graft after cleaning successfully dropped near zero (<0.1 ppm). Pump and valve operations were all achieved by wireless power delivery with an efficiency of 80%. The device can pump blood from the foramen ovale and return the blood to the ascending aorta, with the ability to shut the inflow and outflow and to clean the pump automatically when desired (7 cc volume), thus eliminating any clot formation within the pump.

Example 3: Novel Impeller Design

Rotating impellers have been a key technical solution to provide viable artificial heart pumps. Current impeller designs, however, are alien to the functional unit of the human circulatory system and remains a potential cause of adverse prothrombotic events such as hemolysis or pump thrombus by forcing blood cells to pass over limited space available within rapidly alternating blades attached along a central hub, which is fundamentally a non-physiological flow. The following study presents a biologically inspired new impeller design for a circulatory assist device that maximizes the flow path while minimizing shear stress, allowing physiological flow. Design parameters including inner diameter, helix height, overall height, helix revolutions/pitch, blade length, blade thickness, introductory blade angle, blade number, and blade shape optimized for maximum output volumetric flow rate through the parametric analysis in computational fluid dynamics simulation. The final design showed an improved flow path by securing 70% of the passage, compared to conventional artificial heart pumps where the flow path occupies approximately <5%. The new impeller design with a 17 mm diameter can produce a flow rate up to 25 mL within 15,000 RPM. The performance curve covers the domain of 2-6 L/min at 20-50 mmHg and 3-8 L/min at 50-100 mmHg, the functional requirements for RVAD and LVAD respectively. 3D printed prototypes operated within 10,000 RPM and reached a maximum flow rate of 10 L/min at 60 mmHg, which well matches the simulation results, demonstrating the feasibility of the design. Extraordinary performance of the new impeller far exceeds these requirements and can open up wider applications of mechanical circulatory support.

Avian cardiovascular systems, much like that of humans but with far better performance and efficiency, accommodate a broad range of activities from swimming to flying. Inspired by the structure of the atrioventricular valve in birds having a spiral flap of myocardium attached obliquely downward from the free wall of the atrium to that of the ventricle toward its apex, a novel impeller design was conceived where spiral shaped blades are attached to an outer shell to maximize the flow path while minimizing shear stress, allowing physiological flow.

Computational simulations of this bioinspired miniaturized impeller design showed operating ranges of 15-25 L/min at 40-80 mmHg with 15,000 RPM, a remarkable flow improvement compared to conventional impeller designs. The flow performance of 10 L/min has been achieved in preliminary benchtop experiments. Such a high flow range broadens applications not limited to ventricular assist devices but to patients with sepsis by rapidly removing bacterial products circulating the patient's body.

Design

The impeller design has three angled blades attached to a cylinder wall with an unobstructed bore at the center (FIG. 44A). A fully developed flow profile through the bore in the impeller center reduces frictional and hydraulic losses by retaining the original and undisturbed flow profile, close to physiological flow. Pump performance (e.g. volumetric flow rate, head pressure, torque) can be modulated by eight influential parameters: Inner Diameter (d), Helix Height (H), Helix Pitch (p), Blade Length (l), Blade Thickness (t), Introductory Blade Angle ($\alpha$), Number of Blades (n), and Blade Shape (FIG. 44B).

Simulation

Initial optimization studies for the impeller design was performed through a SolidWorks Flow Simulation module using the setup described in Table 1.

TABLE 1

Simulation setup in SolidWorks Flow Simulation module for parametric study and initial design optimization.

| Parameter | Value |
| --- | --- |
| Analysis type | Internal |
| Temperature | 310 K (Body Temperature) |
| Liquid | Blood |
| Flow Model | Non-Newtonian |
| Flow | Laminar |
| Wall | Adiabatic, no roughness |
| Inlet boundary condition | 60 mmHg |
| Outlet boundary condition | 120 mmHg |
| Environmental Pressure | 120 mmHg |
| Rotation | 5000-12500 RPM |

Figure 45:
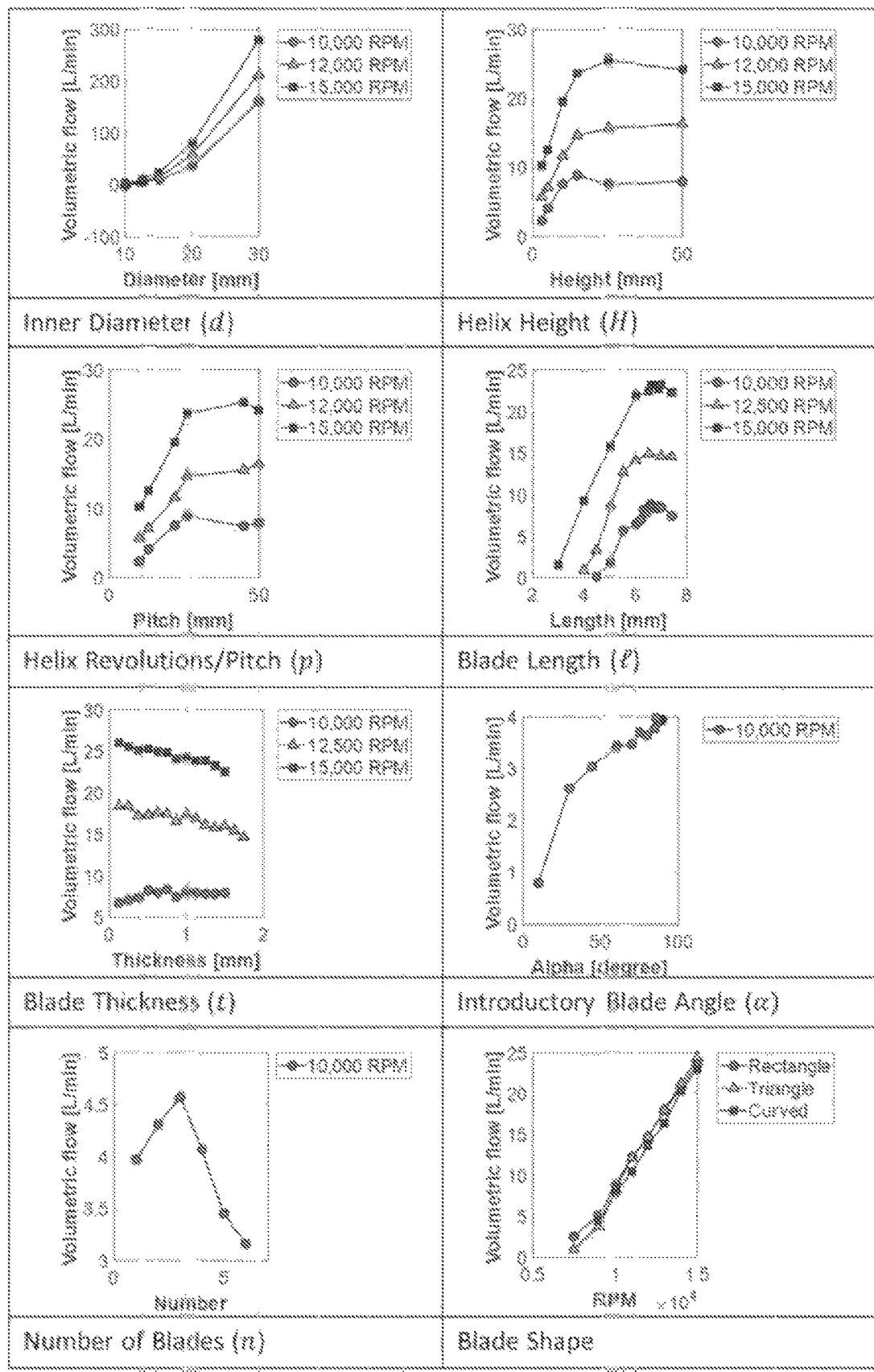
FIG. 45 depicts the results of a parametric study modulating volumetric flow rate. The initial impeller design was modulated to maximize volume flowrate by varying design parameters. Initial values of 15 mm, 15 mm, 26 mm, 6.5 mm, 1 mm, 90 degrees, 3, and Rectangle (Parallelogram) shape for Inner Diameter (d), Helix Height (H), Helix Pitch (p), Blade Length (l), Blade Thickness (t), Introductory Blade Angle ($\alpha$), Number of Blades (n), and Blade Shape respectively were used unless otherwise stated under the simulation setup described in Table 1.
Figure 46A:
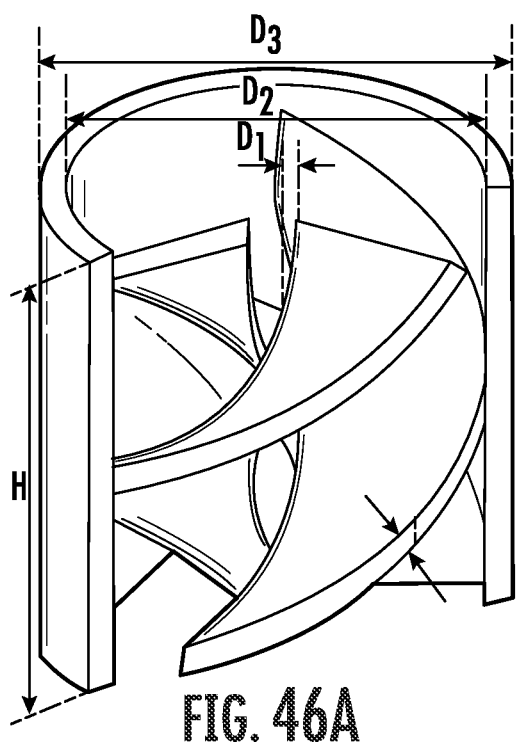
FIG. 46A through FIG. 46C depict computational models and setup.
Figure 46B:
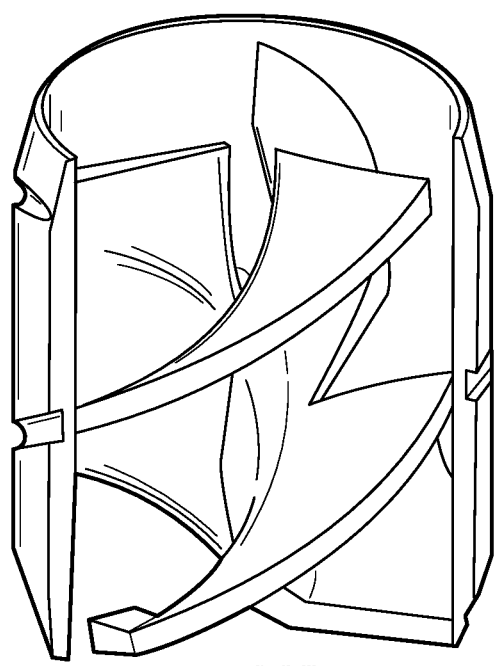

Parametric analysis of geometrical variations on the impeller design aimed at maximizing output volumetric flow rate (FIG. 45) along with assessing head pressures and torque. Two final models, Mod 1 (FIG. 46A) and Mod 2 (FIG. 46B), determined based on these initial optimization studies were examined in detail with Ansys software. Mod 2 is a further refined model based on Mod 1 simulation results to see how certain design changes (Table 2) affect overall performance.

TABLE 2

Design parameters for Mod 1 and Mod 2.

| | Parameter Descriptions | Mod 1 | Mod 2 |
| --- | --- | --- | --- |
| Bushing | Height (H) | 18 mm | 18 mm |
| | Outer diameter ($OD_b$) | 17 mm | 17 mm |
| | Inner diameter ($ID_b$) | 15 mm | 15 mm |
| | Trough depth ($t_t$) | NA | 800 μm |
| | Trough width ($w_t$) | NA | 800 μm |
| Blade passage | Hub diameter ($D_1$) | 2.1 mm | 2.1 mm |
| | Shroud diameter ($D_2$) | 15 mm | 15 mm |
| | Wrap angle (θ) | 207.69° | 219° |
| | Outer outlet angle ($\beta_1$) | 61.083574° | 61.083574° |
| | Outer outlet angle ($\beta_2$) | 90° | 90° |
| | Blade thickness (t) | 0.246-0.828 | 0.246-0.828 |
| Housing | Diameter ($OD_H$) | 18 mm | 18 mm |
| | Gap size (g) | 500 μm | 500 μm |

Figure 46C:
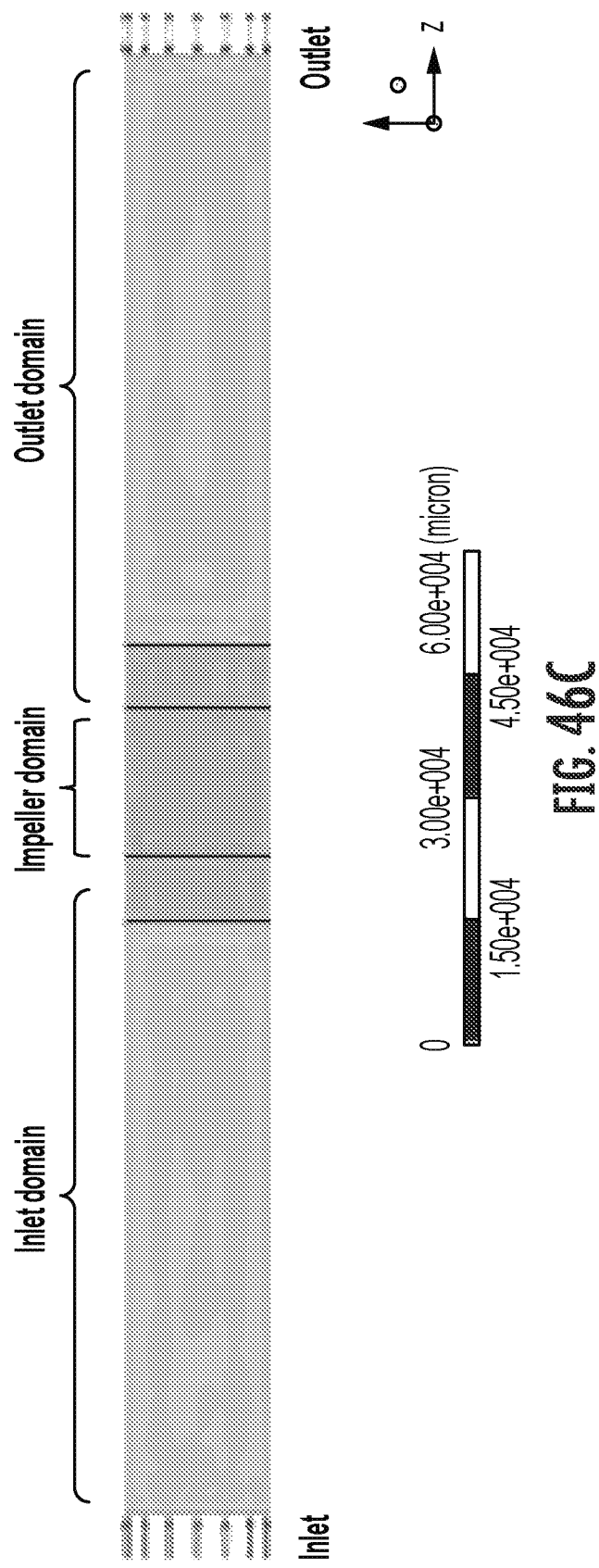

In Mod 2, tapered ends for a smooth blood transition into the gap were implemented. The cut off at the leading edge in Mod 1 was replaced with rounded edges to decrease hydraulic losses. The trailing edge was transformed to a vertical cut-off. Among all, the key features added to Mod 2 were the troughs on the outside with the same wrap angle as that of the impeller blades, which is expected to prevent backflow through the outer gaps and thereby increase overall pump efficiency. For Mod 1, an elongated inlet and outlet domain of 80 mm has been implemented to decouple the pump hydraulic prediction from any flow effects, e.g. vortex formations, near the inlet and outlet. A mass flow boundary condition for the inlet combined with an opening pressure boundary condition for the outlet promises a suitable setup for a stable steady state simulation and valid results. The complete geometry has been assembled from 12 domains to ensure a high-quality mesh. The impeller was meshed mainly in structured hexahedral meshes using Turbogrid (Ansys Inc., USA). All other domains were meshed in Meshing (Ansys Inc, USA). Prism layers and gap refinements were used to resolve wall shear adequately in all domains. The overall mesh consists of 4,418,397 elements. For Mod 2, evaluation was performed at 15,000 RPM with three chosen flow rates: 5, 10, and 20 L/min (marked by red asterisk) for comparison with Mod 1 using a similar setup and meshing approach to those for Mod 1. The geometry has been divided into 17 domains to resolve potential hotspots. A mesh with 13,299,271 elements was generated. FIG. 46C shows the geometrical setup for the pump assessment in Ansys software.

Prototyping

Rim-driven impeller: A 3D printed rim-driven impeller was built to investigate flow characteristics within three different inlet & outlet configurations, small to large (StoL), large to small (LtoS), and large to large (LtoL) (FIG. 47A). Here, small and large indicates diameters of 8 mm and 15 mm, respectively. The rim-driven impeller prototype was composed of a rotor, inlet & outlet housing, ball bearing, and actuator created based on a dLRK winding scheme with 10 magnets and 12 slots. Strong ¼" neodymium cube magnets were circularly arrayed at the outer circumference of the rotor with the impeller located at its center. Once the rotor mounted on the ball bearing (inner diameter of 20 mm and outer diameter of 42 mm) was encased with the top and bottom housing, the stator where twelve flat screws were wound by 25 turns of 24 Gauge copper wire for each was mounted on the top housing. A ZTW Beatles 40A Electronic Speed Controller (ESC) was used to control the speed of the actuator. A throttle range from 1000 to 1600 was used. All 3D printed components were made of resin materials using a Stratasys Objet30 Pro 3D printer.

Figure 55A:
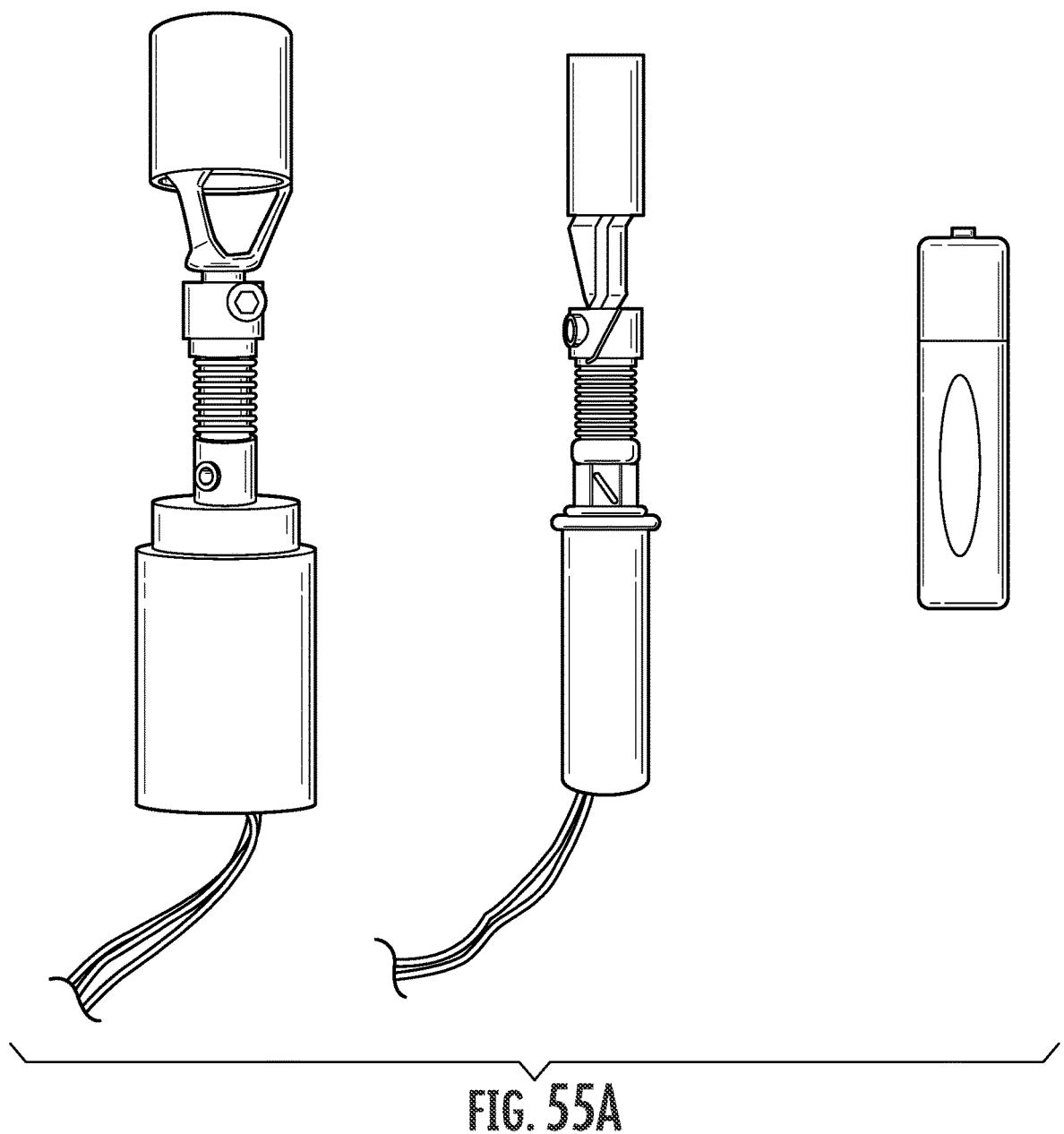
FIG. 55A through FIG. 55C depict exemplary prototype impellers.
Figure 55B:
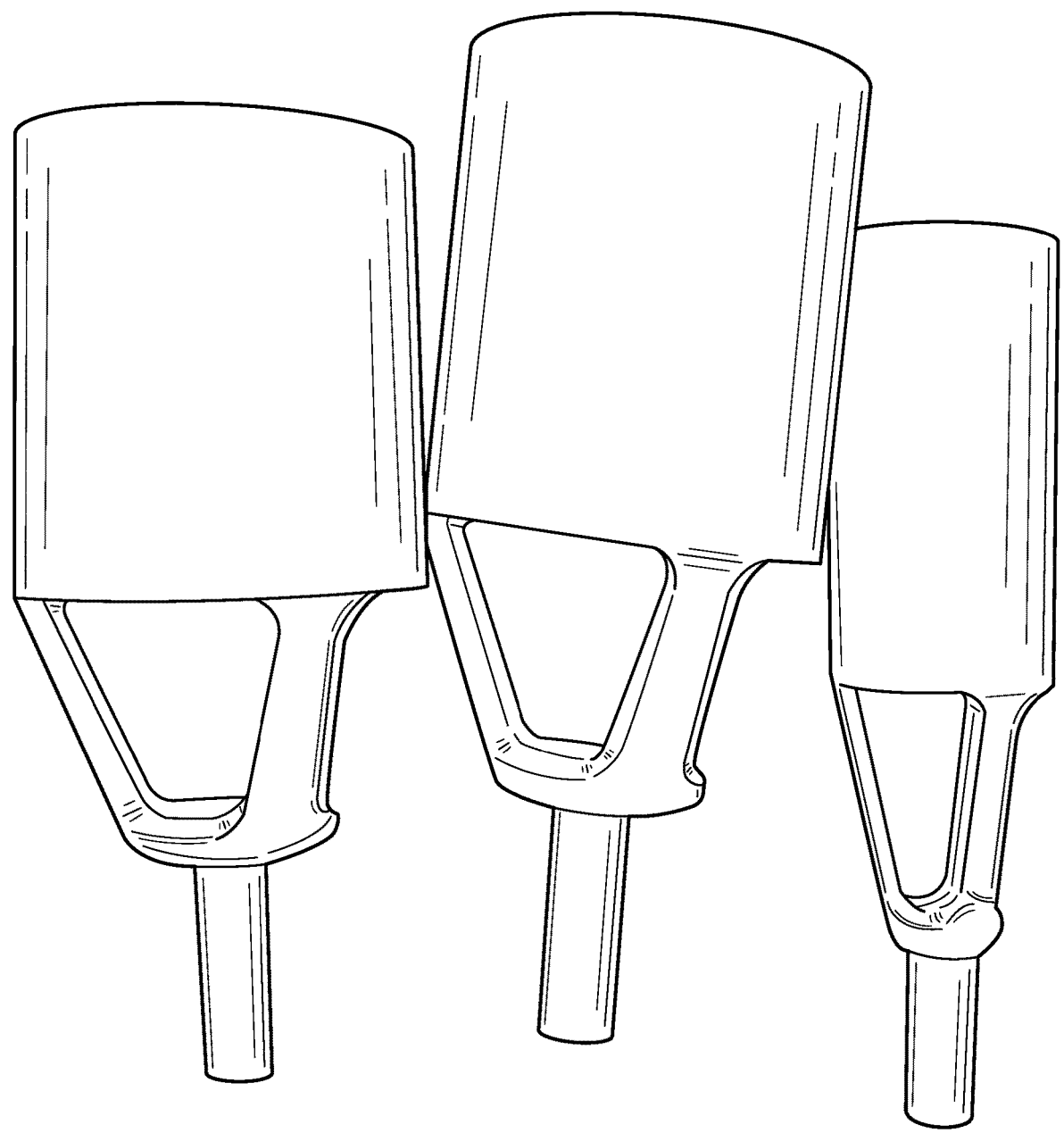
Figure 55C:
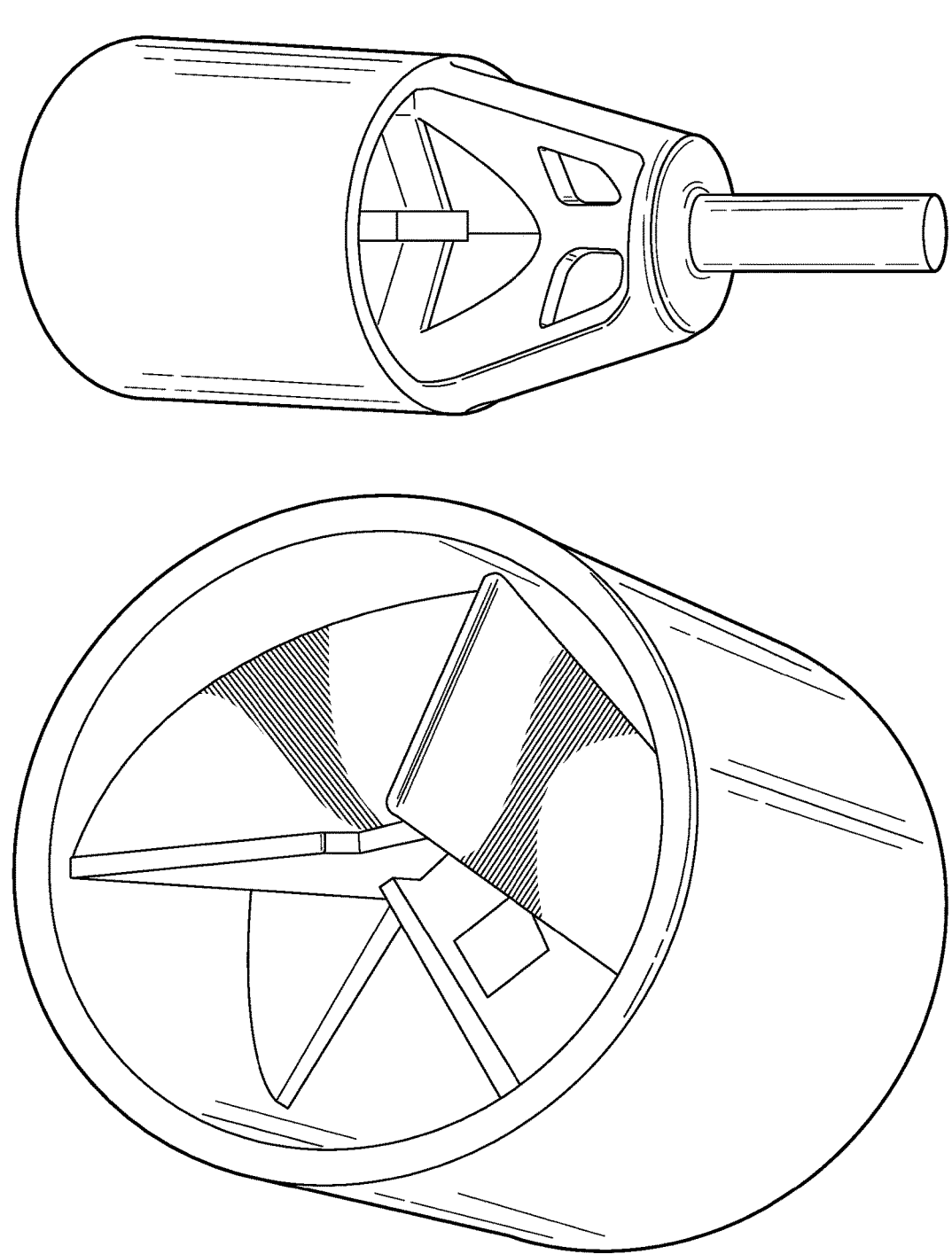

Shaft-driven impeller: A 3D printed shaft-driven impeller was built to demonstrate pump performance. Prototypes were built with two different impeller diameters, 9 mm and 15 mm, in which the larger design corresponds to the one used in the computer simulation study (FIG. 47B). Prototypes were designed to run with a brushless micro DC motor (Turnigy 1230, Hobby King USA LLC, Lakewood, Wash.) by directly connecting the impeller to its shaft with a mechanical coupling (S50FP9MFB153008, SDP-SI, Designatronics Inc., NY, USA). Impellers were either made of aluminum or stainless steel and other components were made of resin materials using a Stratasys Objet30 Pro 3D printer (FIG. 55A through FIG. 55C).

Simulation Results

Volumetric flow rate increased significantly with diameter. However, a larger diameter comes at the price of a larger component. Volumetric flow rate increased with height up to a helix height of approximately 20 mm. Increases in height above 20 mm led to very minimal changes in volumetric flow rate, concluding that an optimal height is approximately 15-25 mm. The optimal pitch to maximize volumetric flow rate varied with the helix height. Torque decreased with an increase in pitch. Volumetric flow rate significantly increased with blade length up to a maximum length of d/2, where d is inner diameter, while head pressure and torque increased with the blade length. Volumetric flow rate slightly decreased with an increase in blade thickness but the effect was not significant. Blade thickness had a minimal effect on head pressure and torque as well. Blade shape also had a minimal effect on the volumetric flow rate. Therefore, the shape can later be tuned to minimize stress on blood. Through this initial design investigation with respect to each parameter, Mod 1 and further refined model Mod 2 based on Mod 1 simulation results were created for detailed analysis including pump performance, efficiency, and flow field.

Figure 48A:
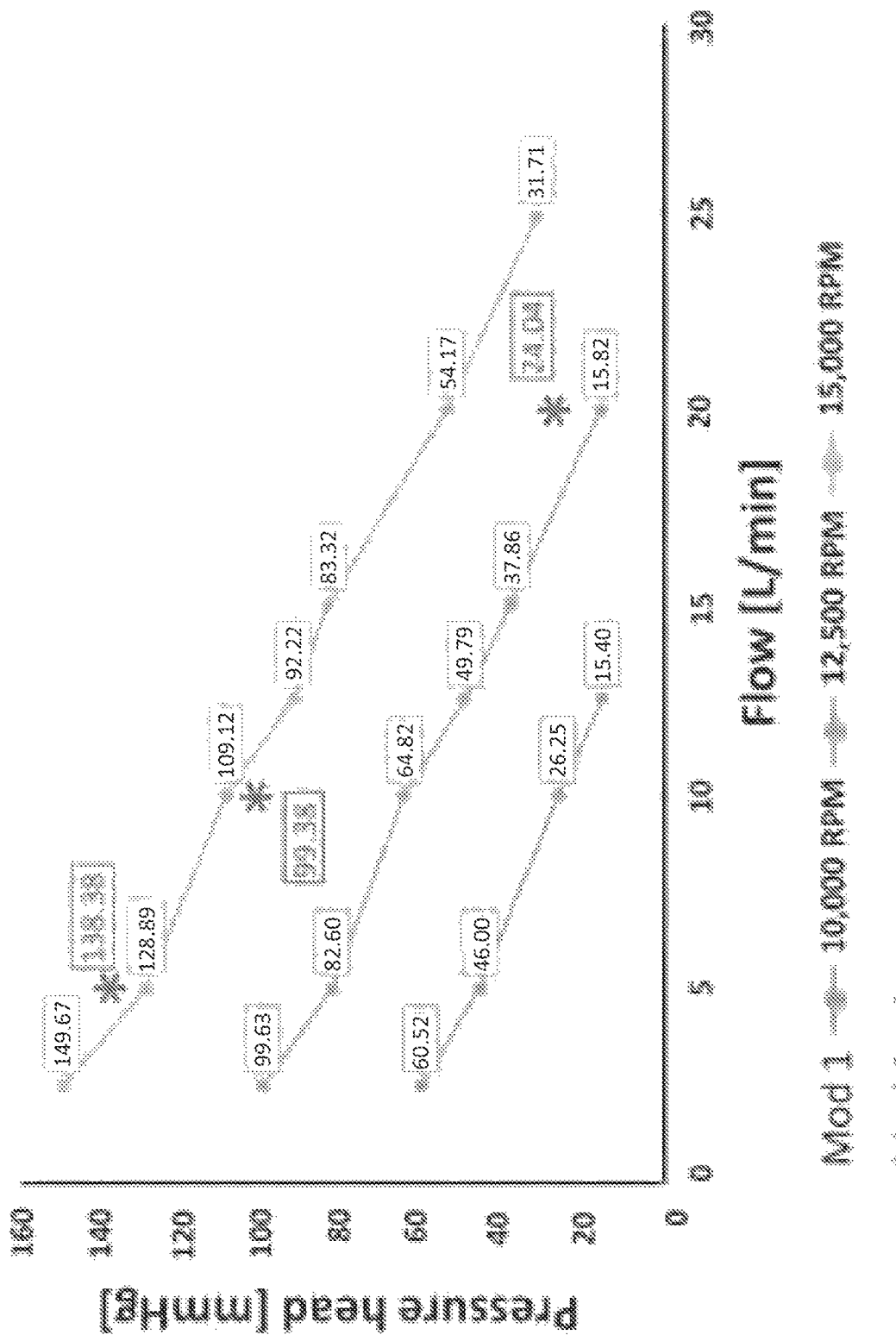
FIG. 48A and FIG. 48B depict experimental pump performance curves and static efficiency of final computational models. Numerically determined pressure heads (FIG. 48A) and pump hydraulic efficiency (FIG. 48B) are presented at different flow rates within three different pump speeds for Mod 1 and at three different flow rates (5, 10, 20 L/min) within 15,000 RPM for Mod 2 for comparison. Mod 2 resulted in a steeper pump curve. The best hydraulic efficiency points (BEP) are defined as the maximum of each efficiency curve. Similar to common blood pumps, it shows a tendency to have higher maxima for higher pump speeds. The highest efficiency that could be achieved within the range of the investigated pump speed is 10.95% at 20 L/min.

A numerically determined pressure head at flow rates and at three different pump speeds (10,000, 12,500, and 15,000 RPM) gave a first insight in pump performance (FIG. 48A). The pump performance curve of Mod 1 shows that an adequate flow-pressure (>5 L/min at 30-40 mmHg) relation for a right ventricular assist device operating at full support can be achieved at a pump speed below 10,000 RPM and an adequate flow-pressure (>5 L/min at 80-120 mmHg) relation for a left ventricular assist device operating at full support at a pump speed of 15,000 RPM. Similar to common blood pumps, the pump hydraulic efficiency over different flow rates at the three different pump speeds showed a tendency to have higher efficiency for higher pump speed (FIG. 48B).

Figure 48B:
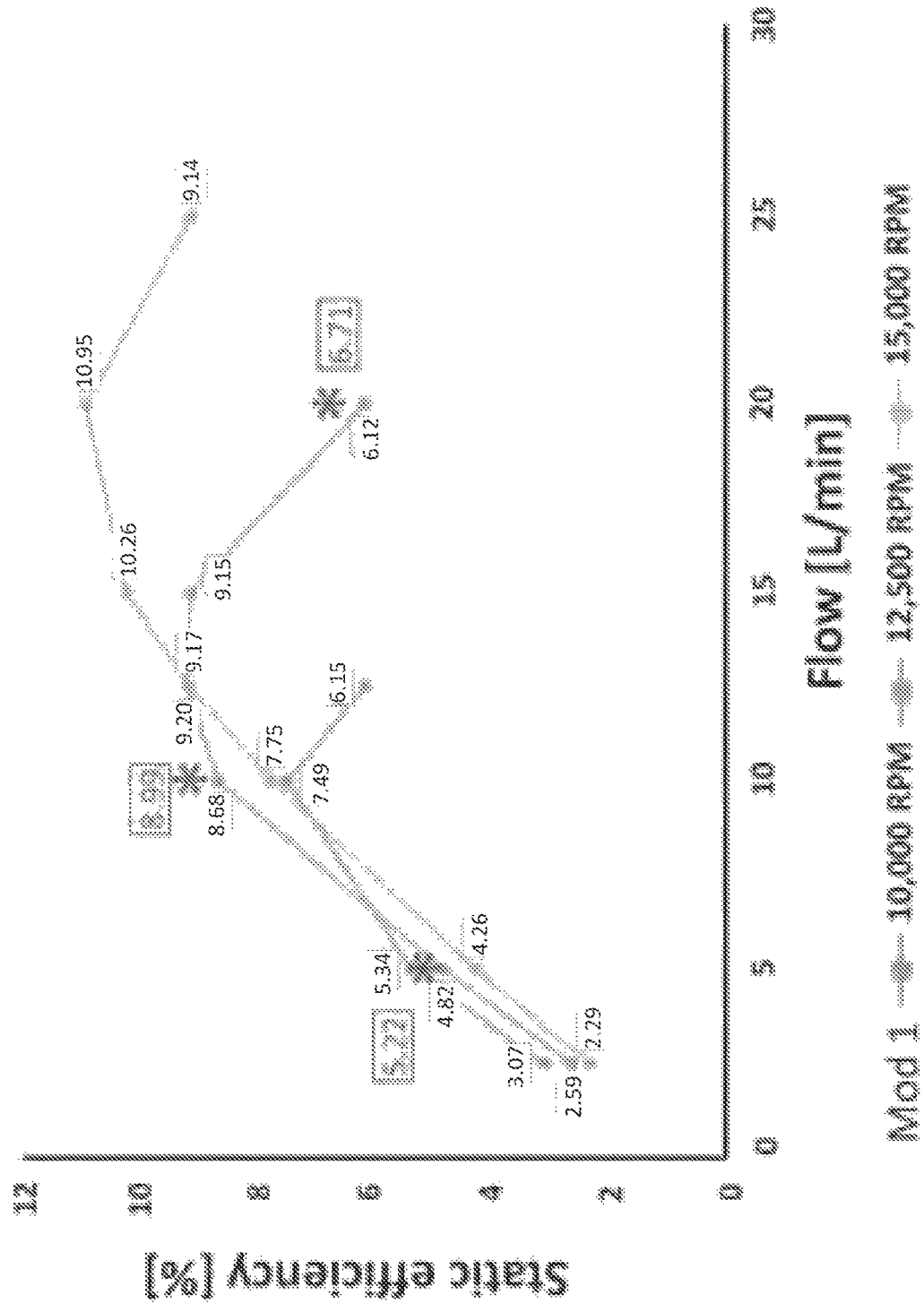
Figure 49A:
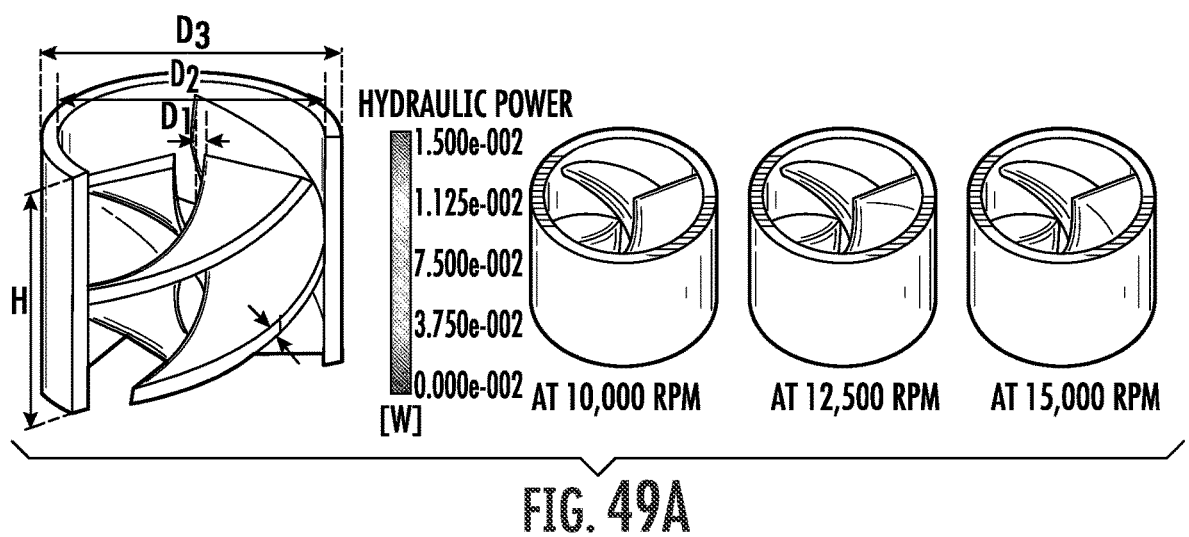
FIG. 49A through FIG. 49D depict the results of flow field analysis on final computational models. Hydraulic power, which highlights areas where hydraulic losses occur, on the final models Mod 1 (FIG. 49A, FIG. 49B) and Mod 2 (FIG. 49C, FIG. 49D) are shown. For both models, negligible hydraulic losses were found in the gap between busing and housing compared to those on the blades (FIG. 49A and FIG. 49C).
Figure 49B:
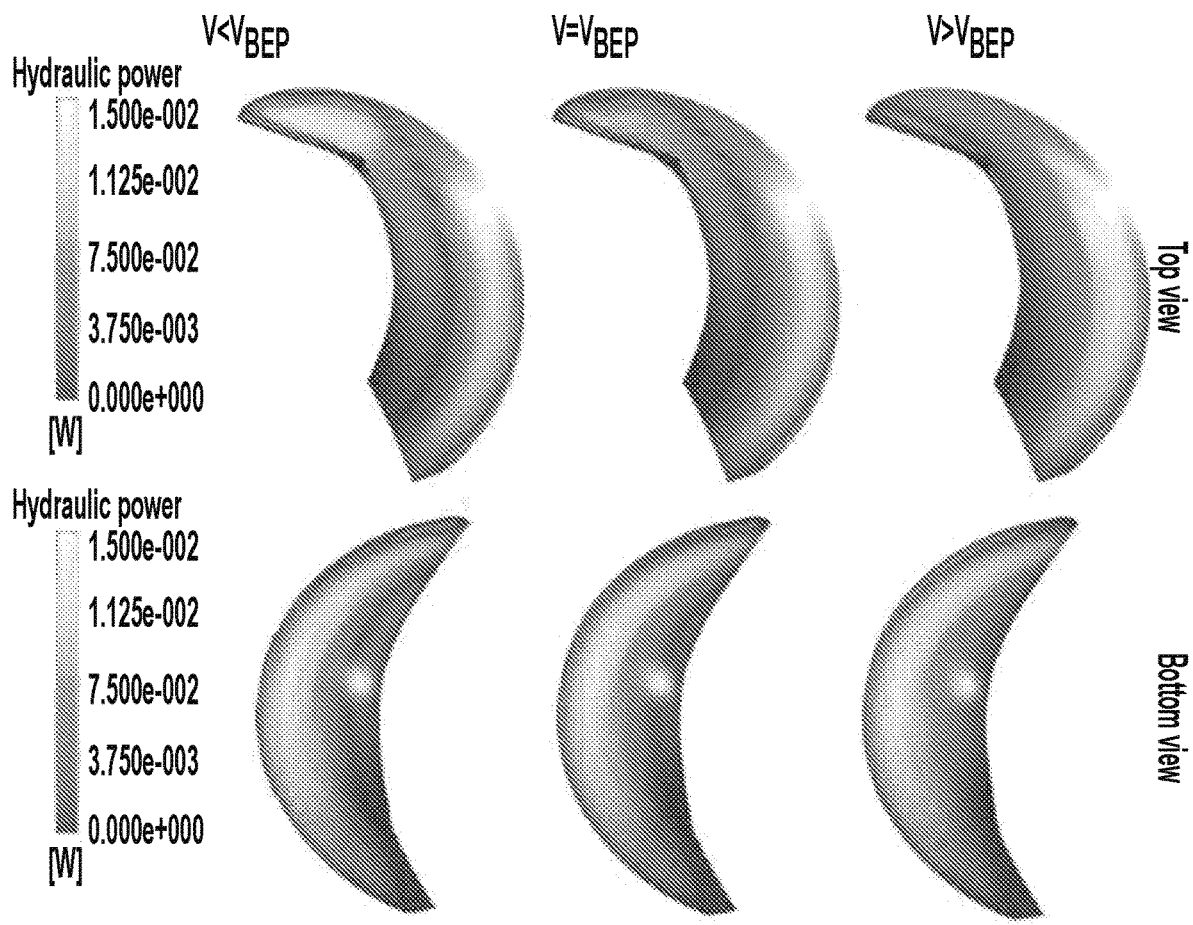
Figure 49C:
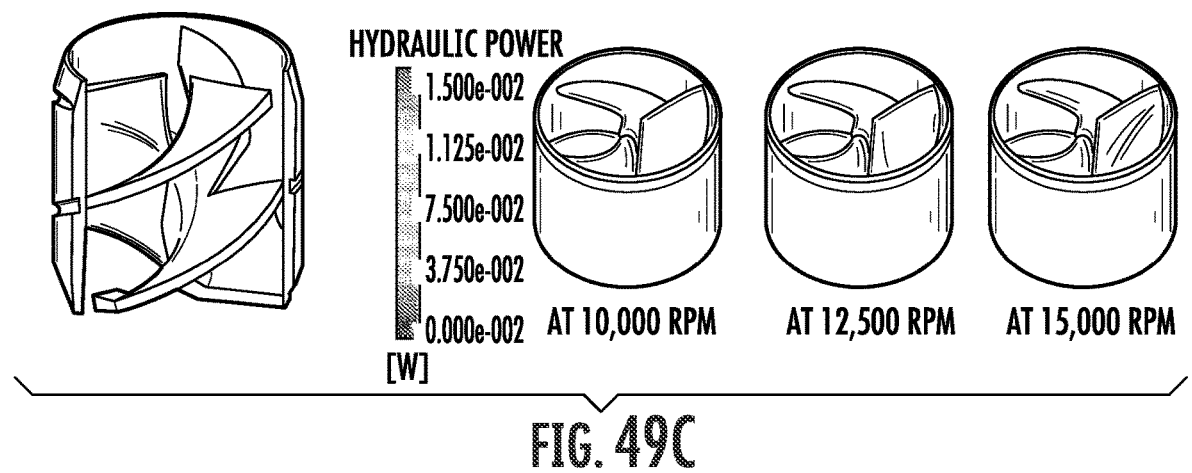
Figure 49D:
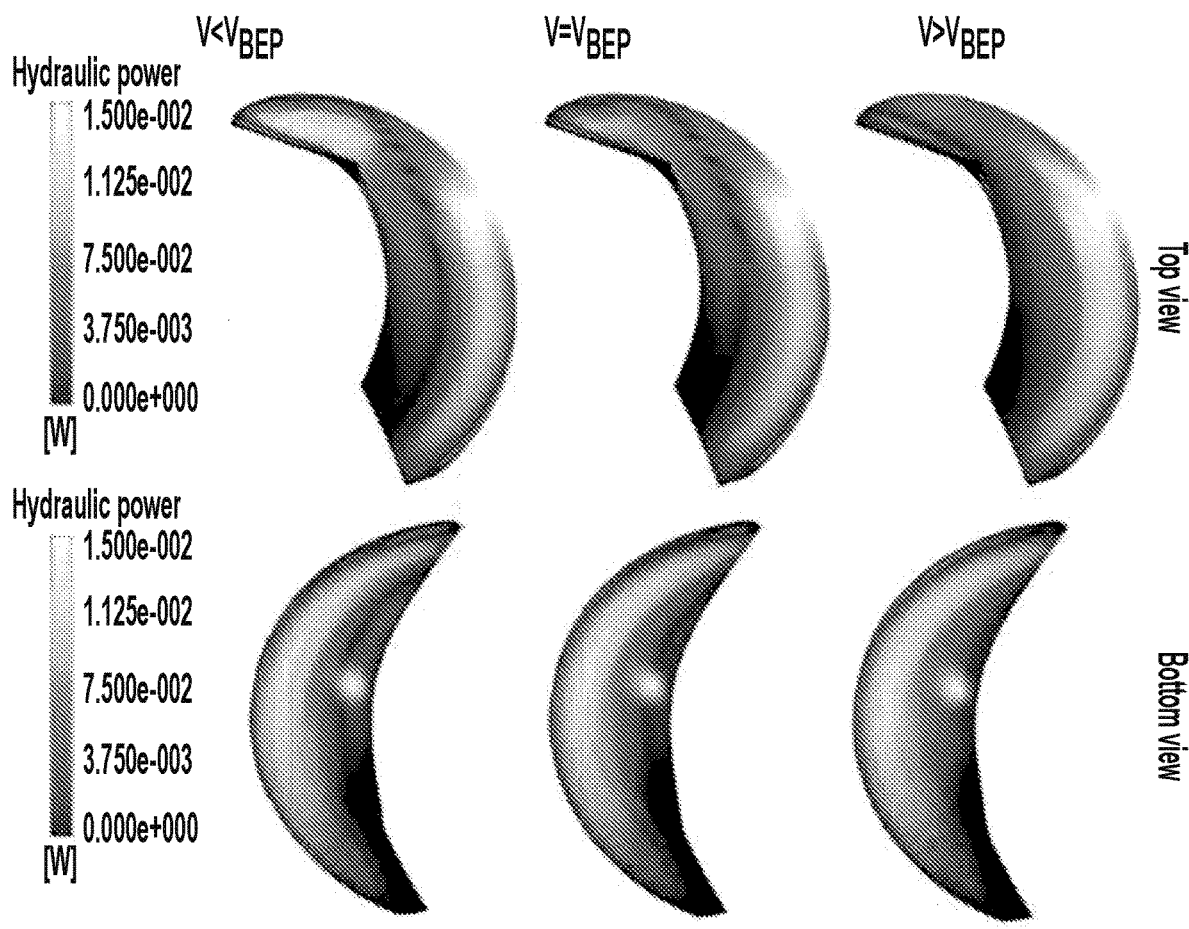
Figure 50:
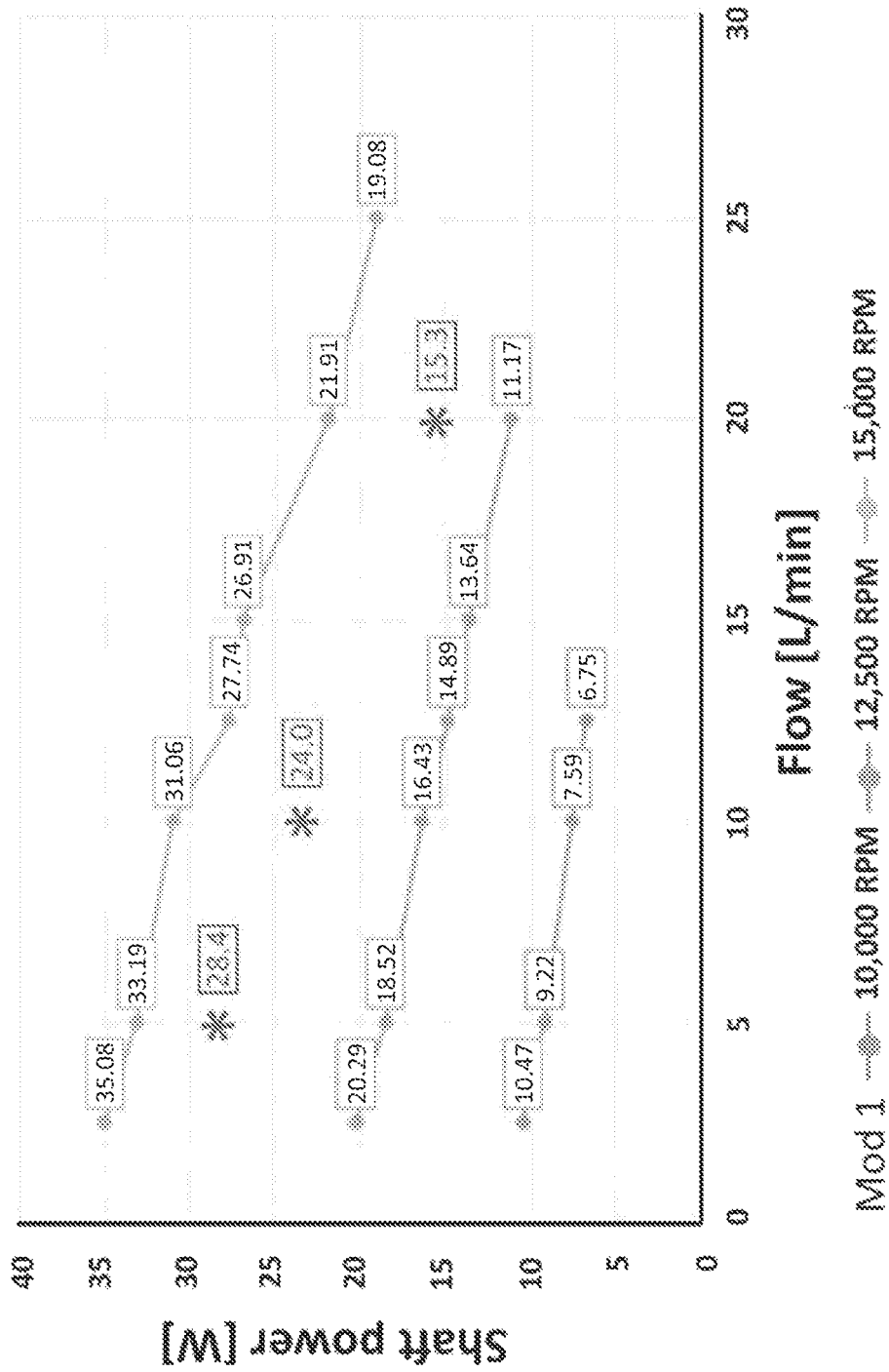
FIG. 50 depicts a graph showing shaft power resulting from Mod 1 and Mod 2. Shaft power is an integral of hydraulic power plotted in FIG. 48A and FIG. 48B as a variable over the blade surfaces which visualizes efficiency of the flow guidance and highlights areas where hydraulic losses occur.

Flow field analysis was carried out at the best efficiency points (BEP) defined as the maximum of each curve in the efficiency plot in FIG. 48B (for example, flow field analysis at 20 L/min for 15,000 RPM). Here, hydraulic power which visualizes efficiency of the flow guidance and highlights areas where hydraulic losses occur has been evaluated and shown as a variable on the impeller (FIG. 49A through FIG. 49D). The integral of this variable over the full impeller surface yields the shaft power as an absolute value (FIG. 50). For all three pump speeds, negligible hydraulic losses were found in the gap between bushing and housing compared to those on the blades (FIG. 49A and FIG. 49C). In single blade analysis evaluated at pump flows below ($V<V_{bep}$), at ($V=V_{bep}$) and above ($V>V_{bep}$) the BEP, a hot spot of the hydraulic power is found on the top surface, right behind the leading edge, typically caused by flow detachment (FIG. 49B and FIG. 49D). This is usually the case when the blade angle of the leading edge is too high. This assumption is proven by the fact that this spot decreases with flow but increases with pump speed (FIG. 50). The inner half of the blade does not provide any flow guidance to the flow. The horizontal cut-offs as leading edges cause flow impingements and an increase in hydraulic power.

Figure 51A:
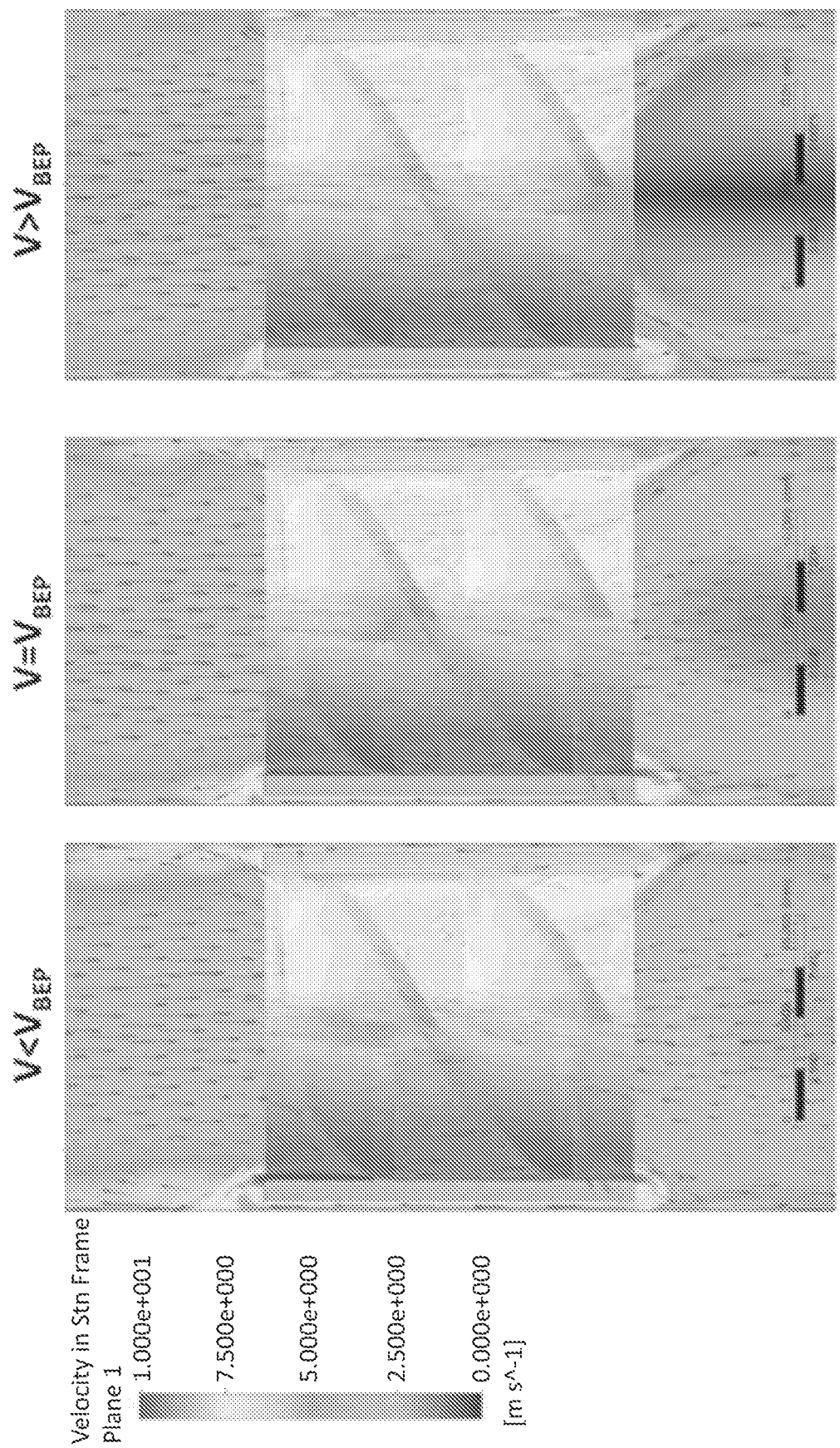
FIG. 51A and FIG. 51B depict the results of experiments investigating flow field and quantified back flow.

The hydraulic flow field inside the Mod 1 pump shown in FIG. 51A for 12,500 RPM presents back flow in the gap between bushing and housing. The backflow is linearly dependent on the pressure gradient. A certain amount of backflow is necessary to ensure the washout of the gap region, but within the range that does not negatively affect pump efficiency. The backflow is quantified in FIG. 51B.

Figure 51B:
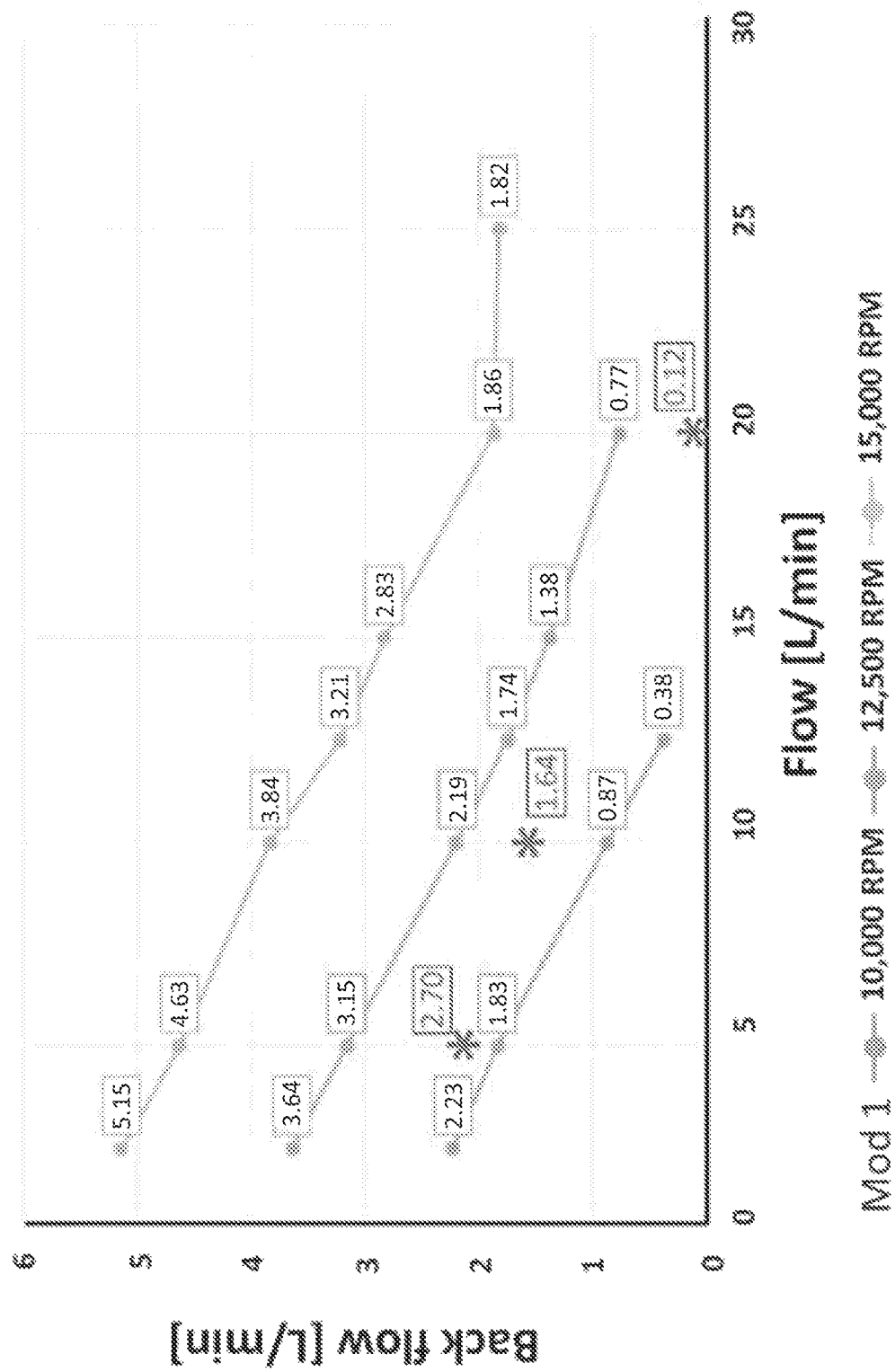

The second design (Mod 2) was created based on Mod 1 simulation results. The altered pump performance curve shown in FIG. 48A with that of Mod 1 demonstrates that the simple design changes can provide considerable impact on the pump hydraulics. Mod 2 created a steeper pump curve, which means a pressure drop results in smaller changes in flow. In other words, flow will be more stable against pressure variations. The hydraulic efficiency curve shows the tendency of a more left-sided skewed curvature peak, resulting in an altered BEP for Mod 2 (FIG. 48B). The shaft power was decreased but in a disproportional relation to the pressure head (FIG. 50). The secondary gap backflow significantly decreased compared to Mod 1 attributed to the implementation of the troughs on the busing (FIG. 51B). The influence of the chamfers remains disputable since the tangential velocity component in and before the gap is predominant. However, the tapered ends cause a reduction of the vortices production within the impeller inlet region. Similar to Mod 1 results, the contour plots of the shaft power as a variable on the impeller show that the outer trough have a negligible influence on the overall integrated shaft power compared to the blade passages (FIG. 49B).

Prototyping Results

Figure 53B:
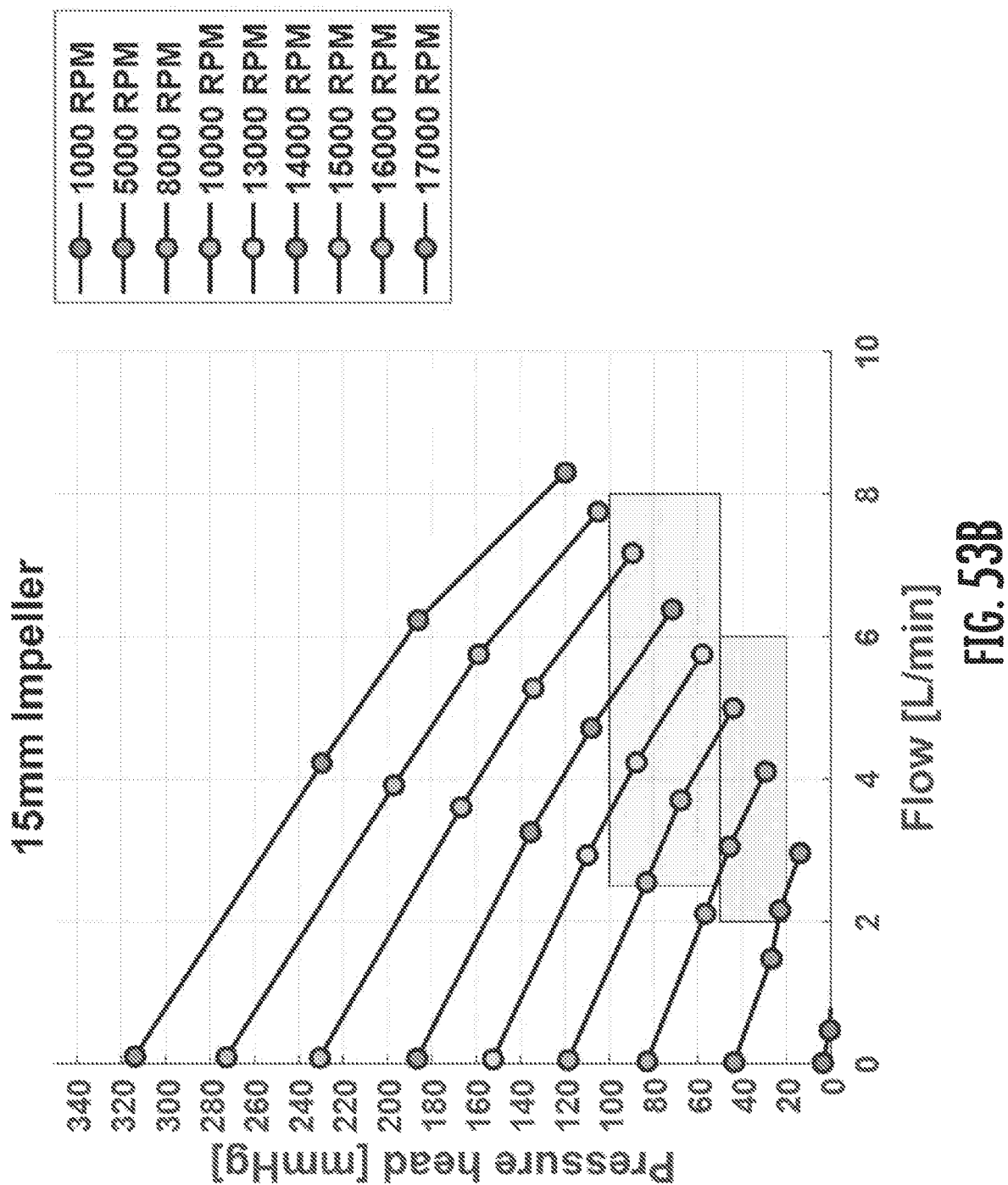
Figure 54B:
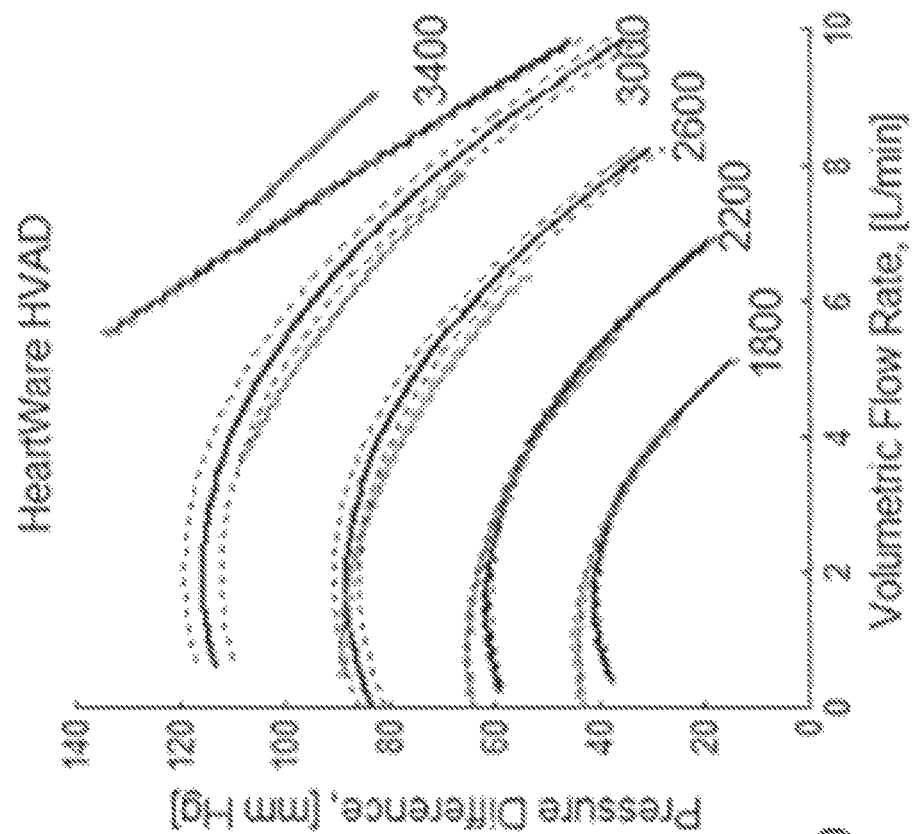
Figure 54A:
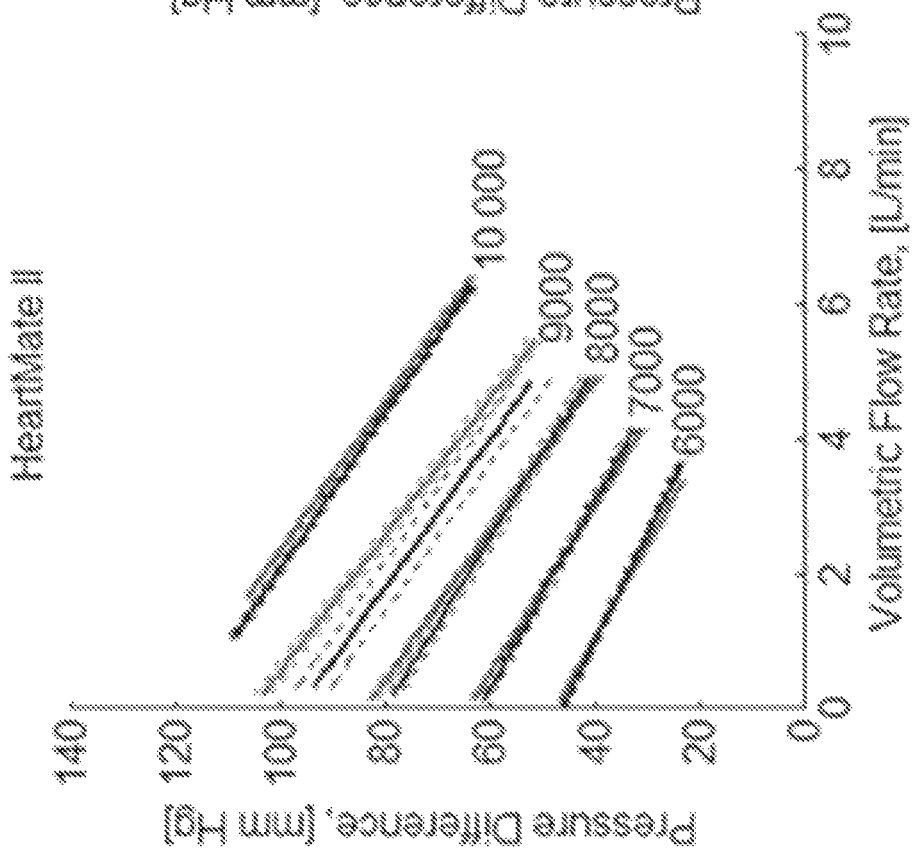

With a LtoL configuration in which impeller configuration is the same on either side as the design is symmetric, the direction of a rotation simply determines the flow direction without the performance change. Slight differences in flow at throttle of 1600 between clockwise and counter clockwise rotation is due to necessarily existing structural differences (ball bearing at only one side) between inlet and outlet even though inlet and outlet diameters are identical (FIG. 52A). However, if there are variations between inlet and outlet (e.g. StoL and LtoS), flow was only able to be created from small to large with reduced performance compared to that of LtoL (FIG. 52B and FIG. 52C). Therefore, within the new impeller design, the direction of rotation needs to be determined based on duct configuration to create forward flow and optimal performance can be expected from a straight duct in which inlet and outlet are identical. FIG. 53A and FIG. 53B show pump performance curves for small and large impellers, respectively. Compared to currently used assist devices (HeartMate II, FIG. 54A; HeartWare HVAD, FIG. 54B; HeartMate III, FIG. 54C), the new impeller provides greater flow rates with lower pressure at comparable RPM.

The new impeller provided additional advantages over traditional designs. Traditional impellers employ blades attached along a central shaft, whereby the central shaft presents additional surface area for heat generation from friction generated by fluid flow. The new impeller with a shaftless design decreases the surface area exposed to fluid flow, thereby reducing friction and heat generation. A benefit to producing greater flow efficiencies with the new impeller is that the pumping action is less traumatic to blood cells and other fluid contents.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A system for assisting cardiac circulation comprising:
   an intracardiac device comprising:
      an elongate tubular collapsible body with first and second ends and an internal lumen therebetween;
      a pump positioned within the internal lumen, the pump comprising a rotatable housing having first and second open ends and an internal passage therebetween, and one or more blades coupled to an inner surface of the housing extending into the internal passage;
      an actuator coupled to the housing and configured to rotate the housing; and
   a cleaning device comprising:
      an implantable pump having an inlet and an outlet fluidly connectable to the internal lumen of the tubular body.

2. The device of claim 1, further comprising a wireless power system having a transmitting coil electrically connected to a battery, and an implantable receiving coil electrically connected to the pump.

3. The device of claim 1, wherein the body has a collapsible stent construction having a membrane covering.

4. The device of claim 3, wherein the membrane covering is pericardium, a polymer or combinations thereof.

5. The device of claim 1, wherein the actuator comprises a motor coupled to the rotatable housing.

6. The device of claim 5, wherein the motor is coupled to one of the first and second open ends of the housing.

7. The device of claim 6, wherein the motor is coupled to an internal or external surface of the housing.

8. The device of claim 1, wherein the actuator comprises one or more magnets coupled to the housing.

9. The device of claim 1, wherein the rotor comprises a plurality of helical blades extending from the inner surface of the housing.

10. The device of claim 9, wherein each of the helical blades has a length less than half an inner diameter of the housing.

11. The device of claim 10, wherein each of the helical blades has an adjustable pitch.

12. The device of claim 1, wherein the pump further comprises a diffusor.

13. The device of claim 1, wherein the tubular body is movable between a collapsed configuration for advancement through a vessel in a patient, and an expanded configuration.

14. The device of claim 1, further comprising first and second valves positioned at, or near, the first and second ends of the tubular body, respectively, wherein the first and second valves are movable between an open position, wherein the first and second ends allow fluid passage therethrough, to a closed position, wherein the first and second ends are substantially sealed.

15. The device of claim 1, further comprising a transmitting coil and an implantable receiving coil coupled to the pump, the transmitting coil being configured to wirelessly transmit energy to the receiving coil.

16. The device of claim 1, further comprising a wireless receiver and a controller coupled to the wireless receiver and configured to modulate a speed of the pump.

17. The device of claim 1, wherein the tubular body is configured for implanting within a right atrium of a patient's heart to form a fluid pathway between a left atrium and an aorta of the patient.

18. The device of claim 17, wherein the first end includes an anchor configured for securing the first end to a fossa ovalis of the patient and the second end includes an anchor configured for securing to a sinotubular junction of the patient.

19. The system of claim 1, further comprising a cleaning port coupled to the implantable pump by a cleaning line.

20. The system of claim 1, wherein the implantable pump is a centrifugal pump.

21. The system of claim 20, wherein the centrifugal pump comprising an impeller and an actuator for rotating the impeller.

22. The system of claim 21, wherein the actuator comprises one or more magnets.

* * * * *